(12) United States Patent
Bush

(10) Patent No.: US 9,226,960 B2
(45) Date of Patent: Jan. 5, 2016

(54) FGF MODULATION OF IN VIVO ANTIBODY PRODUCTION AND HUMORAL IMMUNITY

(71) Applicant: Andrew B. Bush, Princeton, NJ (US)

(72) Inventor: Andrew B. Bush, Princeton, NJ (US)

( * ) Notice: Subject to any disclaimer, the term of this patent is extended or adjusted under 35 U.S.C. 154(b) by 244 days.

(21) Appl. No.: 13/888,124

(22) Filed: May 6, 2013

(65) Prior Publication Data

US 2013/0236483 A1 Sep. 12, 2013

Related U.S. Application Data

(63) Continuation-in-part of application No. 12/941,070, filed on Nov. 7, 2010, now Pat. No. 8,435,525.

(60) Provisional application No. 61/324,947, filed on Apr. 16, 2010.

(51) Int. Cl.
| | |
|---|---|
| A61K 39/39 | (2006.01) |
| A61K 45/00 | (2006.01) |
| C07K 14/50 | (2006.01) |
| C07K 16/00 | (2006.01) |

(52) U.S. Cl.
CPC ............... *A61K 39/39* (2013.01); *A61K 45/00* (2013.01); *C07K 14/503* (2013.01); *C07K 16/00* (2013.01)

(58) Field of Classification Search
CPC ..................................................... A61K 39/39
See application file for complete search history.

(56) References Cited

U.S. PATENT DOCUMENTS

| | | | |
|---|---|---|---|
| 4,994,559 | A | 2/1991 | Moscatelli et al. |
| 5,229,501 | A | 7/1993 | Keifer et al. |
| 5,288,855 | A | 2/1994 | Bergonzoni et al. |
| 5,440,021 | A | 8/1995 | Chuntharapai et al. |
| 5,530,101 | A | 6/1996 | Queen et al. |
| 5,707,632 | A | 1/1998 | Williams et al. |
| 5,891,655 | A | 4/1999 | Ornitz |
| 5,990,088 | A | 11/1999 | Ensoli et al. |
| 6,071,885 | A | 6/2000 | Florkiewicz et al. |
| 6,255,454 | B1 | 7/2001 | Keifer et al. |
| 6,350,593 | B1 | 2/2002 | Williams et al. |
| 6,900,053 | B2 | 5/2005 | Freier |
| 2012/0214740 | A1 | 8/2012 | Imamura et al. |

FOREIGN PATENT DOCUMENTS

| | | |
|---|---|---|
| WO | WO 03/072603 A2 | 9/2003 |
| WO | WO 2007/080325 A1 | 7/2007 |

OTHER PUBLICATIONS

Jain, V.K., et al. "Challenges and opportunities in the targeting of fibroblast growth factor receptors in breast cancer." Breast Cancer Research. (2012), vol. 14:208, pp. 1-9.*
Abraham et al., 1986. *Human basic fibroblast growth factor: nucleotide sequence and genomic organization.* Embo J 5:2523.
Bai et al., *GP369, an FGFR2-IIIb-specific antibody, exhibits potent antitumor activity against human cancers driven by activated FGFR2 signaling.* Cancer Res 2010 70 (19) 7630-9.
Brasile et al., *Bioengineered skin allografts: a new method to prevent humoral response.* ASAIO Journal May-Jun. 2011 57(3): 239-243.
Brunner et al., 1993. *Basic fibroblast growth factor expression in human bone marrow and peripheral blood cells.* Blood 81:631.
Bryant et al., *Vascular remodeling in response to altered blood flow is mediated by fibroblast growth factor-2.* Circ Res, 1999, 84 (3) 323-8.
Camozzi et al., *Pentraxin 3 inhibits fibroblast growth factor 2-dependent activation of smooth muscle cells in vitro and neointima formation in vivo.* Arterioscler Thromb Vasc Biol. Sep. 2005;25(9):1837-42. Epub Jul. 14, 2005.
Chesi et al., *Frequent translocation t(4;14)(p16.3;q32.3) in multiple myeloma is associated with increased expression and activating mutations of fibroblast growth factor receptor 3.* Nature Genetics, 1997, 16 (3) 260-4.
Chou et al., 2003. *Bone marrow immunohistochemical studies of angiogenic cytokines and their receptors in myelofibrosis with myeloid metaplasia.* Leuk Res 27:499.
Coffin et al., 1995. *Abnormal bone growth and selective translational regulation in basic fibroblast growth factor (FGF-2) transgenic mice.* Mol Biol Cell 6:1861.
Dono et al., 1998. *Impaired cerebral cortex development and blood pressure regulation in FGF-2-deficient mice.* Embo J 17:4213.
Dutt et al., *Drug-sensitive FGFR2 mutations in endometrial carcinoma.* Proc Natl Acad Sci U S A. Jun. 24, 2008;105(25):8713-7.
Fagarasan et al., 2000. *T-Independent immune response: new aspects of B cell biology.* Science 290:89.
Firme et al., *FGF signaling inhibits the proliferation of human myeloma cells and reduces c-myc expression.* BMC Cell Biol. Dec. 4, 2003;4:17.
Gavine et al., *AZD4547: an orally bioavailable, potent, and selective inhibitor of the fibroblast growth factor receptor tyrosine kinase family*, Cancer Res. Apr. 15, 2012;72(8):2045-56. doi: 10.1158/0008-5472.CAN-11-3034. Epub Feb. 27, 2012.
Guagnano et al, *Discovery of 3-(2,6-dichloro-3,5-dimethoxyphenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase.* J Med Chem. 2011, 54 (20) 7066-83.
Guagnano et al., *FGFR genetic alterations predict for sensitivity to NVP-BGJ398,a selective pan-FGFR inhibitor.* Cancer Discov. Sep. 20, 2012, CD-12-0210, Published Online.
Gozgit et al., *Ponatinib (AP24534), a multitargeted pan-FGFR inhibitor with activity in multiple FGFR-amplified or mutated cancer models*, Mol Cancer Ther 2012, 10(1): 126-137.
Harding et al., *Preclinical efficacy of FP-1039 (FGFR1:Fc) in endometrial carcinoma models with activating mutations in FGFR2.* 101st Annual Meeting of the American Association for Cancer Research. abstr. 2597, Apr. 17, 2010.
Hori et al., *Suppression of solid tumor growth by immunoneutralizing monoclonal antibody against human basic fibroblast growth factor.* Cancer Res, 1991, 51 (22) 6180-4.

(Continued)

Primary Examiner — Noble Jarrell
Assistant Examiner — John S Kenyon
(74) *Attorney, Agent, or Firm* — Paul Diamond, Esq.; Diamond Law Office, LLC

(57) ABSTRACT

The invention provides methods for increasing or decreasing antibody production in vivo by inhibiting or promoting the activity of fibroblast growth factor-2 (FGF2) respectively.

13 Claims, 3 Drawing Sheets

(56) References Cited

OTHER PUBLICATIONS

Karrer et al., 2000. *Antiviral B cell memory in the absence of mature follicular dendritic cell networks and classical germinal centers in TNFR1-/- mice.* J Immunol 164:768.

Keer et al. *Enrolling a rare patient population: Establishing proof of concept for FP-1039, an FGF "trap," in endometrial cancer patients with the S252W FGFR2 mutation.* J Clin Oncol 28: 15s, 2010, ASCO Annual Meeting 2010, Abstract TPS260.

Lee et al., *Antibody-producing capacity in human cancer.* Br J Cancer. Sep. 1970;24(3):454-63.

MacLennan et al., 2003. *Extrafollicular antibody responses.* Immunol Rev 194:8.

Martin et al., 2001. *Marginal zone and B1 B cells unite in the early response against T-independent blood-borne particulate antigens.* Immunity 14:617.

Miller et al., 2000. *Compensation by fibroblast growth factor 1 (FGF1) does not account for the mild phenotypic defects observed in FGF2 null mice.* Mol Cell Biol 20:2260.

Ornitz et al., 1996. *Receptor specificity of the fibroblast growth factor family.* J Biol Chem 271:15292.

Ornitz et al., 2001. *Fibroblast growth factors.* Genome Biol 2.

Ortega et al., 1998. *Neuronal defects and delayed wound healing in mice lacking fibroblast growth factor 2.* Proc Natl Acad Sci U S A 95:5672.

Pasparakis et al., 1996. *Immune and inflammatory responses in TNF alpha-deficient mice: a critical requirement for TNF alpha in the formation of primary B cell follicles, follicular dendritic cell networks and germinal centers, and in the maturation of the humoral immune response.* J Exp Med 184:1397.

Qing et al., *Antibody-based targeting of FGFR3 in bladder carcinoma and t(4;14)-positive multiple myeloma in mice.* J Clin Invest. May 2009;119(5):1216-29.

Ravetch et al., 2000. *Immune inhibitory receptors.* Science 290:84.

Salzer et al. *Common variable immunodeficiency (CVID): exploring the multiple dimensions of a heterogeneous disease.* Ann N Y Acad Sci. Feb. 2012;1250:41-9. Epub Feb. 2, 2012.

Takai et al., 1996. *Augmented humoral and anaphylactic responses in Fc gamma RII-deficient mice.* Nature 379:346.

Takeuchi et al., 1999. *Differential roles of TLR2 and TLR4 in recognition of gram-negative and gram-positive bacterial cell wall components.* Immunity 11:443.

Tolcher et al., $22^{nd}$ EORTC-NCI-AACR Symposium on Molecular Targets and Cancer Therapeutics, Nov. 16-19, 2010 Berlin, Germany. *Preliminary Results of a Dose Escalation Study of the FGF "trap" FP-1039 (FGFR1:Fc) in Patients with Advanced Malignancies.*

Trudel et al., *The inhibitory anti-FGFR3 antibody, PRO-001, is cytotoxic to t(4;14) multiple myeloma cells.* Blood. May 15, 2006;107(10):4039-46.

Wang et al., *A novel monoclonal antibody to fibroblast growth factor 2 effectively inhibits growth of hepatocellular carcinoma xenografts.* Mol Cancer Ther. Apr. 2012;11(4):864-72.

Wiedemann et al., 2000. *Characterization of a novel protein (FGFRL1) from human cartilage related to FGF receptors.* Genomics 69:275.

Yang et al., 1998. *Toll-like receptor-2 mediates lipopolysaccharide-induced cellular signalling.* Nature 395:284.

Zhou et al., 1998. *Fibroblast growth factor 2 control of vascular tone.* Nature Medicine 4:201.

Immunologic Deficiency Syndromes, in MeSH Database, National Center for Biotechnology Information, Bethesda, MD, USA [online], [retrieved on May 20, 2014]. Retrieved from the Internet: <URL: http://www.ncbi.nlm.nih.gov/mesh/68007153 >.

Severe Combined Immunodeficiency, in MeSH Database, NCBI, Bethesda, MD, USA [online], [retrieved on Feb. 27, 2015]. Retrieved from the Internet: <URL: http://www.ncbi.nlm.nih.gov/mesh/68016511>.

\* cited by examiner

SEQUENCE LISTING

<160> NUMBER OF SEQ ID NOS: 57

<210> SEQ ID NO 1
<211> LENGTH: 288
<212> TYPE: PRT
<213> ORGANISM: Homo sapiens

<400> SEQUENCE: 1

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Arg Gly Arg Gly Arg
            100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 2
<211> LENGTH: 6774
<212> TYPE: DNA
<213> ORGANISM: Homo sapiens

<400> SEQUENCE: 2
cggccccaga aacccgagc gagtaggggg cggcgcgcag gagggaggag aactgggggc      60
gcgggaggct ggtgggtgtg gggggtggag atgtagaaga tgtgacgccg cggcccggcg     120

```
ggtgccagat tagcggacgc ggtgcccgcg gttgcaacgg gatcccgggc gctgcagctt      180
gggaggcggc tctccccagg cggcgtccgc ggagacaccc atccgtgaac cccaggtccc      240
gggccgccgg ctcgccgcgc accaggggcc ggcggacaga gagcggccg agcggctcga       300 ggctggggga ccgcgggcgc ggccgcgcgc tgccgggcgg gaggctgggg ggccggggcc      360
ggggccgtgc cccggagcgg gtcggaggcc ggggccgggg ccggggacg gcggctcccc       420 gcgcggctcc agcggctcgg ggatcccggc cgggccccgc agggaccatg gcagccggga      480
gcatcaccac gctgcccgcc ttgcccgagg atggcggcag cggcgccttc ccgcccggcc      540
acttcaagga ccccaagcgg ctgtactgca aaaacggggg cttcttcctg cgcatccacc      600
ccgacggccg agttgacggg gtccgggaga agagcgaccc tcacatcaag ctacaacttc      660
aagcagaaga gagaggagtt gtgtctatca aaggagtgtg tgctaaccgt tacctggcta      720
tgaaggaaga tggaagatta ctggcttcta aatgtgttac ggatgagtgt ttcttttttg      780
aacgattgga atctaataac tacaatactt accggtcaag gaaatacacc agttggtatg      840
tggcactgaa acgaactggg cagtataaac ttggatccaa acaggacct gggcagaaag       900 ctatactttt tcttccaatg tctgctaaga gctgatttta atggccacat ctaatctcat      960
ttcacatgaa agaagaagta tattttagaa atttgttaat gagagtaaaa gaaataaat      1020 gtgtatagct cagtttggat aattggtcaa acaattttt atccagtagt aaaatatgta     1080
accattgtcc cagtaaagaa aaataacaaa agttgtaaaa tgtatattct cccttttata     1140
ttgcatctgc tgttacccag tgaagcttac ctagagcaat gatcttttc acgcatttgc      1200 tttattcgaa aagaggcttt taaaatgtgc atgtttagaa acaaaatttc ttcatggaaa     1260
tcatatacat tagaaaatca cagtcagatg tttaatcaat ccaaaatgtc cactatttct     1320
tatgtcattc gttagtctac atgtttctaa acatataaat gtgaatttaa tcaattcctt     1380 tcatagttt ataattctct ggcagttcct tatgatagag tttataaaac agtcctgtgt     1440
aaactgctgg aagttcttcc acagtcaggt caattttgtc aaacccttct ctgtacccat     1500
acagcagcag cctagcaact ctgctggtga tgggagttgt attttcagtc ttcgccaggt     1560
cattgagatc catccactca catcttaagc attcttcctg gcaaaaattt atggtgaatg     1620
aatatggctt taggcggcag atgatataca tatctgactt cccaaaagct ccaggatttg     1680
tgtgctgttg ccgaatactc aggacggacc tgaattctga ttttatacca gtctcttcaa     1740
aaacttctcg aaccgctgtg tctcctacgt aaaaaaagag atgtacaaat caataataat     1800 tacacttta gaaactgtat catcaaagat tttcagttaa agtagcatta tgtaaaggct      1860
caaaacatta ccctaacaaa gtaaagtttt caatacaaat tctttgcctt gtggatatca      1920
agaaatccca aaatattttc ttaccactgt aaattcaaga agcttttgaa atgctgaata     1980
tttctttggc tgctacttgg aggcttatct acctgtacat ttttggggtc agctcttttt     2040
aacttcttgc tgctcttttt cccaaaaggt aaaaatatag attgaaaagt taaaacatttt    2100 tgcatggctg cagttccttt gtttcttgag ataagattcc aaagaactta gattcatttc     2160
ttcaacaccg aaatgctgga ggtgtttgat cagttttcaa gaaacttgga atataaataa     2220
ttttataatt caacaaaggt tttcacattt tataaggttg attttttcaat taaatgcaaa    2280 tttgtgtggc aggattttta ttgccattaa catattttg tggctgcttt ttctacacat      2340
ccagatggtc cctctaactg ggctttctct aattttgtga tgttctgtca ttgtctccca     2400
aagtatttag gagaagccct ttaaaaagct gccttcctct accactttgc tggaaagctt     2460
cacaattgtc acagacaaag attttttgttc caatactcgt tttgcctcta tttttcttgt    2520
```

```
ttgtcaaata gtaaatgata tttgcccttg cagtaattct actggtgaaa aacatgcaaa    2580
gaagaggaag tcacagaaac atgtctcaat tcccatgtgc tgtgactgta gactgtcttg    2640
ccatagactg tcttacccat ccccttggata tgctcttgtt ttttccctct aatagctatg   2700
gaaagatgca tagaaagagt ataatgtttt aaaacataag gcattcgtct gccattttc    2760 aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940 tgaaccccg tctctacaaa aaaacacaaa aaatagccag gcatggtggc gtgtacatgt     3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt tccttaata agaaagtaa ttttactct gatgtgcaat       3180 acatttgtta ttaaatttat tatttaagat ggtagcacta gtcttaaatt gtataaaata    3240 tccccctaaca tgtttaaatg tccatttttta ttcattatgc tttgaaaaat aattatgggg  3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgcttta ttctgttgta tttttattta ttttaatata    3780
ctgtaagcca aactgaaata acatttgctg ttttataggt ttgaagaaca taggaaaaac    3840
taagaggttt tgttttttatt tttgctgatg aagagatatg tttaaatatg ttgtattgtt    3900
ttgtttagtt acaggacaat aatgaaatgg agtttatatt tgttatttct atttttgttat   3960 atttaataat agaattagat tgaaataaaa tataatggga aataatctgc agaatgtggg    4020
ttttcctggt gtttcccttct gactctagtg cactgatgat ctctgataag gctcagctgc   4080
tttatagttc tctggctaat gcagcagata ctcttcctgc cagtggtaat acgatttttt    4140
aagaaggcag tttgtcaatt ttaatcttgt ggatacctt atactcttag ggtattattt    4200
tatacaaaag ccttgaggat tgcattctat tttctatatg acctcttga tatttaaaaa     4260 acactatgga taacaattct tcatttacct agtattatga agaatgaag gagttcaaac     4320 aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta    4560
gctgctttca gggttttatg aattttcagg caaagcttta atttatacta agcttaggaa    4620
gtatggctaa tgccaacggc agttttttttc ttccttaattc cacatgactg aggcatatat   4680
gatctctggg taggtgagtt gttgtgacaa ccacaagcac ttttttttt tttaaagaaa    4740 aaaaggtagt gaattttaa tcatctggac tttaagaagg attctggagt atacttaggc    4800
ctgaaattat atatatttgg cttggaaatg tgttttctct caattacatc tacaagtaag    4860
```

-continued

| | |
|---|---:|
| tacagctgaa attcagagga cccataagag ttcacatgaa aaaaatcaat ttatttgaaa | 4920 |
| aggcaagatg caggagagag gaagccttgc aaacctgcag actgcttttt gcccaatata | 4980 |
| gattgggtaa ggctgcaaaa cataagctta attagctcac atgctctgct ctcacgtggc | 5040 |
| accagtggat agtgtgagag aattaggctg tagaacaaat ggccttctct ttcagcattc | 5100 |
| acaccactac aaaatcatct tttatatcaa cagaagaata agcataaact aagcaaaagg | 5160 |
| tcaataagta cctgaaacca agattggcta gagatatatc ttaatgcaat ccatttctg | 5220 |
| atggattgtt acgagttggc tatataatgt atgtatggta ttttgatttg tgtaaaagtt | 5280 |
| ttaaaaatca agctttaagt acatggacat ttttaaataa aatatttaaa gacaatttag | 5340 |
| aaaattgcct taatatcatt gttggctaaa tagaataggg gacatgcata ttaaggaaaa | 5400 |
| ggtcatggag aaataatatt ggtatcaaac aaatacattg atttgtcatg atacacattg | 5460 |
| aatttgatcc aatagtttaa ggaataggta ggaaaatttg gtttctattt ttcgatttcc | 5520 |
| tgtaaatcag tgacataaat aattcttagc ttattttata tttccttgtc ttaaatactg | 5580 |
| agctcagtaa gttgtgttag gggattattt ctcagttgag actttcttat atgacatttt | 5640 |
| actatgtttt gacttcctga ctattaaaaa taaatagtag atacaatttt cataaagtga | 5700 |
| agaattatat aatcactgct ttataactga ctttattata tttatttcaa agttcattta | 5760 |
| aaggctacta ttcatcctct gtgatggaat ggtcaggaat ttgttttctc atagtttaat | 5820 |
| tccaacaaca atattagtcg tatccaaaat aacctttaat gctaaacttt actgatgtat | 5880 |
| atccaaagct tctcattttc agacagatta tccagaagc agtcataaac agaagaatag | 5940 |
| gtggtatgtt cctaatgata ttatttctac taatggaata aactgtaata ttagaaatta | 6000 |
| tgctgctaat tatatcagct ctgaggtaat ttctgaaatg ttcagactca gtcggaacaa | 6060 |
| attggaaaat ttaaatttt attcttagct ataaagcaag aaagtaaaca cattaatttc | 6120 |
| ctcaacattt ttaagccaat taaaaatata aagatacac accaatatct tcttcaggct | 6180 |
| ctgacaggcc tcctggaaac ttccacatat ttttcaactg cagtataaag tcagaaaata | 6240 |
| aagttaacat aactttcact aacacacaca tatgtagatt tcacaaaatc cacctataat | 6300 |
| tggtcaaagt ggttgagaat atattttta gtaattgcat gcaaaatttt tctagcttcc | 6360 |
| atcctttctc cctcgtttct tcttttttg ggggagctgg taactgatga aatcttttcc | 6420 |
| caccttttct cttcaggaaa tataagtggt tttgttggt taacgtgata cattctgtat | 6480 |
| gaatgaaaca ttggagggaa acatctactg aatttctgta atttaaaata ttttgctgct | 6540 |
| agttaactat gaacagatag aagaatctta cagatgctgc tataaataag tagaaaatat | 6600 |
| aaatttcatc actaaaatat gctatttaa aatctatttc ctatattgta tttctaatca | 6660 |
| gatgtattac tcttattatt tctattgtat gtgttaatga tttatgtaa aaatgtaatt | 6720 |
| gcttttcatg agtagtatga ataaaattga ttagtttgtg ttttcttgtc tccc | 6774 |

<210> SEQ ID NO 3
<211> LENGTH: 733
<212> TYPE: PRT
<213> ORGANISM: Homo sapiens

<400> SEQUENCE: 3

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu

```
                    35                  40                  45
Glu Lys Glu Thr Asp Asn Thr Lys Pro Asn Arg Met Pro Val Ala Pro
 50                  55                  60

Tyr Trp Thr Ser Pro Glu Lys Met Glu Lys Lys Leu His Ala Val Pro
 65                  70                  75                  80

Ala Ala Lys Thr Val Lys Phe Lys Cys Pro Ser Ser Gly Thr Pro Asn
                     85                  90                  95

Pro Thr Leu Arg Trp Leu Lys Asn Gly Lys Glu Phe Lys Pro Asp His
                100                 105                 110

Arg Ile Gly Gly Tyr Lys Val Arg Tyr Ala Thr Trp Ser Ile Ile Met
            115                 120                 125

Asp Ser Val Val Pro Ser Asp Lys Gly Asn Tyr Thr Cys Ile Val Glu
    130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
    195                 200                 205

Ser Lys Ile Gly Pro Asp Asn Leu Pro Tyr Val Gln Ile Leu Lys Thr
210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255

Ser Ile Gly Leu Ser His His Ser Ala Trp Leu Thr Val Leu Glu Ala
            260                 265                 270

Leu Glu Glu Arg Pro Ala Val Met Thr Ser Pro Leu Tyr Leu Glu Ile
    275                 280                 285

Ile Ile Tyr Cys Thr Gly Ala Phe Leu Ile Ser Cys Met Val Gly Ser
290                 295                 300

Val Ile Val Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ser Ala Ser Met Asn Ser Gly Val
            340                 345                 350

Leu Leu Val Arg Pro Ser Arg Leu Ser Ser Ser Gly Thr Pro Met Leu
    355                 360                 365

Ala Gly Val Ser Glu Tyr Glu Leu Pro Glu Asp Pro Arg Trp Glu Leu
    370                 375                 380

Pro Arg Asp Arg Leu Val Leu Gly Lys Pro Leu Gly Glu Gly Cys Phe
385                 390                 395                 400

Gly Gln Val Val Leu Ala Glu Ala Ile Gly Leu Asp Lys Asp Lys Pro
                405                 410                 415

Asn Arg Val Thr Lys Val Ala Val Lys Met Leu Lys Ser Asp Ala Thr
            420                 425                 430

Glu Lys Asp Leu Ser Asp Leu Ile Ser Glu Met Glu Met Met Lys Met
    435                 440                 445

Ile Gly Lys His Lys Asn Ile Ile Asn Leu Leu Gly Ala Cys Thr Gln
450                 455                 460
```

```
Asp Gly Pro Leu Tyr Val Ile Val Glu Tyr Ala Ser Lys Gly Asn Leu
465                 470                 475                 480

Arg Glu Tyr Leu Gln Ala Arg Arg Pro Pro Gly Leu Glu Tyr Cys Tyr
                485                 490                 495

Asn Pro Ser His Asn Pro Glu Glu Gln Leu Ser Ser Lys Asp Leu Val
            500                 505                 510

Ser Cys Ala Tyr Gln Val Ala Arg Gly Met Glu Tyr Leu Ala Ser Lys
        515                 520                 525

Lys Cys Ile His Arg Asp Leu Ala Ala Arg Asn Val Leu Val Thr Glu
    530                 535                 540

Asp Asn Val Met Lys Ile Ala Asp Phe Gly Leu Ala Arg Asp Ile His
545                 550                 555                 560

His Ile Asp Tyr Tyr Lys Lys Thr Thr Asn Gly Arg Leu Pro Val Lys
                565                 570                 575

Trp Met Ala Pro Glu Ala Leu Phe Asp Arg Ile Tyr Thr His Gln Ser
            580                 585                 590

Asp Val Trp Ser Phe Gly Val Leu Leu Trp Glu Ile Phe Thr Leu Gly
        595                 600                 605

Gly Ser Pro Tyr Pro Gly Val Pro Val Glu Glu Leu Phe Lys Leu Leu
    610                 615                 620

Lys Glu Gly His Arg Met Asp Lys Pro Ser Asn Cys Thr Asn Glu Leu
625                 630                 635                 640

Tyr Met Met Met Arg Asp Cys Trp His Ala Val Pro Ser Gln Arg Pro
                645                 650                 655

Thr Phe Lys Gln Leu Val Glu Asp Leu Asp Arg Ile Val Ala Leu Thr
            660                 665                 670

Ser Asn Gln Glu Tyr Leu Asp Leu Ser Met Pro Leu Asp Gln Tyr Ser
        675                 680                 685

Pro Ser Phe Pro Asp Thr Arg Ser Ser Thr Cys Ser Ser Gly Glu Asp
    690                 695                 700

Ser Val Phe Ser His Glu Pro Leu Pro Glu Glu Pro Cys Leu Pro Arg
705                 710                 715                 720

His Pro Ala Gln Leu Ala Asn Gly Gly Leu Lys Arg Arg
                725                 730

<210> SEQ ID NO 4
<211> LENGTH: 3365
<212> TYPE: DNA
<213> ORGANISM: Homo sapiens

<400> SEQUENCE: 4
gcaccgagcg ccgccgggag tcgagcgccg ccgcggagc tccttgcgacc ccgccaggac      60 ccgaacagag cccgggggcg gcgggccgga gccggggacg cgggcacacg cccgctcgca     120
caagccacgg cggactctcc cgaggcggaa cctccacgcc gagcgagggt cagtttgaaa     180
aggaggatcg agctcactgt ggagtatcca tggagatgtg gagccttgtc accaacctct     240
aactgcagaa ctgggatgtg agctggaag tgcctcctct tctgggctgt gctggtcaca      300
gccacactct gcaccgctag gccgtccccg accttgcctg aacaagatgc tctcccctcc     360
tcggaggatg atgatgatga tgatgactcc tcttcagagg agaaagaaac agataacacc     420
aaaccaaacc gtatgccgt agctccatat tggacatccc cagaaaagat ggaaaagaaa     480
ttgcatgcag tgccggctgc caagacagtg aagttcaaat gcccttccag tgggacccca     540
aaccccacac tgcgctggtt gaaaaatggc aaagaattca acctgaccca gaattgga      600
```

-continued

```
ggctacaagg tccgttatgc cacctggagc atcataatgg actctgtggt gccctctgac    660
aagggcaact acacctgcat tgtggagaat gagtacggca gcatcaacca cataccag      720 ctggatgtcg tggagcggtc ccctcaccgg ccatcctgc aagcagggtt gcccgccaac    780
aaaacagtgg ccctgggtag caacgtggag ttcatgtgta aggtgtacag tgacccgcag    840
ccgcacatcc agtggctaaa gcacatcgag gtgaatggga gcaagattgg cccagacaac    900
ctgccttatg tccagatctt gaagactgct ggagttaata ccaccgacaa agagatggag    960
gtgcttcact aagaaatgt ctcctttgag gacgcagggg agtatacgtg cttggcgggt    1020
aactctatcg gactctccca tcactctgca tggttgaccg ttctggaagc cctggaagag    1080
aggccggcag tgatgacctc gccctgtac ctggagatca tcatctattg cacaggggcc     1140
ttcctcatct cctgcatggt ggggtcggtc atcgtctaca agatgaagag tggtaccaag    1200
aagagtgact ccacagcca gatggctgtg cacaagctgg ccaagagcat ccctctgcgc    1260
agacaggtaa cagtgtctgc tgactccagt gcatccatga actctggggt tcttctggtt    1320
cggccatcac ggctctcctc cagtgggact cccatgctag caggggtctc tgagtatgag    1380
cttcccgaag accctcgctg ggagctgcct cgggacagac tggtcttagg caaacccctg    1440
ggagagggct gctttgggca ggtggtgttg gcagaggcta tcgggctgga caaggacaaa    1500
cccaaccgtg tgaccaaagt ggctgtgaag atgttgaagt cggacgcaac agagaaagac    1560
ttgtcagacc tgatctcaga aatggagatg atgaagatga tcgggaagca taagaatatc    1620
atcaacctgc tgggggcctg cacgcaggat ggtcccttgt atgtcatcgt ggagtatgcc    1680
tccaagggca acctgcggga gtacctgcag gcccggaggc cccagggct ggaatactgc     1740 tacaacccca gccacaaccc agaggagcag ctctcctcca aggacctggt gtcctgcgcc    1800
taccaggtgg cccgaggcat ggagtatctg gcctccaaga agtgcataca ccgagacctg    1860
gcagccagga atgtcctggt gacagaggac aatgtgatga agatagcaga ctttggcctc    1920
gcacgggaca ttcaccacat cgactactat aaaaagacaa ccaacggccg actgcctgtg    1980
aagtggatgg cacccgaggc attatttgac cggatctaca cccaccagag tgatgtgtgg    2040
tctttcgggg tgctcctgtg ggagatcttc actctgggcg gctccccata ccccggtgtg    2100
cctgtggagg aacttttcaa gctgctgaag gagggtcacc gcatggacaa gcccagtaac    2160
tgcaccaacg agctgtacat gatgatgcgg gactgctggc atgcagtgcc ctcacagaga    2220
cccaccttca gcagctggt ggaagacctg gaccgcatcg tggccttgac ctccaaccag     2280
gagtacctgg acctgtccat gccctggac cagtactccc ccagctttcc cgacacccgg     2340
agctctacgt gctcctcagg ggaggattcc gtcttctctc atgagccgct gcccgaggag    2400
ccctgcctgc cccgacaccc agcccagctt gccaatggcg gactcaaacg ccgctgactg    2460
ccacccacac gccctcccca gactccaccg tcagctgtaa ccctcaccca gcccctgc      2520 tgggcccacc acctgtccgt ccctgtcccc tttcctgctg gcaggagccg gctgcctacc    2580
aggggccttc ctgtgtggcc tgccttcacc ccactcagct cacctctccc tccacctcct    2640
ctccacctgc tggtgagagg tggcaaagag gcagatcttt gctgccagcc acttcatccc    2700
ctcccagatg ttggaccaac acccctccct gccaccagge actgcctgga gggcagggag    2760
tgggagccaa tgaacaggca tgcaagtgag agcttcctga gctttctcct gtcggtttgg    2820
tctgttttgc cttcacccat aagccctcg cactctggtg gcaggtgcct tgtcctcagg     2880
gctacagcag tagggaggtc agtgcttcgt gcctcgattg aaggtgacct ctgccccaga    2940
```

```
taggtggtgc cagtggctta ttaattccga tactagtttg ctttgctgac caaatgcctg    3000
gtaccagagg atggtgaggc gaaggccagg ttgggggcag tgttgtggcc ctggggccca    3060
gccccaaact gggggctctg tatatagcta tgaagaaaac acaaagtgta taaatctgag    3120
tatatattta catgtctttt taaaagggtc gttaccagag atttacccat cgggtaagat    3180
gctcctggtg gctgggaggc atcagttgct atatattaaa aacaaaaaag aaaaaaaagg    3240
aaaacgtttt taaaaggtc atatatttt tgctacttt gctgttttat ttttttaaat       3300
tatgttctaa acctattttc agtttaggtc cctcaataaa aattgctgct gcttcaaaaa    3360
aaaaa                                                                3365
```

<210> SEQ ID NO 5
<211> LENGTH: 821
<212> TYPE: PRT
<213> ORGANISM: Homo sapiens
<400> SEQUENCE: 5

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
```

```
            290                 295                 300
Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
        370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
        450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
        530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
        610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
        690                 695                 700

Pro Gly Ile Pro Val Glu Glu Leu Phe Lys Leu Leu Lys Glu Gly His
705                 710                 715                 720
```

```
Arg Met Asp Lys Pro Ala Asn Cys Thr Asn Glu Leu Tyr Met Met Met
            725                 730                 735

Arg Asp Cys Trp His Ala Val Pro Ser Gln Arg Pro Thr Phe Lys Gln
        740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
        770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
            805                 810                 815

Gly Ser Val Lys Thr
            820

<210> SEQ ID NO 6
<211> LENGTH: 4654
<212> TYPE: DNA
<213> ORGANISM: Homo sapiens

<400> SEQUENCE: 6
ggcggcggct ggaggagagc gcggtggaga gccgagcggg cgggcggcgg gtgcggagcg     60
ggcgagggag cgcgcgcggc cgccacaaag ctcgggcgcc gcggggctgc atgcggcgta    120
cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattgagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tgggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc gggggggaacc   1200
caatgccaac catgcggtgg ctgaaaaacg gaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga tgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
```

```
agccccacat ccagtggatc aagcacgtgg aaaagaacgg cagtaaatac gggcccgacg    1560
ggctgcccta cctcaaggtt ctcaaggccg ccggtgttaa caccacggac aaagagattg    1620
aggttctcta tattcggaat gtaacttttg aggacgctgg ggaatatacg tgcttggcgg    1680
gtaattctat tgggatatcc tttcactctg catggttgac agttctgcca gcgcctggaa    1740
gagaaaagga gattacagct tccccagact acctggagat agccatttac tgcatagggg    1800
tcttcttaat cgcctgtatg gtggtaacag tcatcctgtg ccgaatgaag aacacgacca    1860
agaagccaga cttcagcagc agccggctg tgcacaagct gaccaaacgt atccccctgc     1920
ggagacaggt aacagtttcg gctgagtcca gctcctccat gaactccaac accccgctgg    1980
tgaggataac aacacgcctc tcttcaacgg cagacacccc catgctggca ggggtctccg    2040
agtatgaact tccagaggac ccaaaatggg agtttccaag agataagctg acactgggca    2100
agcccctggg agaaggttgc tttgggcaag tggtcatggc ggaagcagtg ggaattgaca    2160
aagacaagcc caaggaggcg gtcaccgtgg ccgtgaagat gttgaaagat gatgccacag    2220
agaaagacct ttctgatctg gtgtcagaga tggagatgat gaagatgatt gggaaacaca    2280
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttaggggc tcgccctacc      2760 cagggattcc cgtggaggaa cttttttaagc tgctgaagga aggacacaga atggataagc    2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattcacct agttaccctg    3000
acacaagaag ttcttgttct tcaggagatg attctgtttt ttctccagac cccatgcctt    3060
acgaaccatg ccttcctcag tatccacaca taaacggcag tgttaaaaca tgaatgactc    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttttaa tagctatttg ctaaatgctg ttcttacaca taatttctta    3660
attttcaccg agcagaggtg gaaaaatact tttgctttca gggaaaatgg tataacgtta    3720
atttattaat aaattggtaa tatacaaaac aattaatcat ttatagtttt ttttgtaatt    3780
taagtggcat ttctatgcag gcagcacagc agactagtta atctattgct tggacttaac    3840
```

```
tagttatcag atcctttgaa aagagaatat ttacaatata tgactaattt ggggaaaatg    3900 aagtttgat ttatttgtgt ttaaatgctg ctgtcagacg attgttctta gacctcctaa    3960
atgccccata ttaaaagaac tcattcatag gaaggtgttt cattttggtg tgcaaccctg    4020
tcattacgtc aacgcaacgt ctaactggac ttcccaagat aaatggtacc agcgtcctct    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga aacacagagt tgttctgctg atagttttgg    4320
ggatacgtcc atcttttaa gggattgctt tcatctaatt ctggcaggac ctcaccaaaa    4380
gatccagcct catacctaca tcagacaaaa tatcgccgtt gttccttctg tactaaagta    4440 tgtgttttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttat tttttaata aaaaaaaaaa aaaa                                 4654
```

<210> SEQ ID NO 7
<211> LENGTH: 806
<212> TYPE: PRT
<213> ORGANISM: Homo sapiens

<400> SEQUENCE: 7

```
Met Gly Ala Pro Ala Cys Ala Leu Ala Leu Cys Val Ala Val Ala Ile
 1               5                  10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
```

-continued

```
                225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
                275                 280                 285
Lys His Val Glu Val Asn Gly Ser Lys Val Gly Pro Asp Gly Thr Pro
                290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
                340                 345                 350
Trp Leu Val Val Leu Pro Ala Glu Glu Glu Leu Val Glu Ala Asp Glu
                355                 360                 365
Ala Gly Ser Val Tyr Ala Gly Ile Leu Ser Tyr Gly Val Gly Phe Phe
                370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
                420                 425                 430
Ser Asn Thr Pro Leu Val Arg Ile Ala Arg Leu Ser Ser Gly Glu Gly
                435                 440                 445
Pro Thr Leu Ala Asn Val Ser Glu Leu Glu Leu Pro Ala Asp Pro Lys
                450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
                500                 505                 510
Asp Ala Thr Asp Lys Asp Leu Ser Asp Leu Val Ser Glu Met Glu Met
                515                 520                 525
Met Lys Met Ile Gly Lys His Lys Asn Ile Ile Asn Leu Leu Gly Ala
                530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
                580                 585                 590
Asp Leu Val Ser Cys Ala Tyr Gln Val Ala Arg Gly Met Glu Tyr Leu
                595                 600                 605
Ala Ser Gln Lys Cys Ile His Arg Asp Leu Ala Ala Arg Asn Val Leu
                610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
```

```
Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 8
<211> LENGTH: 4304
<212> TYPE: DNA
<213> ORGANISM: Homo sapiens

<400> SEQUENCE: 8
gtcgcgggca gctggcgccg cgcggtcctg ctctgccggt cgcacggacg caccggcggg      60
ccgccggccg gagggacggg gcgggagctg ggcccgcgga cagcgagccg gagcgggagc     120
cgcgcgtagc gagccgggct ccggcgctcg ccagtctccc gagcggcgcc cgcctcccgc     180
cggtgcccgc gccgggccgt gggggcagc atgcccgcgc gcgctgcctg aggacgccgc      240
ggcccccgcc cccgccatgg cgccccctgc ctgcgccctc gcgctctgcg tggccgtggc     300
catcgtggcc ggcgcctcct cggagtcctt ggggacggag cagcgcgtcg tggggcgagc     360
ggcagaagtc ccgggcccag agcccggcca gcaggagcag ttggtcttcg gcagcgggga     420
tgctgtggag ctgagctgtc ccccgccggg ggtggtccc atggggccca ctgtctgggt      480
caaggatggc acagggctgg tgccctcgga gcgtgtcctg gtgggccc agcggctgca      540 ggtgctgaat gcctcccacg aggactccgg ggcctacagc tgccggcagc ggctcacgca     600
gcgcgtactg tgccacttca gtgtgcgggt gacagacgct ccatcctcgg agatgacga     660 agacggggag gacgaggctg aggacacagg tgtggacaca ggggccccct actgacacg      720 gcccgagcgg atggacaaga agctgctggc cgtgccggcc gccaacaccg tccgcttccg     780
ctgcccagcc gctggcaacc ccactccctc catctcctgg ctgaagaacg gcagggagtt     840
ccgcggcgag caccgcattg gaggcatcaa gctgcggcat cagcagtgga gcctggtcat     900
ggaaagcgtg gtgccctcgg accgcggcaa ctacacctgc gtcgtggaga acaagtttgg     960
cagcatccgg cagacgtaca cgctggacgt gctggagcgc tccccgcacc ggcccatcct    1020
gcaggcgggg ctgccggcca accagacggc ggtgctgggc agcgacgtgg agttccactg    1080
caaggtgtac agtgacgcac agccccacat ccagtggctc aagcacgtgg aggtgaatgg    1140
cagcaaggtg ggcccggacg gcacaccta cgttaccgtg ctcaagacgg cgggcgctaa    1200
```

| | |
|---|---|
| caccaccgac aaggagctag aggttctctc cttgcacaac gtcacctttg aggacgccgg | 1260 |
| ggagtacacc tgcctggcgg gcaattctat tgggttttct catcactctg cgtggctggt | 1320 |
| ggtgctgcca gccgaggagg agctggtgga ggctgacgag gcgggcagtg tgtatgcagg | 1380 |
| catcctcagc tacggggtgg gcttcttcct gttcatcctg gtggtggcgg ctgtgacgct | 1440 |
| ctgccgcctg cgcagccccc ccaagaaagg cctgggctcc ccaccgtgc acaagatctc | 1500 |
| ccgcttcccg ctcaagcgac aggtgtccct ggagtccaac gcgtccatga gctccaacac | 1560 |
| accactggtg cgcatcgcaa ggctgtcctc aggggagggc cccacgctgg ccaatgtctc | 1620 |
| cgagctcgag ctgcctgccg accccaaatg ggagctgtct cgggcccggc tgaccctggg | 1680 |
| caagccccct ggggagggct gcttcggcca ggtggtcatg gcggaggcca tcggcattga | 1740 |
| caaggaccgg gccgccaagc ctgtcaccgt agccgtgaag atgctgaaag acgatgccac | 1800 |
| tgacaaggac ctgtcggacc tggtgtctga gatggagatg atgaagatga tcgggaaaca | 1860 |
| caaaaacatc atcaacctgc tgggcgcctg cacgcagggc gggcccctgt acgtgctggt | 1920 |
| ggagtacgcg gccaagggta acctgcggga gtttctgcgg gcgcggcggc cccgggcct | 1980 |
| ggactactcc ttcgacacct gcaagccgcc cgaggagcag ctcaccttca aggacctggt | 2040 |
| gtcctgtgcc taccaggtgg cccggggcat ggagtacttg gcctcccaga agtgcatcca | 2100 |
| cagggacctg gctgcccgca atgtgctggt gaccgaggac aacgtgatga agatcgcaga | 2160 |
| cttcgggctg gcccgggacg tgcacaacct cgactactac aagaagacaa ccaacggccg | 2220 |
| gctgccgtg aagtggatgg cgcctgaggc cttgtttgac cgagtctaca ctcaccagag | 2280 |
| tgacgtctgg tcctttgggg tcctgctctg ggagatcttc acgctggggg ctccccgta | 2340 |
| ccccggcatc cctgtggagg agctcttcaa gctgctgaag gagggccacc gcatggacaa | 2400 |
| gccgccaac tgcacacacg acctgtacat gatcatgcgg gagtgctggc atgccgcgcc | 2460 |
| ctcccagagg cccaccttca agcagctggt ggaggacctg gaccgtgtcc ttaccgtgac | 2520 |
| gtccaccgac gagtacctgg acctgtcggc gcctttcgag cagtactccc cgggtggcca | 2580 |
| ggacaccccc agctccagct cctcagggga cgactccgtg tttgcccacg acctgctgcc | 2640 |
| cccggcccca cccagcagtg ggggctcgcg gacgtgaagg ccactggtc cccaacaatg | 2700 |
| tgaggggtcc ctagcagccc accctgctgc tggtgcacag ccactccccg gcatgagact | 2760 |
| cagtgcagat ggagagacag ctacacagag ctttggtctg tgtgtgtgtg tgtgcgtgtg | 2820 |
| tgtgtgtgtg tgtgcacatc cgcgtgtgcc tgtgtgcgtg cgcatcttgc ctccaggtgc | 2880 |
| agaggtaccc tgggtgtccc cgctgctgtg caacggtctc ctgactggtg ctgcagcacc | 2940 |
| gaggggcctt tgttctgggg ggacccagtg cagaatgtaa gtgggccac ccggtgggac | 3000 |
| ccccgtgggg cagggagctg ggcccgacat ggctccggcc tctgcctttg caccacggga | 3060 |
| catcacaggg tgggcctcgg ccctcccac acccaaagct gagcctgcag ggaagcccca | 3120 |
| catgtccagc accttgtgcc tggggtgtta gtggcaccgc ctccccacct ccaggctttc | 3180 |
| ccacttccca ccctgcccct cagagactga aattacgggt acctgaagat gggagccttt | 3240 |
| accttttatg caaaaggttt attccggaaa ctagtgtaca tttctataaa tagatgctgt | 3300 |
| gtatatggta tatatacata tatatata acatatatgg aagaggaaaa ggctggtaca | 3360 |
| acggaggcct gcgaccctgg gggcacagga ggcaggcatg gccctgggcg gggcgtgggg | 3420 |
| gggcgtggag ggaggcccca gggggtctca cccatgcaag cagaggacca ggccttttc | 3480 |
| tggcaccgca gttttgtttt aaaactggac ctgtatattt gtaaagctat ttatgggccc | 3540 |
| ctggcactct tgttcccaca ccccaacact tccagcattt agctggccac atggcggaga | 3600 |

-continued

```
gttttaattt ttaacttatt gacaaccgag aaggtttatc ccgccgatag agggacggcc    3660
aagaatgtac gtccagcctg ccccggagct ggaggatccc ctccaagcct aaaaggttgt    3720
taatagttgg aggtgattcc agtgaagata ttttatttcc tttgtccttt ttcaggagaa    3780
ttagatttct ataggatttt tctttaggag atttattttt tggacttcaa agcaagctgg    3840
tattttcata caaattcttc taattgctgt gtgtcccagg cagggagacg gtttccaggg    3900
aggggccggc cctgtgtgca ggttccgatg ttattagatg ttacaagttt atatatatct    3960
atatatataa tttattgagt ttttacaaga tgtatttgtt gtagacttaa cacttcttac    4020
gcaatgcttc tagagtttta tagcctggac tgctaccttt caaagcttgg agggaagccg    4080
tgaattcagt tggttcgttc tgtactgtta ctgggccctg agtctgggca gctgtccctt    4140
gcttgcctgc agggccatgg ctcagggtgg tctcttcttg gggcccagtg catggtggcc    4200
agaggtgtca cccaaaccgg caggtgcgat tttgttaacc cagcgacgaa ctttccgaaa    4260
aataaagaca cctggttgct aacctggaaa aaaaaaaaa aaaa                      4304
```

<210> SEQ ID NO 9
<211> LENGTH: 762
<212> TYPE: PRT
<213> ORGANISM: Homo sapiens

<400> SEQUENCE: 9

```
Met Arg Leu Leu Leu Ala Leu Leu Gly Val Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Ser Thr Ser Ser Asn Asp Asp Glu
        115                 120                 125

Asp Pro Lys Ser His Arg Asp Leu Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Gly Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
```

```
                245                 250                 255
Ala Asn Thr Thr Ala Val Val Gly Ser Asp Val Glu Leu Leu Cys Lys
            260                 265                 270
Val Tyr Ser Asp Ala Gln Pro His Ile Gln Trp Leu Lys His Ile Val
        275                 280                 285
Ile Asn Gly Ser Ser Phe Gly Ala Asp Gly Phe Pro Tyr Val Gln Val
    290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
            340                 345                 350
Gly Thr Gly Arg Ile Pro His Leu Thr Cys Asp Ser Leu Thr Pro Ala
        355                 360                 365
Gly Arg Thr Lys Ser Pro Thr Leu Gln Phe Ser Leu Glu Ser Gly Ser
    370                 375                 380
Ser Gly Lys Ser Ser Ser Leu Val Arg Gly Val Arg Leu Ser Ser
385                 390                 395                 400
Ser Gly Pro Ala Leu Leu Ala Gly Leu Val Ser Leu Asp Leu Pro Leu
                405                 410                 415
Asp Pro Leu Trp Glu Phe Pro Arg Asp Arg Leu Val Leu Gly Lys Pro
            420                 425                 430
Leu Gly Glu Gly Cys Phe Gly Gln Val Val Arg Ala Glu Ala Phe Gly
        435                 440                 445
Met Asp Pro Ala Arg Pro Asp Gln Ala Ser Thr Val Ala Val Lys Met
    450                 455                 460
Leu Lys Asp Asn Ala Ser Asp Lys Asp Leu Ala Asp Leu Val Ser Glu
465                 470                 475                 480
Met Glu Val Met Lys Leu Ile Gly Arg His Lys Asn Ile Ile Asn Leu
                485                 490                 495
Leu Gly Val Cys Thr Gln Glu Gly Pro Leu Tyr Val Ile Val Glu Cys
            500                 505                 510
Ala Ala Lys Gly Asn Leu Arg Glu Phe Leu Arg Ala Arg Arg Pro Pro
        515                 520                 525
Gly Pro Asp Leu Ser Pro Asp Gly Pro Arg Ser Ser Glu Gly Pro Leu
    530                 535                 540
Ser Phe Pro Val Leu Val Ser Cys Ala Tyr Gln Val Ala Arg Gly Met
545                 550                 555                 560
Gln Tyr Leu Glu Ser Arg Lys Cys Ile His Arg Asp Leu Ala Ala Arg
                565                 570                 575
Asn Val Leu Val Thr Glu Asp Asn Val Met Lys Ile Ala Asp Phe Gly
            580                 585                 590
Leu Ala Arg Gly Val His His Ile Asp Tyr Tyr Lys Lys Thr Ser Asn
        595                 600                 605
Gly Arg Leu Pro Val Lys Trp Met Ala Pro Glu Ala Leu Phe Asp Arg
    610                 615                 620
Val Tyr Thr His Gln Ser Asp Val Trp Ser Phe Gly Ile Leu Leu Trp
625                 630                 635                 640
Glu Ile Phe Thr Leu Gly Gly Ser Pro Tyr Pro Gly Ile Pro Val Glu
                645                 650                 655
Glu Leu Phe Ser Leu Leu Arg Glu Gly His Arg Met Asp Arg Pro Pro
            660                 665                 670
```

```
            His Cys Pro Pro Glu Leu Tyr Gly Leu Met Arg Glu Cys Trp His Ala
                675                 680                 685

Ala Pro Ser Gln Arg Pro Thr Phe Lys Gln Leu Val Glu Ala Leu Asp
                690                 695                 700

Lys Val Leu Leu Ala Val Ser Glu Glu Tyr Leu Asp Leu Arg Leu Thr
            705                 710                 715                 720

Phe Gly Pro Tyr Ser Pro Ser Gly Gly Asp Ala Ser Ser Thr Cys Ser
                            725                 730                 735

Ser Ser Asp Ser Val Phe Ser His Asp Pro Leu Pro Leu Gly Ser Ser
                        740                 745                 750

Ser Phe Pro Phe Gly Ser Gly Val Gln Thr
                    755                 760

<210> SEQ ID NO 10
<211> LENGTH: 2418
<212> TYPE: DNA
<213> ORGANISM: Homo sapiens

<400> SEQUENCE: 10
agtccagctt gggtccctga gagctgtgag aaggagatgc ggctgctgct ggccctgttg      60
ggggtcctgc tgagtgtgcc tgggcctcca gtcttgtccc tggaggcctc tgaggaagtg     120
gagcttgagc cctgcctggc tcccagcctg agcagcaag agcaggagct gacagtagcc      180
cttgggcagc ctgtgcggct gtgctgtggg cgggctgagc gtggtggcca ctggtacaag     240
gagggcagtc gcctggcacc tgctggccgt gtacggggct ggaggggccg cctagagatt     300
gccagcttcc tacctgagga tgctggccgc tacctctgcc tggcacgagg ctccatgatc     360
gtcctgcaga atctcacctt gattacaggt gactcctcga cctccagcaa cgatgatgag     420
gaccccaagt cccataggga cctctcgaat aggcacagtt accccagca agcaccctac      480 tggacacacc cccagcgcat ggagaagaaa ctgcatgcag tacctgcggg aacaccgtc      540 aagttccgct gtccagctgc aggcaacccc acgcccacca tccgctggct taaggatgga     600
caggcctttc atggggggaa ccgcattgga ggcattcggc tgcgccatca gcactggagt     660
ctcgtgatgg agagcgtggt gccctcggac cgcggcacat acacctgcct ggtagagaac     720
gctgtgggca gcatccgtta taactacctg ctagatgtgc tggagcggtc cccgcaccgg     780
cccatcctgc aggccgggct cccggccaac accacagccg tggtgggcag cgacgtggag     840
ctgctgtgca aggtgtacag cgatgcccag ccccacatcc agtggctgaa gcacatcgtc     900
atcaacggca gcagcttcgg agccgacggt ttccccctat gtgcaagtcct aaagactgca     960 gacatcaata gctcagaggt ggaggtcctg tacctgcgga acgtgtcagc cgaggacgca    1020
ggcgagtaca cctgcctcgc aggcaattcc atcggcctct cctaccagtc tgcctggctc    1080
acggtgctgc caggtactgg gcgcatcccc cacctcacat gtgacagcct gactccagca    1140
ggcagaacca agtctcccac tttgcagttc ccctggagt caggctcctc cggcaagtca    1200
agctcatccc tggtacgagg cgtgcgtctc tcctccagcg gccccgcctt gctcgccggc    1260
ctcgtgagtc tagatctacc tctcgaccca ctatgggagt tccccgggga caggctggtg    1320
cttgggaagc cctaggcga gggctgcttt ggccaggtag tacgtgcaga ggcctttggc     1380
atggaccctg cccggcctga ccaagccagc actgtggccg tcaagatgct caaagacaac    1440
gcctctgaca aggacctggc cgacctggtc tcggagatgg aggtgatgaa gctgatcggc    1500
cgacacaaga acatcatcaa cctgcttggt gtctgcaccc aggaagggcc cctgtacgtg    1560
```

```
atcgtggagt gcgccgccaa gggaaacctg cgggagttcc tgcgggcccg gcgccccca      1620 ggccccgacc tcagcccga cggtcctcgg agcagtgagg ggccgctctc cttcccagtc      1680
ctggtctcct gcgcctacca ggtggcccga ggcatgcagt atctggagtc cggaagtgt      1740 atccaccggg acctggctgc cgcaatgtgt ctggtgactg aggacaatgt gatgaagatt      1800
gctgactttg ggctggcccg cggcgtccac cacattgact actataagaa aaccagcaac      1860
ggccgcctgc ctgtgaagtg gatggcgccc gaggccttgt tgaccgggt gtacacacac       1920 cagagtgacg tgtggtcttt tgggatcctg ctatgggaga tcttcaccct cggggctcc       1980 ccgtatcctg gcatcccggt ggaggagctg ttctcgctgc tgcgggaggg acatcggatg      2040
gaccgacccc cacactgccc cccagagctg tacgggctga tgcgtgagtg ctggcacgca      2100
gcgccctccc agaggcctac cttcaagcag ctggtggagg cgctggacaa ggtcctgctg      2160
gccgtctctg aggagtacct cgacctccgc ctgaccttcg accctattc cccctctggt      2220 ggggacgcca gcagcacctg ctcctccagc gattctgtct tcagccacga cccctgcca      2280 ttgggatcca gctccttccc cttcgggtct ggggtgcaga catgagcaag gctcaaggct      2340
gtgcaggcac ataggctggt ggccttgggc cttggggctc agccacagcc tgacacagtg      2400
ctcgaccttg atagcatg                                                   2418

<210> SEQ ID NO 11
<211> LENGTH: 155
<212> TYPE: PRT
<213> ORGANISM: Bos taurus

<400> SEQUENCE: 11

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 12
<211> LENGTH: 6601
<212> TYPE: DNA
<213> ORGANISM: Bos taurus

<400> SEQUENCE: 12
ccggggccgc gccgcggagc gcgtcggagg ccggggccgg ggcgcggcgg ctcccgcgc       60 ggctccaggg gctcggggac cccgccaggg ccttggtggg gccatggccg ccgggagcat      120
```

```
caccacgctg ccagccctgc cggaggacgg cggcagcggc gctttcccgc cgggccactt     180
caaggacccc aagcggctgt actgcaagaa cgggggcttc ttcctgcgca tccaccccga     240
cggccgagtg gacggggtcc gcgagaagag cgacccacac atcaaactac aacttcaagc     300
agaagagaga ggggttgtgt ctatcaaagg agtgtgtgca aaccgttacc ttgctatgaa     360
agaagatgga agattactag cttctaaatg tgttacagac gagtgtttct tttttgaacg     420
attggagtct aataactaca atacttaccg gtcaaggaaa tactccagtt ggtatgtggc     480
actgaaacga actgggcagt ataaacttgg acccaaaaca ggacctgggc agaaagctat     540 acttttctt ccaatgtctg ctaagagctg atcttaatgg cagcatctga tctcatttta     600
catgaagagg tatatttcag aaatgtgtta atgaaaaaag aaaaatgtgt acagtgagct     660
gctcagtttg ggtaactgtt cagataaccg tttatctaag agtaaaatat ttaaccattg     720
ccttagtttt ttttaaaga aaaacacaa taacagcaaa aattcctgga aaatgtatac     780
atttccactt tttatacagc atttcctttt atccagtgaa acttacttaa agctacaatc     840
tttcatacag ttgcttcatt tgaagaggct tttaaaatgt gtacaaacaa gttttcttca     900
tggaaattat agacattaga aaattaaagt catatttagt tattaaccca aatgtccact     960
acttcctata atatggcaca cattaatcta catgtacaac ttacttaaac atgtacaact    1020
tacttaaaca ttttaaaaac atgtaaatat gaatttaatc cattcctgtc atagttttgt    1080
aattgtctgg cagtttcttg tgatagagtt tatagaacaa gcctgtgtaa actgctggca    1140
gttcttccat ggtcagatca attttgtcaa acccttcttt gtaccatac agcagcagcc    1200 ttgcaactct gcttgttatg ggagtcgtat ttttagtctt gactagatcg ctgagattca    1260
tccactcaca ctttaagcat tcacgctggc aaaaatttat ggtgaatgaa tatggcttta    1320
agcggcagat aatatacata tctgacttcc caaaagctcc tggatgggtg tgctgttgcc    1380
gaatactcag gagggatctg aattcggatt ttataccagt ctcttcaaaa acttctcgaa    1440
ctgctgtatc tcctacataa aagaaaatgt acaaatcaat aacgattata cttttagaaa    1500
tttaatcaaa gattttcaga taaggaagca ttattatgta aagattcaaa aggtaaaaat    1560
ttaccctaag aaaagaaagc tttccctgta aactctgtcc tctggacatc ctgaaaaaac    1620
aaagtatttt cttaccactg tatagctaag aagcttttga ataatatttt ctttggcttc    1680
tacttgcaag cttaccccatc tatatatatg tattttggga gtcacatatt tttaaattct    1740
tcctgcttta tttcccaaaa gttaatattc ctgtatattt tttcattatt atcttgttcc    1800
tgattatcca ttaaaactgc ctaaactgat aaacatttga agtaagaaaa agtgatccat    1860
tcttctttac aaaagtctgt agagctgcag aatatataga actaggaaat gattcaaatc    1920
atccctggtc tctcctggga ctgtcaggcc tctgaagtca taggtcggat ttcgttataa    1980 ccatttgtt atgctcttct agttattctg tcagtggaat cccaccatgg taatttctgg    2040
cattttcttt gttcttgct gtttcaaaga acttggattc attcttctaa caccaaaatg    2100
ctacagtcat cagaagttta aaaaaaaact tgcaatttac agaattttat aatattacca    2160
ggcttttcac attttataaa gttgattttt aaataatatg caaatttcta ggacaggatt    2220
tttattgcca ttaacttatt tttgtggctg ctctttctaa atatccagat gaacctccta    2280
cctgggattt ctgtaatttt ctgatgctgt cattgtctcc caaagtgttt atgaaaagcc    2340
ctaaaaaagc tgccttcctt gtctattttc tgggaagttt cacaattgcc acaagtatag    2400
atttttgttt aaatatcttt taatgccttc attttcttgt ttgtcaggtt gtaaactgta    2460
```

```
tttggcttct cagtagtcct gctagtgagg aataggcaag gaagagcaag taaacaagaa    2520
atgttgcagt gttttttcta ataacagctc tggaaataag cacaggaaga gtagtgtgta    2580
aaatatgaca tctgtctacc atatttgaat tctgtgtgaa cgaactttt aattgagatt     2640 tgctaaagat caaatcaaca tggttagaaa ttatatttt aaactgaaaa tatagaaaaa     2700
tatatgttaa gaaaggaaa acttggctta agaaaaataa ttttgttgt attaaaaaac     2760 ttgtattaag tttgttacag attgtggcac tagtcttaaa ttttacatgt catttgctga    2820
tctgacttaa aaattgttca aatgtttaaa aagttcttta acatttttaa aatgaccatg    2880
gggatcttgt ttagctctta ataacactag tcaagagttt aacatttagt tcctgtgtct    2940
agcctgcttg tatgttatag aagcacagga tggggctggt gagtgaatct gccaggctta    3000
gccatcacca cagcagctga ttcaaaatca gcactgcctg gatagtttga tccatttaac    3060
ttgaatcatg atgtcattaa ctagattaaa aattaaatgg gcaaataagt gcttttagat    3120
ctagaggaac caacccctc tatattaaaa ttgaaatctc ttctccaagg attttatgat    3180
gaattaaaaa ttttaattta ggtaaagtgc gttatttgct ggtattattt taaatgtact    3240
gtaagtaaac tgaataacgg ttttatagat ttgaagaata taggaaaacc aagagggttt    3300 tgttttatt tttgctggtt gaaagatgtt taaaaacatc atagtgtttt atttagttaa    3360
aggacagtac tgaaatggag tttatatttg ttacttctat tttgtaatat ttaataacag    3420
gattaggttg aaataaaata ataggaaaaa ctgtgcagaa tgtggatttt cctggtgtct    3480 cccctcact ctggtacact gatgagctct gagcagaccc cactgcttta cagacctttg    3540
gctatacagg gagttctctt cctgttagtg ctaatgagat tttccccccc ccagaaaggc    3600
agcttctgtt tttaaccta tctatagata ggcttatcgg agaaggcaat ggcaccccac    3660
tccagaactc ttgcctggaa atcccatgg atggaggagc ctggtgggct gcagtccatg     3720
gggtcgctaa gagttggaca cgactgagcg acttcactt cacttttcac tttcatgcat     3780
tggagaagga aatggcaacc cactccggtg ttccttgcctg gagaatccgg gggacgaggg    3840
agcctggtga gctgctgtct atggggtcgc agagtcggac atgactgaag tgacttagca    3900
gcagcataga taccttttg tactctgctt catttaccta atacttatca aagaatgaag      3960
gattccaaac aaatgagctt cttattttaa ctagtatta ctgcttaaca gccagtatga    4020
acatttgcac atttatgatg gcggcagtcc tattacatac tttcctaaaa acagagttta    4080
aagaaaataa ataattcctg gttgatttgg cttcatcatt aagagtaatc tattactata    4140
ctgttacaaa acagaaatgt actctacata gacatggtct ttcagatctc tatgtctctt    4200
atcatttcta gctgctttca gagttttatc acttctgagg caatgcttca gttttcccta    4260
ctcctaggca atatggtaaa tgccagttgc tgctttttc ttaattccat gtggctggag     4320
gcattaaaaa caatctctga ctaggtgggt tgttgttata cccacaagta ttttaaaaa     4380 gtagtgaatt tctagttata tggacttgaa atgttctgga gtacactcaa acctaaagtg    4440
tacttattta catggtgtgg aaatgtgttt atttacattt aaatatatct gaaattcaga    4500
atatcaatga aaactcaaat gaaaaagtt attcatttga agaaaaaaa aaaaaaagt      4560 tattcatttg agaaggcaag gttcagaaga ggaagttata caaacttcct atagactgct    4620
atttgcccag tatggattag ataaggatgt aaaacagaca cttaactagt tcacatgatc    4680
tcatatcaca tgatagtgtg agataaccgg gaattctaga gtaaatggct ttttctttca    4740
gcactggcac tactacaaaa tcctttttatt tcaacagaag acctagggaa gactaagcta    4800
aaggtcagtg agcacctaaa aaccaaaatc tgctatgata tatttgtagt gaaatttatt    4860
```

```
tataggatgt taggagttgg ctgtatacta caaataggac attttcatct gtggaacatt      4920
aaaaaaaaat catttcaagt atatatatat acatttaaaa ataatttagg gcactgcctt      4980
catataaatg atggctaaag agaatagggt acatatacac agtgaggaca aagtcataga      5040
aaaatagtta agtatgaaat gagttatcta ttgatttatt atgataagga ctgtgcctga      5100
cacaatggtt taaggaagag acaggaaaac tcaatttcta ctctcgattt cctgtaaaat      5160
cagtgacaaa gaattcttag attatttcaa acttccctta gatactgagc tcagtaaatt      5220
gttctaggaa attatctctc atttcagact ttctcacatg agacatgtta ccatcttttg      5280
gctttctgac tatcgaaaaa aatagataaa atttccataa acagaagaat ataccacca      5340 ctgttcaata attgccttta aaatatttca catttcattt aaaagttctc ttcaaccttg      5400
tgataaaatg gtcaagaatt tttctaatag taaagttcca acaattttgt tatgccgagt      5460
tgctcagttg tgtctgactc ttgtgactcc atggactgta gcccaccagg ctcttctgtc      5520 catgggatt ctccaggcaa gaatactgga gtgggttgcc atgccctcct ccaggggata      5580
tttccaacca agggatcaaa cccaggtctc cctcattgta ggcagattct taattgtctg      5640
acctaccagg gaaaccctcc aacaatttta gtcaaattca aaatatccct taatgctaac      5700
cttaactgta tatccaaagt ttctcatttc caaattatct agaagcagtc ctaagccaaa      5760
aaacaggtgt tatgctctga atggtattat ttatactaat ggaataaatt gtagtgttaa      5820
gttttgctat taattttata tcagcactga ataacttctt tgaaattttc tgacttagtc      5880
taaaccaatt agaaagtgta aaatctcatt ctcagctcta gagcaagaaa gtaaacacat      5940
aaatttattc agcattttca agtcaattat aaatatataa gatacccacc aatatcttct      6000
ccaggctctg acaggcctcc tgggaacttc cacatgtttt tcagctgtag tattaaatca      6060
gaaagcaaag ttaacacagc tcttatttac taacatacac atacgtagag atgccacaga      6120
agctacccat aattgatcaa ggtggttgag aatttatttt ttcgtaactg ccaccaattt      6180
ttttcagctt ccttcctcac tcctttcttc tctcgggaaa ctgctgactt gtgaaatctt      6240
tcctatcttt ttatttagga aatagaagtg gttttttttta tgttaatgtg ataaattctg      6300
tatgagtgaa acagtggggg gaacatctac tgaatttgta tagttaaaaa ttttttgctgc     6360 tagtttatta aagaatacat gaatcttact gatgctgcta taaattagta gaaaatatat      6420
aaatgtaatc actaaagtat gctatttta atttcaatt tactttctat attgtgtgtc      6480
taatcagata tattaatctt aagagttttc ttgttctctg tgttaatgat tttatgtaaa      6540
aatataattg tctttcctgg gaagtgtgaa taaaattgat ttaagtttct ggctaaaaaa      6600
a                                                                      6601
```

<210> SEQ ID NO 13
<211> LENGTH: 820
<212> TYPE: PRT
<213> ORGANISM: Bos taurus

<400> SEQUENCE: 13

Met Trp Ser Arg Lys Cys Leu Leu Phe Trp Ala Val Leu Val Thr Ala
1               5                   10                  15

Thr Leu Cys Thr Ala Lys Pro Ala Pro Thr Leu Pro Glu Gln Ala Gln
                20                  25                  30

Pro Trp Gly Ala Pro Val Glu Val Glu Ser Leu Leu Val His Pro Gly
            35                  40                  45

Asp Leu Leu Gln Leu Arg Cys Arg Leu Arg Asp Asp Val Gln Ser Ile

```
                50                  55                  60
Asn Trp Leu Arg Asp Gly Val Gln Leu Ala Asp Ser Asn Arg Thr Arg
 65                  70                  75                  80

Ile Thr Gly Glu Glu Val Glu Val Arg Gly Ser Val Pro Ala Asp Ser
                     85                  90                  95

Gly Leu Tyr Ala Cys Val Thr Ser Ser Pro Ser Gly Ser Asp Thr Thr
                    100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
            130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
                180                 185                 190

Lys Glu Phe Lys Pro Asp His Arg Ile Gly Gly Tyr Lys Val Arg Tyr
            195                 200                 205

Ala Thr Trp Ser Ile Ile Met Asp Ser Val Val Pro Ser Asp Lys Gly
            210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
                260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
                340                 345                 350

Trp Leu Thr Val Leu Glu Ala Leu Glu Glu Arg Pro Ala Val Met Thr
            355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Ile Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
                420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
            450                 455                 460

Glu Asp Pro Arg Trp Glu Leu Pro Arg Asp Arg Leu Val Leu Gly Lys
465                 470                 475                 480
```

```
Pro Leu Gly Glu Gly Cys Phe Gly Gln Val Val Leu Ala Glu Ala Ile
            485                 490                 495

Gly Leu Asp Lys Asp Arg Pro Asn Arg Val Thr Lys Val Ala Val Lys
        500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His His Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 14
<211> LENGTH: 3400
<212> TYPE: DNA
<213> ORGANISM: Bos taurus

<400> SEQUENCE: 14
ggctccgcga gtcagcttgc aaaggaggat cgagcccacg gcggagtctc catggaggtg      60
tggagcctgg tcaccaacct ctaaccgcag aactgggatg tggagccgga agtgtctcct     120
```

-continued

```
cttctgggcc gtgctggtca cagccacgct ctgcactgcc aagccggccc cgaccttgcc    180
ggagcaagcc cagccctggg gagcccctgt ggaagtggag tccctcctgg tccaccccgg    240
tgacctgctg cagctccgct gtcggctgcg ggacgatgtt cagagcatca actggctgcg    300
ggacggggtg cagctggcgg acagcaaccg cacgcgcatc accggggagg aggtggaggt    360
tcggggctcc gtgcccgccg actcaggcct ctacgcctgc gtgaccagca gcccctccgg    420
cagtgacacc acctacttct ccgtcaacgt ctcagatgcg ctcccctcgt cggaggacga    480
tgatgacgac gatgactcct cttcggagga gaaggaaaca gataacacca aaccaaaccc    540
cgtggctccg tactggacgt caccagaaaa gatggaaaag aaactgcacg cagtgccagc    600
tgccaagaca gtgaagttca aatgcccttc cagtgggacc ccgaacccca cactgcgctg    660
gctgaaaaac ggcaaagaat tcaagcccga ccacaggatc ggaggctaca aggtccgtta    720
tgccacctgg agcatcatta tggactccgt ggtgccttcg gataagggca actacacctg    780
catcgtggag aacgaatacg gcagcatcaa ccatacctac cagcttgatg ttgtggagcg    840
gtcccctcac cggcccatcc tgcaggcggg cttgccagcc aacaagacgg tggccctggg    900
cagcaacgtg gagttcatgt gcaaggtgta cagtgacccg cagccccaca tccagtggct    960
gaagcacatt gaggtgaacg ggagtaagat tgggccggac aacctgcctt atgtccagat   1020
cttgaagacg gccggagtta acaccaccga caaagagatg gaggtgctgc acttaaggaa   1080
tgtctccttt gaggacgcgg gggagtatac atgcttggcg ggtaactcta tcggactctc   1140
ccatcactct gcatggctga ccgttctgga agccctggaa gagagaccgg cggtgatgac   1200
ttcgccgctg tacctggaga tcatcatcta ttgcacgggg gccttcctca tctcctgcat   1260
ggtggggtct gtcatcatct acaagatgaa gagcggcaca aagaagagtg acttccacag   1320
ccagatggcc gtgcacaagc tggccaagag catccctctg cgcagacagg taacagtgtc   1380
ggctgactcc agcgcgtcca tgaactccgg ggtcctgcta gttcggccct cgcgtctctc   1440
ctccagcggc acccctatgc tggccggggt ctctgaatat gagcttcccg aagaccctcg   1500
ctgggagctg cctcgggaca gactggtttt aggcaagccc ctgggagagg gctgctttgg   1560
gcaggtggtg ctggcggagg ccatcgggct ggacaaggac agacccaacc gtgtgaccaa   1620
agtggccgtg aagatgctga agtcggatgc aacagagaaa gacctgtcgg acctgatctc   1680
cgagatggag atgatgaaga tgattggaaa acacaagaac atcatcaatc tgctgggggc   1740
ctgtacacag gatggtccct tgtatgtcat cgtggagtac gcctccaagg gcaatctccg   1800
agagtacctg caggcccgga ggccgccagg gctggagtac tgctacaacc ccagccacca   1860
ccccgaggag cagctctcct ccaaggacct ggtgtcctgc gcctaccagg tggcccgagg   1920
catggagtat cttgcctcca agaagtgcat ccaccgggac ctggccgcca ggaacgtcct   1980
ggtgacggag gacaacgtga tgaagatcgc ggacttcggt cttgctcgag acatccacca   2040
catcgactac tataaaaaga caaccaacgg ccgactgccc gtcaaatgga tggcaccgga   2100
ggccttgttt gaccggatct acacccacca gagcgacgtg tggtcttttg gggtgctcct   2160
ctgggaaatc ttcactctgg gcggctcccc ataccctggg gtccccgtgg aggagctttt   2220
caagctgctg aaggagggtc atcgtatgga caagcccagt aactgcacca acgagctcta   2280
catgatgatg agagattgct ggcacgcggt cccctctcag agacccacct tcaagcagct   2340
ggtggaagac ctggaccgca tcgtggcctt gacctccaac caggagtacc tggacctgtc   2400
aatgcccctg gaccaatact cccccagctt ccccgacacc cgcagctcca cctgctcctc   2460
cggggaggat tccgtctttt ctcacgagcc cttgcccgag gaaccctgcc tgccccgaca   2520
```

-continued

```
cccggcccag ctggccaacg gcggactcaa acggcgctga ctggccccca cacccgcac    2580 cccttcccgg actccatcct caacgccttg ccctcctcc cgctggactc gctgcctccc    2640
ctgcgctctg ctggccggcc tccctgaggc ccgcacccc gagctcccct cctctcctcc    2700
tcccagcctg acagaggagc agggaagccg gtccttgctg acggctacta cgtggcctgc    2760
ccaacgctgg accaagaccc cctccctgcc gcctggaggg ttgggcagtg agggctgagc    2820
cgccctcgag cgagagccga ctgagctttc ctgcattggt tttgcgtact ctgcgcagcc    2880
catggcccgt gttctgtggc agatcctcgg gccagagcgg gagttgggtg taggggtggt    2940
cagcgcccgg gcctccgcag gcgacctctg ttccagacgg atagtgccag tggtttattg    3000
attccgaaac taatttgctt tgctgaccaa ataccaggta cccgagggtg gggacgcaga    3060
ggccgggagc cggcggcgtg gccctggggc ccagccccga agcagggct ctgtacatag    3120 ctacgaagaa aacacaaagt gtataaatct gagtatatat ttacatgtct ttttaaaagg    3180
gtcgttacca gagatttacc cattgggtaa gatgctcctg gtggttggga ggcatcagtt    3240
gctatatatt aaaacaaag aaaaagaaa aaaaaaaaa aaaaaaaaaa aaaaaaaaa    3300 aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaa                           3400
```

<210> SEQ ID NO 15
<211> LENGTH: 846
<212> TYPE: PRT
<213> ORGANISM: Bos taurus
<220> FEATURE:
<221> NAME/KEY: MOD_RES
<222> LOCATION: (453)..(453)
<223> OTHER INFORMATION: Any amino acid

<400> SEQUENCE: 15

```
Met Gly Leu Thr Ser Thr Trp Arg Tyr Gly Arg Gly Gln Ile Gly
1               5                   10                  15

Thr Val Thr Met Val Ser Trp Gly Arg Phe Leu Cys Leu Val Val
                20                  25                  30

Thr Met Ala Thr Leu Ser Leu Ala Arg Pro Ser Phe Asn Leu Val Asp
            35                  40                  45

Asp Thr Thr Val Glu Pro Glu Pro Pro Thr Lys Tyr Gln Ile Ser
    50                  55                  60

Gln Pro Glu Val Tyr Val Ala Ala Pro Arg Glu Ser Leu Glu Leu Arg
65                  70                  75                  80

Cys Leu Leu Arg Asp Ala Ala Met Ile Ser Trp Thr Lys Asp Gly Val
                85                  90                  95

His Leu Gly Pro Asn Asn Arg Thr Val Leu Ile Gly Glu Tyr Leu Gln
            100                 105                 110

Ile Lys Gly Ala Thr Pro Arg Asp Ser Gly Leu Tyr Ala Cys Thr Ala
        115                 120                 125

Ala Arg Asn Val Asp Ser Glu Thr Val Tyr Phe Met Val Asn Val Thr
    130                 135                 140

Asp Ala Ile Ser Ser Gly Asp Asp Glu Asp Ala Asp Gly Ser Glu
145                 150                 155                 160

Asp Phe Val Ser Glu Asn Ser Asn Ser Lys Arg Ala Pro Tyr Trp Thr
                165                 170                 175

Asn Thr Glu Lys Met Glu Lys Arg Leu His Ala Val Pro Ala Ala Asn
            180                 185                 190
```

```
Thr Val Lys Phe Arg Cys Pro Ala Gly Gly Asn Pro Thr Pro Thr Met
            195                 200                 205
Arg Trp Leu Lys Asn Gly Lys Glu Phe Lys Gln Glu His Arg Ile Gly
    210                 215                 220
Gly Tyr Lys Val Arg Asn Gln His Trp Ser Leu Ile Met Glu Ser Val
225                 230                 235                 240
Val Pro Ser Asp Lys Gly Asn Tyr Thr Cys Val Val Glu Asn Asp Tyr
                245                 250                 255
Gly Ser Ile Asn His Thr Tyr His Leu Asp Val Val Glu Arg Ser Pro
            260                 265                 270
His Arg Pro Ile Leu Gln Ala Gly Leu Pro Ala Asn Ala Ser Thr Val
        275                 280                 285
Val Gly Gly Asp Val Glu Phe Val Cys Lys Val Tyr Ser Asp Ala Gln
    290                 295                 300
Pro His Ile Gln Trp Ile Lys His Val Glu Lys Asn Gly Ser Lys Tyr
305                 310                 315                 320
Gly Pro Asp Gly Leu Pro Tyr Leu Lys Val Leu Lys His Ser Gly Ile
                325                 330                 335
Asn Ser Ser Asn Ala Glu Val Leu Ala Leu Phe Asn Val Thr Glu Ala
            340                 345                 350
Asp Ala Gly Glu Tyr Ile Cys Lys Val Ser Asn Tyr Ile Gly Gln Ala
        355                 360                 365
Asn Gln Ser Ala Trp Leu Thr Val Leu Pro Lys Gln Gln Ala Pro Val
    370                 375                 380
Arg Glu Lys Glu Ile Pro Ala Ser Pro Asp Tyr Leu Glu Ile Ala Ile
385                 390                 395                 400
Tyr Cys Ile Gly Val Phe Phe Ile Ala Cys Met Val Val Thr Val Ile
                405                 410                 415
Leu Cys Arg Met Arg Asn Thr Thr Lys Lys Pro Asp Phe Ser Ser Gln
            420                 425                 430
Pro Ala Val His Lys Leu Thr Lys Arg Ile Pro Leu Arg Arg Gln Val
        435                 440                 445
Thr Glu Ser Arg Xaa Arg Val Ser Ala Glu Ser Ser Ser Ser Met Asn
    450                 455                 460
Ser Asn Thr Pro Leu Val Arg Ile Thr Thr Arg Leu Ser Ser Thr Ala
465                 470                 475                 480
Asp Thr Pro Met Leu Ala Gly Val Ser Glu Tyr Glu Leu Pro Glu Asp
                485                 490                 495
Pro Lys Trp Glu Phe Pro Arg Asp Lys Leu Thr Leu Gly Lys Pro Leu
            500                 505                 510
Gly Glu Gly Cys Phe Gly Gln Val Val Met Ala Glu Ala Val Gly Ile
        515                 520                 525
Asp Lys Glu Lys Pro Lys Glu Ala Val Thr Val Ala Val Lys Met Leu
    530                 535                 540
Lys Asp Asp Ala Thr Glu Lys Asp Leu Ser Asp Leu Val Ser Glu Met
545                 550                 555                 560
Glu Met Met Lys Met Ile Gly Lys His Lys Asn Ile Ile Asn Leu Leu
                565                 570                 575
Gly Ala Cys Thr Gln Asp Gly Pro Leu Tyr Val Ile Val Glu Tyr Ala
            580                 585                 590
Ser Lys Gly Asn Leu Arg Glu Tyr Leu Arg Ala Arg Arg Pro Pro Gly
        595                 600                 605
Met Glu Tyr Ser Tyr Asp Ile Asn Arg Val Pro Glu Glu Gln Met Ala
```

|     |     |     |     |     |     |     |     |     |     |
|-----|-----|-----|-----|-----|-----|-----|-----|-----|-----|
|     |     | 610 |     |     | 615 |     |     | 620 |     |

Phe Lys Asp Leu Val Ser Cys Thr Tyr Gln Leu Ala Arg Gly Met Glu
625                 630                 635                 640

Tyr Leu Ala Ser Gln Lys Cys Ile His Arg Asp Leu Ala Ala Arg Asn
                645                 650                 655

Val Leu Val Thr Glu Asn Asn Val Met Lys Ile Ala Asp Phe Gly Leu
                    660                 665                 670

Ala Arg Asp Ile Asn Asn Ile Asp Tyr Tyr Lys Lys Thr Thr Asn Gly
                675                 680                 685

Arg Leu Pro Val Lys Trp Met Ala Pro Glu Ala Leu Phe Asp Arg Val
                690                 695                 700

Tyr Thr His Gln Ser Asp Val Trp Ser Phe Gly Val Leu Met Trp Glu
705                 710                 715                 720

Ile Phe Thr Leu Gly Gly Ser Pro Tyr Pro Gly Ile Pro Val Glu Glu
                    725                 730                 735

Leu Phe Lys Leu Leu Lys Glu Gly His Arg Met Asp Lys Pro Ala Asn
                740                 745                 750

Cys Thr Asn Glu Leu Tyr Met Met Met Arg Asp Cys Trp His Ala Val
                755                 760                 765

Pro Ser Gln Arg Pro Thr Phe Lys Gln Leu Val Glu Asp Leu Asp Arg
770                 775                 780

Ile Leu Thr Leu Thr Thr Asn Glu Glu Tyr Leu Asp Leu Ser Gln Leu
785                 790                 795                 800

Leu Glu Gln Tyr Ser Pro Ser Tyr Pro Asp Thr Arg Ser Ser Cys Ser
                    805                 810                 815

Ser Gly Asp Asp Ser Val Phe Ser Pro Asp Pro Met Pro Tyr Glu Pro
                820                 825                 830

Cys Leu Pro Gln Tyr Pro His Arg Asn Gly Ser Val Lys Thr
                835                 840                 845

<210> SEQ ID NO 16
<211> LENGTH: 4302
<212> TYPE: DNA
<213> ORGANISM: Bos taurus

<400> SEQUENCE: 16
tttttttttt tgcggggagt tggtcgtttg ctccatcccg acccacgctg ggcgcgggga    60
cagacccgat cgccggggat cgttgccatt caagaggctg cagcagcagc agcagcagca   120
gcggcaaggc cagcgagcgg ccgccgcagc accttggttc ctgagcccac cgccggctga   180
aggcattgct gcaggcagtc catgctcgta gaggaagggt gcagatggga ttaacgtcca   240
catggagata tggaagagga cagggatcg gcactgtaac catggtcagc tggggtcgct   300
tcctctgcct ggttgtggtc accatggcaa ccttgtccct ggcccggccc tccttcaatt   360
tagttgacga taccacggtt gagccggaag agccaccaac caaataccaa atctcccaac   420
cagaagttta cgtggctgcg ccccgggagt cgctagagtt gcgctgcctg ttgcgagatg   480
ccgccatgat cagttggact aaggatgggg tacacttggg gccaacaat aggacagtgc   540 ttattgggga gtatttgcag ataaaaggtg ccacgcctag agactccggc ctctatgctt   600
gtactgctgc taggaacgta gacagtgaga ctgtctactt catggtcaat gtcacagatg   660
ccatctcatc cggagatgat gaggacgacg cagatggctc ggaggatttt gtcagtgaga   720
acagtaacag caagagagca ccatactgga ccaacacaga aagatggaa aaacggctgc   780 acgcggtccc agcagccaac actgtcaagt tccgctgtcc agctgggggg aatccaacac   840

```
caaccatgag gtggctgaaa aacgggaagg aatttaagca ggagcatcgc attggaggct      900
ataaggtacg aaaccagcat tggagcctta ttatggaaag tgtggtcccg tctgacaaag      960
gaaattatac ctgcgtggtg gagaacgatt acgggtccat caatcatacg taccaccttg     1020
acgttgttga gcgatcacca caccggccca tcctccaagc cgggctgccg gcaaatgcct     1080
ccactgtggt tggaggcgat gtggagtttg tctgcaaagt gtacagcgat gcccagcccc     1140
atatccagtg gatcaaacac gtggaaaaga cggcagtaa atatgggccc gacgggctgc      1200
cctatctcaa ggttctgaag cactcgggga taaatagttc caatgcggaa gtgctggctc     1260
tgttcaatgt gacggaggcg gatgctggcg agtatatttg taaggtctcc aattatatag     1320
ggcaggccaa ccagtctgcc tggctcactg tcctgccaaa acagcaagct cctgtaagag     1380
aaaaggagat cccagcttcc ccagactacc tggaaatagc catttactgc ataggggtgt     1440
tcttcatcgc ctgcatggtg gtgacggtca tcttgtgccg gatgaggaac acgaccaaga     1500
agccggactt cagcagccag ccggctgtgc acaagctgac caagcgcatc cccctgcgga     1560
gacaggtaac agaaagtaga taaagagttt ctgctgagtc cagctcctcc atgaactcca     1620
ataccccgtt ggtgaggatt acaactcgcc tctcttcaac tgcagacacc cccatgctgg     1680
cggggggtctc cgagtacgag ctgccagaag atcccaaatg ggagtttcca agagataagc     1740
tgacgctggg caaaccctg ggagaaggtt gctttgggca agtggtcatg gctgaagcag      1800
tgggaattga caaggagaag cccaaggaag cagtcactgt ggccgtgaag atgttgaaag     1860
atgatgccac tgagaaagac ctttctgatc tggtgtccga gatggagatg atgaagatga     1920
ttgggaaaca caaaaatatc ataaatctcc ttggagcctg tactcaggat gggccgctct     1980
atgtcatcgt tgaatacgcc tctaaaggca accttcggga atacctgcgc gcccggaggc     2040
caccccggat ggagtattcc tacgacatca accgcgttcc cgaggagcag atggccttca     2100
aggacctggt gtcgtgtacc taccagctgg cccggggcat ggagtacttg gcttcccaga     2160
aatgcattca tcgagattta gctgccagaa atgttttggt aacagaaaac aacgtgatga     2220
aaatagctga cttttggactg gccagagata tcaacaatat agactattac aaaaagacca     2280
caaatggccg acttccggtc aagtggatgg ctcccgaagc ccttttcgac agagtgtaca     2340
cccatcagag cgatgtctgg tccttcgggg tgttaatgtg ggagatcttc acgttagggg     2400
gttcgcccta cccagggatt cccgtggagg aacttttaa gctgcttaag gaaggacata     2460
ggatggacaa gccagcaaac tgcaccaacg aactgtatat gatgatgaga gactgctggc     2520
atgcggtacc ctcacagaga cccaccttca gcagttggt agaagacttg gatcgaattc      2580
tcacactcac aaccaatgag gaatacttgg acctcagtca gcttcttgaa caatattcac     2640
ctagttaccc tgacacaagg agttcttgct cttcgggaga tgattctgtt ttctctccgg     2700
accccatgcc ttacgaaccc tgccttcctc agtatccaca tagaaacggc agtgttaaaa     2760
catgaatggg cctgtccccc tgtccccaaa caggtggca tcaggaactt agctgtactg      2820
agcaggggg gccttgcctc caggagcctg ttggcttggc ttgtatatat ggatcagagg     2880
agtaaatatt tggaaaagtg atcggcacac gtgtaaagaa tttatccagt tggagacttg     2940
taatcttcac caggagaaca agaaggttgt gggggcaatg gattgccatg gccgccacg      3000
tgcttgtgac ccaccgtggg tactggctgt ggaccagccg gacttgaggc aaacacccgt     3060
tctgcctgcc ttgtgaattt tgtaataatt ggagaaaata tatgtcagcg cacacttata     3120
gagcacaatt gcagtatata ggtgctggat gtatgtaaat atattcaaat tatgtataaa     3180
```

```
tatatattat atatttacaa ggaattattt tttgtattga ttttaaatgg atgtcccagc    3240
gcacctagaa aattggtctc tctctcttt tttaaaaaat agctatttgc taaatgctgt    3300
ttcttacata gaatttctta attttcaccg agcagaggtg gaaaagtact tttgctttca    3360
gggaaaaatg atatgacatt aatttattaa tgaattggta atatacaaaa caatcgtttt    3420
ttgtgttttt ttttggtaat ttaagtggca tttctatgca ggcagcacac cagactagtt    3480
aatctcttgc ttgaacttaa ctagttacca gatcctctga aaagagaaat atttacaaaa    3540
tgtgactaat ttgggggaag tgaagttttg gtttatttgt atttcagctc tgctgtcaga    3600
tgattggtct ttaaccacct aactgcccgt atgaaagagc ccattgatga aaggtgtgt     3660 tgtcttggtg cagcttggtc attgggccca taaacctttc actgggcttc ccaagacaaa    3720
cggtaccagc gttctcctaa aaagatgcct taatctgttc ctcaaaggag gaactctcat    3780
cgagatgcta aaagaatgtt ctgtccagcc gctggccttc tgcccctctc cccgccaagt    3840
tgcacattga tcagatcagc ctgcattctc tttggcgaat cttcatcaca gcttccagat    3900
ttactggcaa cagagaagtc tcttagaatc ttcacgccct gtcggagaaa atggaaacac    3960
tgagttgttc tgctgatagt ttgggggatc cttccatctt tttaagggat cgcttccgcc    4020
tcctctggca ggatctcacc gaaagatccc gccctatgcc aatgtcatgt tactgccatg    4080
gtgttcgttt tgtatgaacg tgttgtgttt tgctttcaaa acaccttctc actctgctct    4140
ggctgtgcaa catgaatgcg gatgacactg attttaacg  tgttatgaaa ttggagaaag    4200
tatttaataa aacctgttaa ttttatact  gacaataaaa atgtttctac agatattaat    4260
gttaacaaga caaataaat  gtcatgcggc ttatttttt  aa                       4302
```

<210> SEQ ID NO 17
<211> LENGTH: 802
<212> TYPE: PRT
<213> ORGANISM: Bos taurus

<400> SEQUENCE: 17

```
Met Gly Ala Pro Ala Arg Ala Leu Ala Phe Cys Val Ala Val Ala Val
1               5                   10                  15

Met Thr Gly Ala Ala Leu Gly Ser Pro Gly Val Glu Pro Arg Val Ala
            20                  25                  30

Arg Arg Ala Ala Glu Val Pro Gly Pro Glu Pro Ser Pro Gln Glu Arg
        35                  40                  45

Ala Phe Gly Ser Gly Asp Thr Val Glu Leu Ser Cys Arg Leu Pro Ala
    50                  55                  60

Gly Val Pro Thr Glu Pro Thr Val Trp Val Lys Asp Gly Val Gly Leu
65                  70                  75                  80

Ala Pro Ser Asp Arg Val Leu Val Gly Pro Gln Arg Leu Gln Val Leu
                85                  90                  95

Asn Ala Ser His Glu Asp Ala Gly Ala Tyr Ser Cys Arg Gln Arg Leu
            100                 105                 110

Ser Gln Arg Leu Leu Cys Leu Phe Ser Val Arg Val Thr Asp Ala Pro
        115                 120                 125

Ser Ser Gly Asp Asp Glu Gly Gly Asp Asp Glu Ala Glu Asp Thr Ala
    130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175
```

Asn Pro Thr Pro Ser Ile Thr Trp Leu Lys Asn Gly Lys Glu Phe Arg
            180                 185                 190

Gly Glu His Arg Ile Gly Gly Ile Lys Leu Arg Gln Gln Gln Trp Ser
        195                 200                 205

Leu Val Met Glu Ser Val Val Pro Ser Asp Arg Gly Asn Tyr Thr Cys
    210                 215                 220

Val Val Glu Asn Lys Phe Gly Arg Ile Gln Gln Thr Tyr Thr Leu Asp
225                 230                 235                 240

Val Leu Glu Arg Ser Pro His Arg Pro Ile Leu Gln Ala Gly Leu Pro
                245                 250                 255

Ala Asn Gln Thr Ala Val Leu Gly Ser Asp Val Glu Phe His Cys Lys
            260                 265                 270

Val Tyr Ser Asp Ala Gln Pro His Ile Gln Trp Leu Lys His Val Glu
        275                 280                 285

Val Asn Gly Ser Lys Val Gly Pro Asp Gly Thr Pro Tyr Val Thr Val
    290                 295                 300

Leu Lys Thr Ala Gly Ala Asn Thr Thr Asp Lys Glu Leu Glu Val Leu
305                 310                 315                 320

Ser Leu Arg Asn Val Thr Phe Glu Asp Ala Gly Glu Tyr Thr Cys Leu
                325                 330                 335

Ala Gly Asn Ser Ile Gly Phe Ser His His Ser Ala Trp Leu Val Val
            340                 345                 350

Leu Pro Ala Glu Glu Leu Val Glu Ala Gly Glu Ala Gly Gly Val
        355                 360                 365

Phe Ala Gly Val Leu Ser Tyr Gly Leu Gly Phe Leu Leu Phe Ile Leu
    370                 375                 380

Ala Val Ala Ala Val Thr Leu Tyr Arg Leu Arg Ser Pro Pro Lys Lys
385                 390                 395                 400

Gly Leu Gly Ser Pro Ala Val His Lys Val Ser Arg Phe Pro Leu Lys
                405                 410                 415

Arg Gln Val Ser Leu Glu Ser Ser Ser Ser Met Ser Ser Asn Thr Pro
            420                 425                 430

Leu Val Arg Ile Ala Arg Leu Ser Ser Gly Glu Gly Pro Thr Leu Ala
        435                 440                 445

Asn Val Ser Glu Leu Glu Leu Pro Ala Asp Pro Lys Trp Glu Leu Ser
    450                 455                 460

Arg Ala Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Ala Ala
                485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
        515                 520                 525

Gly Lys His Lys Asn Ile Ile Asn Leu Leu Gly Ala Cys Thr Gln Gly
    530                 535                 540

Gly Pro Leu Tyr Val Leu Val Glu Tyr Ala Ala Lys Gly Asn Leu Arg
545                 550                 555                 560

Glu Tyr Leu Arg Ala Arg Arg Pro Pro Gly Thr Asp Tyr Ser Phe Asp
                565                 570                 575

Thr Cys Arg Leu Pro Glu Glu Gln Leu Thr Phe Lys Asp Leu Val Ser
            580                 585                 590

Cys Ala Tyr Gln Val Ala Arg Gly Met Glu Tyr Leu Ala Ser Gln Lys

```
                    595                 600                 605
Cys Ile His Arg Asp Leu Ala Ala Arg Asn Val Leu Thr Glu Asp
    610                 615                 620

Asn Val Met Lys Ile Ala Asp Phe Gly Leu Ala Arg Asp Val His Asn
625                 630                 635                 640

Leu Asp Tyr Tyr Lys Thr Thr Asn Gly Arg Leu Pro Val Lys Trp
                645                 650                 655

Met Ala Pro Glu Ala Leu Phe Asp Arg Val Tyr Thr His Gln Ser Asp
            660                 665                 670

Val Trp Ser Phe Gly Val Leu Leu Trp Glu Ile Phe Thr Leu Gly Gly
        675                 680                 685

Ser Pro Tyr Pro Gly Ile Pro Val Glu Glu Leu Phe Lys Leu Leu Lys
690                 695                 700

Glu Gly His Arg Met Asp Lys Pro Ala Asn Cys Thr His Asp Leu Tyr
705                 710                 715                 720

Met Ile Met Arg Glu Cys Trp His Ala Ala Pro Ser Gln Arg Pro Thr
                725                 730                 735

Phe Lys Gln Leu Val Glu Asp Leu Asp Arg Val Leu Thr Val Thr Ser
            740                 745                 750

Thr Asp Glu Tyr Leu Asp Leu Ser Val Pro Phe Glu Gln Tyr Ser Pro
        755                 760                 765

Gly Gly Gln Asp Thr Pro Ser Ser Gly Ser Ser Gly Asp Asp Ser Val
770                 775                 780

Phe Ala His Asp Leu Leu Pro Pro Ala Pro Ser Gly Ser Gly Gly Ser
785                 790                 795                 800

Arg Thr

<210> SEQ ID NO 18
<211> LENGTH: 2562
<212> TYPE: DNA
<213> ORGANISM: Bos taurus

<400> SEQUENCE: 18
ggccatgggg ggcagcatgc tggcgcgcgc cgcctgagga cgccgcaccc cccgcccccg      60
cgatgggcgc cccggctcgc gccctcgcgt tttgcgtggc agtggcggtc atgaccggcg     120
ccgcccctcgg gtccccgggc gtggagcccc cgtcgcgcg gagagcggca gaggtccccgg    180
gccccgagcc cagcccgcag agcgggcct ttggcagcgg ggacaccgtg agctgagct       240
gccgcttgcc ggcgggggtg cccacagagc ccaccgtctg ggtgaaggac ggcgtggggcc    300
tggcgccctc ggaccgcgtc ctggtggggc gcagcggct acaggtgctc aacgcctccc      360
acgaggacgc cggagcctac agctgccgcc agcgcctctc ccagcggctg ctgtgcctct     420
tcagcgtgcg cgtgacagat gctccgtcct caggggatga cgagggtggg gacgacgagg    480
ccgaggacac agctgggggcc ccttactgga cgcggcctga cgggatggac aagaagctgc    540
tagcggtgcc ggccgccaac acggttcgct tccgctgccc agctgctggc aaccccacgc    600
catccatcac ctggctgaag aacggcaagg agttccgggg cgagcaccgc atcggggaa     660
tcaaactgcg gcagcagcag tggagcctgg tcatggagag cgtggtgccc tcggaccgcg    720
gcaactacac gtgcgtcgtg gagaacaagt tcggcagaat ccagcagacc tacaccctgg    780
acgtgctgga cgctctccg caccggccca tcctacagge cgggctgccc gctaaccaga    840
cagccgtgct gggcagcgat gtggagttcc actgcaaggt ctacagcgac gcccagcccc    900
acatccagtg gctcaagcac gtggaggtga acggcagcaa ggtgggggcc cacggcacgc    960
```

```
cctacgtcac cgtgctcaag acggcgggcg ctaacaccac cgacaaggag ctagaggttc    1020
tatccttgcg caatgtcacc tttgaggacg cggggggagta cacatgtctg gcgggcaatt    1080
ctatcgggtt ttcccatcac tctgcgtggc tggtggtgct gccagctgag gaggagctgg    1140
tggaagccgg tgaggctggc ggtgtgttcg cgggtgtcct cagctacggg ctgggcttcc    1200
tcctcttcat cctggccgtg gccgccgtta cgctctaccg cctgaggagc ccccctaaga    1260
agggcctggg ctcgcccgcg gtgcacaagg tctcccgctt cccgctcaag cgacaggtgt    1320
ccttggagtc cagctcatcc atgagctcca acacaccgct ggtacgcatt gcccggctgt    1380
catcgggcga gggccccacc ctggccaacg tctctgagct cgagctgccc gccgacccca    1440
agtgggagct gtcccgggcc cggctgaccc tgggcaagcc tcttggggag gctgcttcg     1500 gccaggtggt catggcagag gccattggca tcgacaagga ccgagctgcc aagcctgtca    1560
cggtggccgt gaagatgctg aaagatgacg ccacggataa ggacttatcg acctggtgt     1620 ccgagatgga gatgatgaag atgatcggaa aacacaagaa cattatcaac ctgctaggcg    1680
cctgcacgca gggcgggccc ctgtacgtgc tggtggagta cgcggccaag ggcaacctgc    1740
gggaatacct gcgggcacgg cggccccccgg gcactgacta ctccttcgac acctgccggc    1800
tgcccgagga gcagctcacc ttcaaagacc tggtgtcctg cgcctaccag gtggcgcggg    1860
gcatggagta cctggcctcg cagaagtgca tccacaggga cctggcggcc cgcaacgtgc    1920
tggtgactga ggacaacgtg atgaaaatcg ccgacttcgg cctggctcgt gacgtgcaca    1980
acctcgacta ctacaaaaag accacaaacg gccgcctgcc cgtgaagtgg atggcacccg    2040
aggccttgtt tgaccgcgtc tacacccacc aaagtgacgt ctggtccttc ggggtcctgc    2100
tctgggagat cttcacgctg ggggctcgc cgtaccccgg catccccgtg gaggagctct    2160
tcaagctgct gaaggaaggc caccgcatgg acaagccggc caactgcacg catgacctgt    2220
acatgatcat gcgcgagtgc tggcacgccg cgccctcgca gaggcccacc ttcaagcagc    2280
tggtggagga cctggaccgt gtgctcaccg tgacgtccac cgacgagtac ctggacctgt    2340
cggtgccctt cgagcagtac tcgccgggcg gccaggacac ccccagctcc ggctcctcgg    2400
gggacgactc cgtgttcgct cacgacctgc tgccccggc cccatccggc agcggaggct    2460
cgcggacgtg aagggccgcg gccagccggc cgagccccca tcaatgtgag aacagacccc    2520
agcccaccat gctgccgctg gcgtgccatg atcccttggt cc                        2562
```

<210> SEQ ID NO 19
<211> LENGTH: 800
<212> TYPE: PRT
<213> ORGANISM: Bos taurus

<400> SEQUENCE: 19

```
Met Arg Leu Leu Leu Val Leu Leu Gly Val Leu Leu Gly Ala Pro Gly
1               5                   10                  15

Ala Pro Ala Leu Ser Phe Glu Ala Ser Glu Glu Thr Glu Leu Glu Pro
            20                  25                  30

Cys Leu Ala Pro Ser Pro Glu Gln Gln Glu Gln Glu Leu Thr Val Ala
        35                  40                  45

Leu Gly Gln Pro Val Arg Leu Cys Cys Gly Arg Ala Glu Arg Ser Gly
    50                  55                  60

His Trp Tyr Lys Glu Gly Ser Arg Leu Thr Pro Ala Gly Arg Val Arg
65                  70                  75                  80

Gly Trp Arg Gly Arg Leu Glu Ile Ala Ser Phe Leu Pro Glu Asp Ala
```

```
                    85                  90                  95
Gly Gln Tyr Leu Cys Leu Ser Arg Gly Ser Leu Leu His Asn Val
                100                 105                 110

Thr Leu Val Val Asp Asp Ser Met Thr Ser Ser Asn Gly Asp Glu Asp
            115                 120                 125

Pro Lys Ile His Arg Gly Pro Leu Asn Gly His Val Tyr Pro Gln Gln
        130                 135                 140

Ala Pro Tyr Trp Thr His Pro Gln Arg Met Glu Lys Lys Leu His Ala
145                 150                 155                 160

Val Pro Ala Gly Asn Thr Val Lys Phe Arg Cys Pro Ala Ala Gly Asn
                165                 170                 175

Pro Met Pro Thr Ile Arg Trp Leu Lys Asp Gly Gln Asp Phe His Gly
            180                 185                 190

Glu His Arg Ile Gly Gly Ile Arg Leu Arg His Gln His Trp Ser Leu
        195                 200                 205

Val Met Glu Ser Val Val Pro Ser Asp Arg Gly Thr Tyr Thr Cys Leu
210                 215                 220

Val Glu Asn Ser Leu Gly Ser Ile Arg Tyr Ser Tyr Leu Leu Asp Val
225                 230                 235                 240

Leu Glu Arg Ser Pro His Arg Pro Ile Leu Gln Ala Gly Leu Pro Ala
                245                 250                 255

Asn Thr Thr Ala Val Val Gly Ser Asp Val Glu Leu Leu Cys Lys Val
            260                 265                 270

Tyr Ser Asp Ala Gln Pro His Ile Gln Trp Leu Lys His Ile Val Ile
        275                 280                 285

Asn Gly Ser Ser Phe Gly Ala Asp Gly Phe Pro Tyr Val Gln Val Leu
        290                 295                 300

Lys Thr Ala Asp Ile Asn Ser Ser Glu Val Glu Val Leu Tyr Leu Arg
305                 310                 315                 320

Asn Val Ser Ala Glu Asp Ala Gly Glu Tyr Thr Cys Leu Ala Gly Asn
                325                 330                 335

Ser Ile Gly Leu Ser Tyr Gln Ser Ala Trp Leu Thr Val Leu Pro Glu
            340                 345                 350

Glu Asp Leu Thr Trp Thr Ala Thr Ala Pro Glu Gly Arg Tyr Thr Asp
        355                 360                 365

Ile Ile Leu Tyr Ser Ser Gly Ser Leu Ala Leu Ile Val Phe Leu Leu
        370                 375                 380

Leu Val Gly Leu Tyr Arg Arg Gln Thr Leu Leu Thr Arg His His Arg
385                 390                 395                 400

Gln Pro Ala Thr Val Gln Lys Leu Ser Arg Phe Pro Leu Ala Arg Gln
                405                 410                 415

Phe Ser Leu Glu Ser Gly Ser Ser Ala Lys Ser Ser Leu Ser Leu Val
            420                 425                 430

Arg Gly Val Arg Leu Ser Ser Ser Gly Pro Pro Leu Leu Ala Gly Leu
        435                 440                 445

Val Ser Leu Asp Leu Pro Leu Asp Pro Leu Trp Glu Phe Pro Arg Asp
        450                 455                 460

Arg Leu Val Leu Gly Lys Pro Leu Gly Glu Gly Cys Phe Gly Gln Val
465                 470                 475                 480

Val Cys Ala Glu Ala Phe Gly Met Asp Pro Thr Arg Pro Asp Gln Ala
                485                 490                 495

Ser Thr Val Ala Val Lys Met Leu Lys Asp Asn Ala Ser Asp Lys Asp
            500                 505                 510
```

```
Leu Ala Asp Leu Val Ser Glu Met Glu Val Met Lys Leu Ile Gly Arg
            515                 520                 525

His Lys Asn Ile Ile Asn Leu Leu Gly Val Cys Thr Gln Glu Gly Pro
        530                 535                 540

Leu Tyr Val Ile Val Glu Cys Ala Ala Lys Gly Asn Leu Arg Glu Phe
545                 550                 555                 560

Leu Arg Ala Arg Arg Pro Pro Gly Pro Asp Leu Ser Pro Asp Gly Pro
                565                 570                 575

Arg Ser Ser Glu Gly Pro Leu Ser Phe Pro Ala Leu Val Ser Cys Ala
            580                 585                 590

Tyr Gln Val Ala Arg Gly Met Gln Tyr Leu Glu Ser Arg Lys Cys Ile
            595                 600                 605

His Arg Asp Leu Ala Ala Arg Asn Val Leu Val Thr Glu Asp Asn Val
        610                 615                 620

Met Lys Ile Ala Asp Phe Gly Leu Ala Arg Gly Ile His His Ile Asp
625                 630                 635                 640

Tyr Tyr Lys Lys Thr Ser Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Ile Leu Leu Trp Glu Ile Phe Thr Leu Gly Gly Ser Pro
            675                 680                 685

Tyr Pro Gly Ile Pro Val Glu Glu Leu Phe Ser Leu Leu Arg Glu Gly
            690                 695                 700

His Arg Met Asp Arg Pro Pro His Cys Pro Pro Glu Leu Tyr Gly Leu
705                 710                 715                 720

Met Arg Glu Cys Trp His Ala Ala Pro Ser Gln Arg Pro Thr Phe Lys
                725                 730                 735

Gln Leu Val Glu Ala Leu Asp Lys Val Leu Leu Ala Val Ser Glu Glu
            740                 745                 750

Tyr Leu Asp Leu Arg Leu Thr Phe Gly Pro Tyr Ser Pro Ala Gly Gly
            755                 760                 765

Asp Ala Ser Ser Thr Cys Ser Ser Asp Ser Val Phe Ser His Asp Pro
        770                 775                 780

Pro Leu Pro Leu Arg Pro Ser Ser Phe Ser Phe Pro Gly Val Gln Thr
785                 790                 795                 800

<210> SEQ ID NO 20
<211> LENGTH: 3139
<212> TYPE: DNA
<213> ORGANISM: Bos taurus

<400> SEQUENCE: 20
attcctggct ctgcggccgg gggctgcgca actcccgagc agtcttctgt ctccgctggg      60
cgtgggggtc cgggctggcg ggagctgaga gcgaggccgc ggaggaccca gaaaggcagt    120
cataggaggc ccagcctggg tcctcgagag cggcaggaag gagatgcggc tgctgttggt    180
cctcctgggg gtcctgctgg gggcacctgg ggctccagct ttgtcctttg aggcctctga    240
ggaaacggag ctggagccct gcctggcccc cagcccggag cagcaagagc aggagttgac    300
ggtggccctt gggcagcctg tgcggttatg ctgcgggcgg gctgagcgca gtggccactg    360
gtacaaggag ggcagtcgcc tgacacctgc tggccgggta cgaggctgga gaggccgctt    420
ggagattgcc agcttcctac ccgaggatgc tggccagtac ctctgcctat acgaggctc    480
```

```
cttgcttctg cacaacgtca ccttggttgt ggacgactcc atgacctcca gcaatggcga    540
cgaggacccc aagatccaca ggggcccctt gaatgggcac gtttacccc agcaagcacc     600 ctactggacg cacccccagc gcatggagaa gaaactgcat gctgtgcctg ccgggaacac    660
cgtcaagttc cgctgtccag ctgcaggcaa ccccatgccc accatccgct ggctcaagga    720
tggacaggac ttccacgggg agcatcgcat tggaggcatt cggctgcgcc accagcactg    780
gagcctggtg atggaaagcg tggtgccctc tgaccgtggc acttacacct gcctcgtgga    840
gaattctttg ggcagcattc gctatagcta cctgctggac gtgctggagc ggtccccgca    900
ccggcccatc cttcaggcag ggctcccagc caacaccacg gctgtggtgg gcagtgacgt    960
ggaactgctc tgcaaggtgt acagcgacgc ccagccccac atccagtggc tgaagcacat    1020
cgtcatcaac ggcagcagct tcggtgccga cggcttcccc tatgtgcaag tcttaaagac    1080
agcggacatc aatagctcag aggtggaggt cttgtacctt cggaatgtat ctgctgagga    1140
tgcaggcgag tacacctgcc tggcgggcaa ctccatcggc cttcctacc agtcggcctg     1200 gctcacggtg ctgccagagg aggatctcac gtggacagcg acagcacccg aaggcaggta    1260
cacggacatc atcctgtact cgtcaggctc tctggctttg atcgtgttcc tgctgctggt    1320
cgggctatat cgcaggcaga cgctcctcac ccgacaccac cgacagcccg ccaccgtgca    1380
gaagttgtct cgctttcctc tggcccgaca gttctcgctg gagtcaggct cctcagccaa    1440
gtcaagcttg ccctggtgc ggggtgtccg tctctcctcc agcggccccc ccttgctcgc     1500
tggcctcgtg agtctcgacc tgcctcttga cccactgtgg gagttcccc gggacaggct     1560 ggtgctggga aagcccctgg gcgagggctg ctttgggcag gtggtgtgcg cagaggcctt    1620
cggcatggac cccacccggc cagaccaagc cagcaccgtg gctgtcaaga tgcttaagga    1680
caacgcctcc gacaaggact tggcagacct ggtctctgag atggaggtga tgaagctgat    1740
tggccgacac aagaacatta tcaacctgct gggtgtctgc acccaggaag ggcccttgta    1800
cgtgatcgtg gagtgtgctg ccaagggcaa cctgcgggag ttcctgcggg cccgccgccc    1860
cccaggccct gacctcagcc ctgacgggcc tcggagcagc gaggggccgc tctccttccc    1920
tgccctggtc tcctgcgcct accaggtggc cggggcatg cagtacctgg agtcccggaa     1980
gtgcatccac cgggacctgg ctgcccgcaa tgtactggtg accgaggaca atgtgatgaa    2040
gattgcagac ttcgggctgg cccgtggcat ccaccacatt gactactaca agaaaactag    2100
caacggccgc ctgcctgtca gtggatggc accagaggcc ttgtttgaca gagtctacac      2160
acaccagagt gatgtgtggt cgtttggaat cctgctgtgg gagatcttca ccctcggggg    2220
ctccccatac cctggcatcc ccgtggagga gctgttctcg ctgctacgag aggggcatcg    2280
gatggaccgg ccccccacact gcccccagaa gctatacggg ctgatgcgcg agtgctggca    2340
cgcagcaccc tctcagaggc ccactttcaa gcaactggta gaggcactgg acaaggtcct    2400
gctggccgtc tctgaggagt acctcgacct ccgcctaacc tttggaccct actcccctgc    2460
cggcggggac gccagcagca cctgctcctc tagcgactct gtcttcagcc acgacccct     2520 accactgagg cccagctcct tctccttccc tggggtgcag acgtgagcag aggcacaggc    2580
tgtatgggca gggtcagctg ccagccttgg gcctcctggc tcaactgaaa ccaggtggca    2640
ctcgtccttg gcagccccag gccctgacct aagggtacta tcccagatct ctggttctgt    2700
ttgggggagg tctgtccttg gtcctggggt ccctagtctc gagacttcct tctctggcct    2760
ctgggtctca agccagagtt caatcccagc ctcaaggccc tgttctttgg agtcgtggcc    2820
ccagtgttct aatggcttgt taaggttctg cttggacttc tgggccttgg tagaagtcct    2880
```

```
tgttccaggg ctttggttgg acctggctgc agggctgtct taaacctccc cgcttcccca    2940
taccaagaga ggtcttagac ctctgaaccc cacttcccca ggcctcccct gcctccctct    3000
gctgcttgtc ccagcatctt gatggaagga gcgcttgtgc ccaccccatc cccacaccgc    3060
cccgtgctgg ctgagaggct gggagcctac caaaacacag aagcaaatga cctttttataa   3120 attattttt tgaaatgaa                                                  3139
```

<210> SEQ ID NO 21
<211> LENGTH: 114
<212> TYPE: PRT
<213> ORGANISM: Sus scrofa

<400> SEQUENCE: 21

```
Met Ser Leu Ile Phe Phe Thr Leu Tyr Ile Val Ile Phe Ser Leu Leu
1               5                   10                  15

Leu Ile Val Lys Leu Gln Leu Gln Ala Glu Glu Arg Gly Val Val Ser
            20                  25                  30

Ile Lys Gly Val Cys Ala Asn Arg Tyr Leu Ala Met Lys Glu Asp Gly
        35                  40                  45

Arg Leu Leu Ala Ser Lys Cys Val Thr Asp Glu Cys Phe Phe Phe Glu
    50                  55                  60

Arg Leu Glu Ser Asn Asn Tyr Asn Thr Tyr Arg Ser Arg Lys Tyr Ser
65                  70                  75                  80

Ser Trp Tyr Val Ala Leu Lys Arg Thr Gly Gln Tyr Lys Leu Gly Pro
                85                  90                  95

Lys Thr Gly Pro Gly Gln Lys Ala Ile Leu Phe Leu Pro Met Ser Ala
            100                 105                 110

Lys Ser
```

<210> SEQ ID NO 22
<211> LENGTH: 345
<212> TYPE: DNA
<213> ORGANISM: Sus scrofa

<400> SEQUENCE: 22

```
atgtctctta tcttctttac cctgtatatt gtaattttt cttattact tatagtcaaa      60 ctacaacttc aagcagaaga gagggggtt gtgtctatca aaggagtgtg tgcaaaccgt    120
tatcttgcta tgaaggaaga tggaagatta ctggcttcta aatgtgttac agacgagtgt    180 ttctttttg aacgactgga atctaataac tacaatactt accggtcgag gaaatactcc    240
agttggtatg tggcactgaa acgaacgggg cagtataaac ttggacccaa aacaggacct    300
gggcagaaag ctatactttt tcttccaatg tctgctaaga gctga                   345
```

<210> SEQ ID NO 23
<211> LENGTH: 818
<212> TYPE: PRT
<213> ORGANISM: Sus scrofa

<400> SEQUENCE: 23

```
Met Cys Ser Trp Lys Cys Leu Leu Phe Trp Ala Val Leu Val Thr Ala
1               5                   10                  15

Thr Leu Cys Thr Ala Arg Pro Ala Pro Thr Ser Pro Glu Gln Ala Gln
            20                  25                  30

Pro Trp Gly Ala Pro Val Glu Val Glu Ser Phe Leu Val His Pro Gly
        35                  40                  45
```

```
Asp Leu Leu Gln Leu Arg Cys Arg Leu Arg Asp Asp Val Gln Ser Ile
 50                  55                  60
Asn Trp Leu Arg Asp Gly Val Gln Leu Val Glu Ser Asn Arg Thr Arg
 65                  70                  75                  80
Ile Thr Gly Glu Glu Val Glu Val Arg Asp Ser Val Pro Ser Asp Ser
                 85                  90                  95
Gly Leu Tyr Ala Cys Val Thr Ser Ser Pro Ser Gly Ser Asp Thr Thr
            100                 105                 110
Tyr Phe Ser Val Asn Val Ser Asp Ala Leu Pro Ser Ser Glu Asp Asp
            115                 120                 125
Asp Asp Asp Asp Asp Ser Ser Ser Glu Glu Lys Glu Thr Asp Asn Thr
130                 135                 140
Lys Pro Asn Pro Val Ala Pro Tyr Trp Thr Ser Pro Glu Lys Met Glu
145                 150                 155                 160
Lys Lys Leu His Ala Val Pro Ala Ala Lys Thr Val Lys Phe Lys Cys
                165                 170                 175
Pro Ser Ser Gly Thr Pro Asn Pro Thr Leu Arg Trp Leu Lys Asn Gly
            180                 185                 190
Lys Glu Phe Lys Pro Asp His Arg Ile Gly Gly Tyr Lys Val Arg Tyr
            195                 200                 205
Ala Thr Trp Ser Ile Ile Met Asp Ser Val Val Pro Ser Asp Lys Gly
210                 215                 220
Asn Tyr Thr Cys Val Val Glu Asn Glu Tyr Gly Ser Ile Asn His Thr
225                 230                 235                 240
Tyr Gln Leu Asp Val Val Glu Arg Ser Pro His Arg Pro Ile Leu Gln
                245                 250                 255
Ala Gly Leu Pro Ala Asn Lys Thr Val Ala Leu Gly Ser Asn Val Glu
            260                 265                 270
Phe Met Cys Lys Val Tyr Ser Asp Pro Gln Pro His Ile Gln Trp Leu
            275                 280                 285
Lys His Ile Glu Val Asn Gly Ser Lys Ile Gly Pro Asp Asn Leu Pro
290                 295                 300
Tyr Val Gln Ile Leu Lys Thr Ala Gly Val Asn Thr Thr Asp Lys Glu
305                 310                 315                 320
Met Glu Val Leu His Leu Arg Asn Val Ser Phe Glu Asp Ala Gly Glu
                325                 330                 335
Tyr Thr Cys Leu Ala Gly Asn Ser Ile Gly Leu Ser His His Ser Ala
            340                 345                 350
Trp Leu Thr Val Leu Glu Ala Leu Glu Glu Arg Pro Ala Val Met Thr
            355                 360                 365
Ser Pro Leu Tyr Leu Glu Ile Ile Ile Tyr Cys Thr Gly Ala Phe Leu
370                 375                 380
Ile Ser Cys Met Val Gly Ser Val Ile Ile Tyr Lys Met Lys Ser Gly
385                 390                 395                 400
Thr Lys Lys Ser Asp Phe His Ser Gln Met Ala Val His Lys Leu Ala
                405                 410                 415
Lys Ser Ile Pro Leu Arg Arg Gln Val Ser Ala Asp Ser Ser Ala Ser
            420                 425                 430
Met Asn Ser Gly Val Leu Leu Val Arg Pro Ser Arg Leu Ser Ser Ser
            435                 440                 445
Gly Thr Pro Met Leu Ala Gly Val Ser Glu Tyr Glu Leu Pro Glu Asp
450                 455                 460
Pro Arg Trp Glu Leu Pro Arg Asp Arg Leu Val Leu Gly Lys Pro Leu
```

```
            465                 470                 475                 480
Gly Glu Gly Cys Phe Gly Gln Val Val Leu Ala Glu Ala Ile Gly Leu
                485                 490                 495

Asp Lys Asp Lys Pro Asn Arg Val Thr Lys Val Ala Val Lys Met Leu
                500                 505                 510

Lys Ser Asp Ala Thr Glu Lys Asp Leu Ser Asp Leu Ile Ser Glu Met
                515                 520                 525

Glu Met Met Lys Met Ile Gly Lys His Lys Asn Ile Ile Asn Leu Leu
            530                 535                 540

Gly Ala Cys Thr Gln Asp Gly Pro Leu Tyr Val Ile Val Glu Tyr Ala
545                 550                 555                 560

Ser Lys Gly Asn Leu Arg Glu Tyr Leu Gln Ala Arg Arg Pro Pro Gly
                565                 570                 575

Leu Glu Tyr Cys Tyr Asn Pro Ser His Asn Pro Glu Glu Gln Leu Ser
                580                 585                 590

Ser Lys Asp Leu Val Ser Cys Ala Tyr Gln Val Ala Arg Gly Met Glu
                595                 600                 605

Tyr Leu Ala Ser Lys Lys Cys Ile His Arg Asp Leu Ala Ala Arg Asn
            610                 615                 620

Val Leu Val Thr Glu Asp Asn Val Met Lys Ile Ala Asp Phe Gly Leu
625                 630                 635                 640

Ala Arg Asp Ile His His Ile Asp Tyr Tyr Lys Lys Thr Thr Asn Gly
                645                 650                 655

Arg Leu Pro Val Lys Trp Met Ala Pro Glu Ala Leu Phe Asp Arg Ile
                660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Val Pro Val Glu Glu
            690                 695                 700

Leu Phe Lys Leu Leu Lys Glu Gly His Arg Met Asp Lys Pro Ser Asn
705                 710                 715                 720

Cys Thr His Glu Leu Tyr Met Met Arg Asp Cys Trp His Ala Val
                725                 730                 735

Pro Ser Gln Arg Pro Thr Phe Lys Gln Leu Val Glu Asp Leu Asp Arg
                740                 745                 750

Ile Val Ala Leu Thr Ser Asn Gln Glu Tyr Leu Asp Leu Ser Met Pro
                755                 760                 765

Leu Asp Gln Tyr Ser Pro Ser Phe Pro Asp Thr Arg Ser Ser Thr Cys
            770                 775                 780

Ser Ser Gly Glu Asp Ser Val Phe Ser His Glu Pro Leu Pro Glu Glu
785                 790                 795                 800

Pro Cys Leu Pro Arg His Pro Pro Gln Leu Ala Asn Gly Gly Leu Lys
                805                 810                 815

Arg Arg

<210> SEQ ID NO 24
<211> LENGTH: 3974
<212> TYPE: DNA
<213> ORGANISM: Sus scrofa

<400> SEQUENCE: 24
cggggctatc gcggccccgc caggaccgga gcggagcccg ggggcggcgg gccggagccg      60
aggacgcggg cgcccgcccg cccgcacaag ccacggcgga ctctccagag gcggaatcgc     120
```

```
cgagcccagt gagagtcagc tcaccaacga ggatcaagcc cacagcagcg tctccatgga      180
ggtgtggagc ctggtcacca acctctaacc gcagaactgg gatgtgcagc tggaagtgcc      240
tcctcttctg ggctgtgctg gtcacagcca cgctctgcac ggccaggccg gctccgacct      300
cgccggaaca agctcagccc tggggagccc cgtggaagt  ggagtccttc ctggtccacc      360
ccggtgacct gctgcagctc cgctgtcggc tgcgggacga tgttcagagc atcaactggc      420
tgcgggacgg ggtgcagctg gtggaaagca accgcaccg  catcacaggg gaggaggtgg      480
aggtgcggga ctccgtgccc tccgactccg gcctctacgc ctgtgtgacc agcagcccct      540
cgggcagcga caccacctac ttctccgtca acgtctcaga tgctctcccc tcttcggagg      600
atgacgatga cgatgatgac tcctcctcag aggagaaaga gacagataac accaaaccaa      660
accccgtggc tccgtactgg acatcccag  agaagatgaa aaagaaattg catgcggtgc      720
cagctgccaa gacagtgaag ttcaagtgcc cctccagtgg gactcctaac cccaccttgc      780
gctggctgaa aaatggcaaa gaattcaagc ctgaccacag aatcggaggc tacaaggtcc      840
gttatgccac ctggagcatc atcatggact ccgtggtgcc ctccgacaag gcaactaca       900 cctgcgtcgt ggagaacgag tatggcagca tcaaccacac ctaccagctt gacgttgtgg      960
agcggtcccc tcaccggccc atcctgcagg cagggttgcc agccaacaag acagtggccc     1020
tgggcagcaa tgtggaattc atgtgcaagg tgtacagtga cccacagccc cacatccagt     1080
ggctaaagca catcgaggtg aatgggagta agattggtcc ggacaaccta ccttatgtcc     1140
agatcttgaa gactgccggc gttaatacca ccgacaaaga gatggaggtg ctccacttaa     1200
ggaatgtctc ctttgaggac gcgggggagt atacatgctt ggcgggtaac tctatcggac     1260
tctcccatca ctctgcatgg ttgaccgttc tggaagccct ggaagagcgc ccggcggtga     1320
tgacctcgcc cttgtacctg gagatcatca tctactgcac aggggccttc ctcatctcct     1380
gcatggtggg gtctgtcatc atctacaaga tgaagagtgg caccaagaag agtgacttcc     1440
acagccagat ggccgtgcac aagctggcca gagcatccc  tctgcgcaga caggtgtcag     1500
ctgactccag tgcctccatg aactctgggg tcctactggt tcggccgtcg cgtctctcct     1560
ccagtgggac cccatgctg  gctggggtct ccgaatacga gcttcctgaa gaccctcgct     1620
gggagctgcc tcgggacagg ctggttttag gcaaacccct gggagagggc tgctttgggc     1680
aggtggtgtt ggcagaggcc attgggctgg acaaggacaa gcccaaccgt gtgaccaaag     1740
tggctgtgaa gatgctgaag tcggatgcaa cagagaaaga cctgtcagac ctgatctctg     1800
agatggagat gatgaagatg attgggaagc acaagaacat catcaacctg ctgggggcct     1860
gcacgcagga cggacctctc tatgtcattg tggagtatgc ctccaagggc aacctccgtg     1920
agtacctgca ggcccggagg ccgcctggcc tggaatactg ctacaacccc agccacaacc     1980
cggaggagca gctctcctcc aaggacctgg tctcctgtgc ctatcaggtg gctcgaggca     2040
tggagtacct cgcttccaag aagtgcatac accgagacct ggccgccagg aacgtcctcg     2100
tgacggaaga caacgtgatg aagatcgcag actttggcct tgcccgggac atccaccaca     2160
ttgactacta caaaaagaca accaacggcc gactgccggt gaagtggatg gcaccggaag     2220 ctttgttt   ccggatctac acccaccaga gtgacgtgtg gtcttttggg gtgctcctgt     2280
gggaaatctt cactctgggc ggctccccat accctggcgt ccctgtggag gagctttca      2340 agctgttgaa ggagggtcat cggatggaca agcccagtaa ctgcacccat gaactataca     2400
tgatgatgcg agactgttgg cacgcggtac cctcccagag acctaccttc aagcagctgg     2460
tggaagacct ggaccgcatt gtggccttga cctccaacca ggagtatctg gacctgtcga     2520
```

```
tgcccctgga ccagtactcc cccagcttcc ctgacacccg cagctctacc tgctcctctg    2580
gggaagattc cgtcttctct cacgaaccct gcccgagga gccctgcctg ccccgacacc    2640 cacccccagct tgccaacggc ggactcaaac ggcgctgacc ggcaccctgg caccccctccc   2700 caaactccat ccttagctgt gaccccctccc ccctcctgct ggactctgcc ccaccccgcc    2760
ccttcctgct ggcaggagcc agctgcctac ctggggcctt caccccccagt tcccctctcc    2820 acctccccct cctctcagcc tgctggtgcg acagaggaac agggaggcag gtacttgctg    2880
acggccactt tgttctctcc cagtgttgga ccaagacccc ctccccctca ccgggcactg    2940
cctggagggg tgggaagtgg gggatgagca gcactcgagc gactgagctt tccggtgttg    3000
gttttgtctg ctccatgcag cctgtccacc cgggttctgg tggcaggtcc ttgggctaca    3060
gcagtggttg gggcggggt cagtgcttgg gcctctgcgc cagatggatg gtgccaaggg    3120
cttcttaatt ccaatactaa tgtgctttgc tgaccaaata cctggtacca gaggatggag    3180
ttgcagaggc tggaagcagt gtggtggccc tggggcccag ccccaaacca ggggctttgt    3240
acatagctac gaagaaaaca caaagtgtat aaatctgagt atatatttac atgtcttttt    3300
aaaagggtcg ttaccagaga tttacccact ggggaagatg ctcctggtgg ctgggaggca    3360
tcggttgcta tatattaaaa acaaagaaaa agaaaaaaa aaaaggaaa atgttttaa    3420 aaaggtcata tattttttgc tactttttgct gttttatttt tttaaattat gttctaaacc    3480
tattttcagt ttaggtccct caataaaaat tgctgctgct tcattttat acgggctgtg    3540 tgacgcacac gggagaggat cttggccgca aaggagcaag cgggctctgg agctgtctgt    3600
ccagagtgcg tactatctgt ggtcccctcc cactcctcac cttatgtctc actcctaggc    3660
ctccgcacag accttgttgc ttttggaaag gcagggaaag aagatgagat gggcagggag    3720
cagaggcact gggcccaggg ccaggcttct cagccctcat ttccctgggg aagagaggag    3780 gaagggggatg gggggcagaa tggggtgtga gtgtcagaca gggagctgga ggcctggcct    3840
caaaagagcc aaggtgtagg agttcctgca gtggcacaac aggatcggtg gtgtcttggg    3900
tgtgctggga tgcagatttg atccctggcc cagcacagtg ggttaaggat ggggcgttgc    3960
cgcagctgtg actt                                                     3974
```

<210> SEQ ID NO 25
<211> LENGTH: 822
<212> TYPE: PRT
<213> ORGANISM: Sus scrofa

<400> SEQUENCE: 25

```
Met Val Ser Trp Gly Arg Phe Ile Cys Leu Val Val Thr Met Ala
1               5                   10                  15

Thr Leu Ser Leu Ala Arg Pro Ser Phe Asn Leu Val Glu Asp Thr Thr
                20                  25                  30

Val Glu Pro Glu Glu Pro Pro Thr Lys Tyr Gln Ile Ser Gln Pro Glu
            35                  40                  45

Val Tyr Val Ala Ala Pro Arg Glu Ser Leu Glu Leu Arg Cys Leu Leu
        50                  55                  60

Arg Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ala Arg Ser
            100                 105                 110
```

```
Val Asp Ser Glu Thr Val Tyr Phe Met Val Asn Val Thr Asp Ala Ile
            115                 120                 125

Ser Ser Gly Asp Asp Glu Asp Thr Asp Gly Ser Glu Asp Phe Val
        130                 135                 140

Ser Glu Asn Ser Asn Ser Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Ser Pro Thr Pro Thr Met Arg Trp Leu
            180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Asp Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Val Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Thr Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Glu Lys Pro Lys Glu Ala
            500                 505                 510

Val Thr Val Ala Val Lys Met Leu Lys Asp Asp Ala Thr Glu Lys Asp
        515                 520                 525
```

```
Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Val Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Asp Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Pro Tyr Pro Gln Arg
                805                 810                 815

Asn Gly Ser Val Asn Thr
            820
```

<210> SEQ ID NO 26
<211> LENGTH: 2738
<212> TYPE: DNA
<213> ORGANISM: Sus scrofa

<400> SEQUENCE: 26

```
tcgtccacat ggagatatgg aagaggacgg gggattggca gcgtaaccat ggtcagctgg      60
ggccgcttca tctgcctggt tgtggtcacc atggcaacct tgtctctggc ccggccctcc     120
ttcaatttag ttgaggatac cacggtggag ccggaagagc accaaccaa ataccaaatc      180 tcccaaccag aagtttacgt ggctgcgccc cgggagtcgc tagagttgcg ctgcctgttg     240
cgagatgccg ccgtgatcag ttggactaag gatggggtac acttggggcc caacaatagg     300
acagtgctta ttggggagta cttgcagata aaaggtgcca cgcctaggga ctccggcctc     360
tatgcttgta ccgctgctag gagtgtagac agtgagactg tctacttcat ggtcaatgtc     420
```

```
acagatgcca tctcgtccgg agatgacgag gacgacaccg atggctcaga ggattttgtc      480
agtgagaaca gtaacagcaa gagagccccg tactggacca acacagaaaa gatggaaaaa      540
cggctgcacg ctgtccctgc cgccaacact gtcaagttcc gctgtccagc tgggggtagt      600
ccaacaccaa cgatgaggtg gctgaaaaac gggaaggaat ttaagcagga acatcgcatt      660
ggaggctata aggtacgaaa ccagcactgg agcctcatta tggaaagcgt ggttccatcc      720
gacaaaggaa attatacctg cgtggtggag aacgattacg ggtccatcaa tcacacrtac      780
cacctcgacg tcgttgagcg atcgccgcac cggcccatcc tccaagccgg actgccggcc      840
aacgcctcca ccgtggttgg gggcgacgtg gagtttgtct gcaaggtgta cagtgatgcc      900
cagccccaca tccagtggat caaacacgtg gaaaagaacg gcagcaaata cgggcccgac      960
gggctgcctt acctcaaggt tctgaagcac tcagggataa atagttccaa tgcagaagtg     1020
ctggctctgt tcaatgtgac tgaggcggat gctggggagt atatttgtaa ggtctccaat     1080
tatatagggc aggccaacca gtctgcctgg ctcactgtcc tgccaaaaca gcaagctccc     1140
gtgagagaaa aggagatcac agcttcccca gactacctgg agatagccat ttactgcata     1200
ggggtcttcc tgatcgcctg catggtggtg acggtcattc tgtgccggat gaagaccacc     1260
accaagaagc cggacttcag cagccagccg gcagtgcaca gctgaccaa cgcatcccc      1320
ctgcggagac aggtaacagt ttctgccgag tccagctcct ccatgaactc caacacccca     1380
ctggtgagga ttacaactcg cctctcctcc acagcagaca cccccatgct ggcggggggtc     1440
tccgagtacg agctgccgga agatccaaag tgggagtttc ccagagataa gctgacgctg     1500
ggcaaacccc tgggagaagg ttgctttggg caagtggtca tggctgaagc ggtgggaatc     1560
gacaaagaga agcccaagga agcagtcact gtggccgtga agatgttgaa agatgatgcc     1620
acagagaaag acctttctga tctggtgtca gagatggaga tgatgaagat gattggcaaa     1680
cacaaaaata tcataaatct cctcggagcc tgtactcagg atgggccgct ctacgtcata     1740
gtcgagtacg cctcgaaagg caacctccga gagtacctgc gcgcccggcg gcctccgggg     1800
atggagtact cgtacgacgt caaccgcgtg cccgaggagc agatgaccct caaggacttg     1860
gtgtcctgca cctaccagct ggcccggggc atggagtact ggcctcccca aaaatgtatc     1920
catcgagatt tagccgccag aaatgttttg gtaacagaaa acaatgtgat gaaaatagcc     1980
gacttcggac tggccagaga tatcaacaat atagactatt acaaaaagac caccaatggc     2040
cggcttccgg tcaagtggat ggctccagag gcccttttg atcgcgtgta cacccaccag     2100
agtgatgtct ggtccttcgg ggtgttaatg tgggagatct tcacgttagg gggctcgccc     2160
tacccaggga ttcccgtgga ggaacttttt aagctgctca agaaggaca caggatggat     2220
aagccagcaa actgcaccaa cgaactgtat atgatgatga gagactgttg gcatgcggtg     2280
ccctcacaga gacccacctt caagcagttg gtagaagact tggatcgaat tctcacactc     2340
acgaccaatg aggactactt ggacctcagt cagcctctcg aacagtattc acctagttac     2400
cctgacacca ggagttcttg ctcttcggga gatgattctg tttctctcc ggaccccatg     2460
ccttatgaac cctgccttcc tccgtaccca cagagaaacg gcagtgttaa cacatgaacg     2520
ggcttgtccc cctgtcccca gacagggccg cgccggagc ctaggtgtac tgagcagggg     2580
aggccatgcc tcccgcagcc tgtatatatg gatcagagga gtaaataatt ggaaacgtgg     2640
atcggcagga gcctaggtgt actgagcagg ggaggccatg cctcccgcag cctgtatata     2700
tggatcagag gagtaaataa ttggaaacgt gatcggca                             2738
```

<210> SEQ ID NO 27
<211> LENGTH: 391
<212> TYPE: DNA
<213> ORGANISM: Sus scrofa

<400> SEQUENCE: 27

| | | | | | |
|---|---|---|---|---|---|
| gtcatcggat | ggacaagccc | agtaactgca | cccatgaact | gtaagcatga | ggagatgcct | 60 |
| ggggccctgg | gctcagccct | gggagggtgg | gggatgggct | ggacgrgtag | aggagggaag | 120 |
| grgtgctyag | ccagayaccg | gggacttcct | ggccacccct | cccacagtcc | tccggccctg | 180 |
| agccttttt | ttttaaaac | tcagtgaatt | ttattacatt | tatagttgta | caatgatcat | 240 |
| cacaaccta | agccttttt | tttttcatc | tgcttcttct | cttcctcccc | tgacttcacc | 300 |
| atcctgcccc | agatacatga | tgatgcgaga | ctgttggcac | gcggtaccct | cccagagacc | 360 |
| taccttcaag | cagctggtgg | aagacctgga | c | | | 391 |

<210> SEQ ID NO 28
<211> LENGTH: 800
<212> TYPE: PRT
<213> ORGANISM: Sus scrofa

<400> SEQUENCE: 28

```
Met Gln Leu Leu Leu Ala Leu Leu Gly Val Leu Ala Val Pro Gly
1               5                   10                  15

Ala Pro Ala Leu Ser Leu Glu Ala Ser Glu Glu Thr Glu Leu Glu Pro
            20                  25                  30

Cys Leu Ala Pro Ser Pro Glu Glu Gln Glu Arg Glu Leu Thr Val Val
        35                  40                  45

Leu Gly Gln Ser Val Arg Leu Cys Cys Gly Arg Ala Glu Arg Ser Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Phe Cys Leu Ala Arg Gly Ser Met Leu Val Leu His Asn
            100                 105                 110

Val Thr Leu Val Met Asp Asp Ser Met Ile Ser Ser Asn Gly Asp Glu
        115                 120                 125

Asp Pro Gly Thr His Ser Gly Pro Ser Asn Gly His Ile Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Met Pro Thr Ile Arg Trp Leu Lys Asp Gly Gln Asp Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ser Leu Gly Ser Ile Arg Tyr Ser Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270
```

```
Val Tyr Ser Asp Ala Gln Pro His Ile Gln Trp Leu Lys His Ile Val
    275                 280                 285
Ile Asn Gly Ser Ser Phe Gly Ala Asp Gly Phe Pro Tyr Val Gln Val
    290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
            340                 345                 350
Glu Glu Asp Leu Thr Trp Thr Ala Ala Gly Pro Glu Ala Arg Tyr Thr
        355                 360                 365
Asp Val Ile Leu Tyr Ala Ser Gly Ser Leu Ala Leu Leu Val Leu Leu
    370                 375                 380
Leu Leu Ala Gly Leu Tyr Arg Arg Gln Val Leu His Gly Arg His Pro
385                 390                 395                 400
Arg Gln Pro Ala Thr Val Gln Lys Leu Ser Arg Phe Pro Leu Ala Arg
                405                 410                 415
Gln Phe Ser Leu Glu Ser Gly Ser Ser Ala Lys Ser Ser Ser Ser Leu
            420                 425                 430
Val Arg Gly Val Arg Leu Ser Ser Ser Gly Pro Pro Leu Leu Ala Gly
        435                 440                 445
Leu Val Ser Leu Asp Leu Pro Leu Asp Pro Leu Trp Glu Phe Pro Arg
    450                 455                 460
Asp Arg Leu Val Leu Gly Lys Pro Leu Gly Glu Gly Cys Phe Gly Gln
465                 470                 475                 480
Val Val Cys Ala Glu Ala Phe Gly Met Asp Pro Thr Arg Pro Asp Gln
                485                 490                 495
Ala Ser Thr Val Ala Val Lys Met Leu Lys Asp Asn Ala Ser Asp Lys
            500                 505                 510
Asp Leu Ala Asp Leu Val Ser Glu Met Glu Val Met Lys Leu Ile Gly
        515                 520                 525
Arg His Lys Asn Ile Ile Asn Leu Leu Gly Val Cys Thr Gln Glu Gly
    530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Arg Ser Ser Glu Gly Pro Leu Ser Phe Pro Ala Leu Val Ser Cys
            580                 585                 590
Ala Tyr Gln Val Ala Arg Gly Met Gln Tyr Leu Glu Ser Gln Lys Cys
        595                 600                 605
Ile His Arg Asp Leu Ala Ala Arg Asn Val Leu Val Thr Glu Asp Asn
    610                 615                 620
Val Met Lys Ile Ala Asp Phe Gly Leu Ala Arg Gly Ile His His Ile
625                 630                 635                 640
Asp Tyr Tyr Lys Lys Thr Ser Asn Gly Arg Leu Pro Val Lys Trp Met
                645                 650                 655
Ala Pro Glu Ala Leu Phe Asp Arg Val Tyr Thr His Gln Ser Asp Val
            660                 665                 670
Trp Ser Phe Gly Ile Leu Leu Trp Glu Ile Phe Thr Leu Gly Gly Ser
        675                 680                 685
```

| | | | | | | | | | | | | | | |
|---|---|---|---|---|---|---|---|---|---|---|---|---|---|---|
|Pro|Tyr|Pro|Gly|Ile|Pro|Val|Glu|Glu|Leu|Phe|Ser|Leu|Leu|Arg|Glu|
| |690| | | |695| | | |700| | | | | |
|Gly|His|Arg|Met|Asp|Arg|Pro|His|Cys|Pro|Pro|Glu|Leu|Tyr|Gly|
|705| | | |710| | | |715| | | |720| | |
|Leu|Met|Arg|Glu|Cys|Trp|His|Ala|Ala|Pro|Ser|Gln|Arg|Pro|Thr|Phe|
| | | | |725| | | |730| | | |735| | |
|Lys|Gln|Leu|Val|Glu|Ala|Leu|Asp|Lys|Val|Leu|Leu|Ala|Val|Ser|Glu|
| | | |740| | | |745| | | |750| | | |
|Glu|Tyr|Leu|Asp|Leu|Arg|Leu|Thr|Phe|Gly|Pro|Tyr|Ser|Pro|Ala|Gly|
| | |755| | | |760| | | |765| | | | |
|Gly|Asp|Ala|Ser|Ser|Ser|Cys|Ser|Ser|Ser|Asp|Ser|Val|Phe|Ser|His|
| |770| | | |775| | | |780| | | | | |
|Glu|Pro|Leu|Pro|Leu|Gly|Pro|Ser|Ser|Phe|Phe|Pro|Gly|Val|Gln|Thr|
|785| | | |790| | | |795| | | |800| | |

<210> SEQ ID NO 29
<211> LENGTH: 2820
<212> TYPE: DNA
<213> ORGANISM: Sus scrofa

<400> SEQUENCE: 29

| | | |
|---|---|---:|
|atgcagctgc tgctggccct gttggggtc ctgctggcag tgcctggggc tccagctttg|  |60|
|tctcttgagg cctctgagga aacggagctg gagccctgcc tggcccccag cccgaggag|  |120|
|caagagcggg agctgactgt ggtccttggg cagtctgtgc ggttatgctg tgggcgggct|  |180|
|gaacgtagtg ccactggta caaggagggt agtcgcctgg cacctgctgg ccgagtacga|  |240|
|ggctggagag gccgcttgga gattgccagc ttcctacccg aggatgctgg ccgatacttc|  |300|
|tgcctggcac gaggctccat gcttgtcctg cacaatgtca ccttggttat ggatgactcc|  |360|
|atgatctcca gcaacggtga tgaggacccc gggacccaca gtggcccctc gaatgggcac|  |420|
|atttaccccc agcaagcacc ctactggaca caccccagc gcatggagaa gaaactgcat|  |480|
|gcagtgcctg ctgggaacac tgtcaagttt cgctgtccag cggcaggcaa ccccatgccc|  |540|
|accatccgct ggcttaagga tggacaggac ttccatgggg agaatcgcat tggaggcatt|  |600|
|aggctgcgcc accagcactg gagcctggtg atggaaagcg tggtgccatc ggaccgtggc|  |660|
|acatacacct gcctcgtgga gaactctttg ggcagcatcc gctacagcta tctgctggat|  |720|
|gtactggagc ggtccccgca ccggcccatc ctgcaggcgg gctcccagc caataccaca|  |780|
|gccgtggtgg gcagcgacgt ggagctgtta tgcaaggtgt acagcgatgc ccagcctcac|  |840|
|atccagtggc tgaagcacat tgtcatcaac ggcagcagct ttggtgccga cggcttcccc|  |900|
|tatgtgcaag tcttaaagac agcagacatc aatagctcag aggtggaggt cctataccct|  |960|
|cggaatgtgt ctgccgagga cgcaggtgaa tacacctgtc tggcaggcaa ctctatcggc|  |1020|
|ctttcctacc agtcagcttg gctcacagtg ttgccagaag aggacctcac gtggacggca|  |1080|
|gcagggcccg aggctaggta cacggatgtc atcctgtacg catcaggctc tctggctttg|  |1140|
|cttgtgcttc tgctgctggc tgggctctat cgccggcagg tgctccacgg ccggcacccc|  |1200|
|cggcagcccg ccaccgtgca gaaactctcc cgcttcccct tggcacgaca gttctccctg|  |1260|
|gagtcgggct cctcagccaa gtcaagctcg tctctggtgc ggggtgtccg tctctcctcc|  |1320|
|agcggccccc cattgctcgc tggcctcgtg agtctagacc tacctctcga cccactgtgg|  |1380|
|gagttccccc gggacaggct ggtgctcgga aagcccctgg gtgagggctg cttcgggcag|  |1440|
|gtggtgtgtg cagaggcctt tggcatggac cccacccggc ccgatcaagc cagcaccgtg|  |1500|

```
gctgtcaaga tgcttaagga caatgcttct gacaaggact tggctgacct agtctctgag    1560
atggaggtga tgaagctgat tggccgacac aagaacatca tcaatctgct gggagtctgc    1620
acccaggaag ggcccctgta cgtgattgtg gagtgtgctg ccaagggaaa cctgcgggag    1680
ttcctgcggg cccgccgccc cccaggccct gacctcagcc ctgatgggcc tcggagcagt    1740
gagggaccac tttccttccc tgccctggtc tcctgcgcat atcaggtggc ccgaggcatg    1800
cagtacctgg agtcacaaaa gtgcatccac cgggacctgg ctgcccgcaa cgtgctggtg    1860
actgaggaca atgtgatgaa gatcgctgac tttgggctgg cccgaggcat ccaccatatt    1920
gactactaca agaaaacaag caacggccgc ctgcctgtca gtggatggca acctgaggcc    1980
ttgtttgaca gagtctacac acaccagagt gacgtgtggt catttgggat cctgctgtgg    2040
gagatcttta ccctcggggg ctccccgtac cctggcatcc ccgtggagga gctgttctcg    2100
ctgctacggg agggccatcg gatggaccgg cccccacact gccctccaga gttgtatggg    2160
ctgatgcgtg agtgttggca cgcagcaccc tctcagaggc ccactttcaa gcagctggtg    2220
gaggcactgg acaaggtcct gctggctgtc tctgaagagt accttgacct ccgcttaacc    2280
tttggaccct actcccccgc cggtggggac gccagcagct cctgctcctc cagcgactcg    2340
gtcttcagcc atgagcccct gccccctggga cccagctcct tcttccctgg ggtgcagacg    2400
tgagcggtgg caccaggttg taccagtagg ccagttggca gccttgggtc tcccggctca    2460
gccacaacct ggtgaccttg gcagcccag gtcctgactt aagggtactg tcccagattt    2520
ctggttccgc tttggggagg tccgtctctg gtcctgggct ccctagttga gacttcctgc    2580
tccggcctca gcttctcaag ccagaattca gtcgtctca aggccctgcc cttgccttag    2640
agtcatggtc gtagtgttct attggctttt gaggttctgc ttggcctcat gggccttgat    2700
gcttcgtcct tgttccaggg cttccgttgg tcctggctgc agggttgtcc taaatctccc    2760
tgcttcccta catcaagaga agtcctggcc tctgaaccct atttccccag gcctccccag    2820
```

<210> SEQ ID NO 30
<211> LENGTH: 237
<212> TYPE: PRT
<213> ORGANISM: Macaca mulatta

<400> SEQUENCE: 30

```
Met Pro His Val Tyr Pro Ser Ser Phe Gly Asp Leu Glu Ile Phe Lys
1               5                   10                  15

Ala Cys Ser Asp Thr Glu Ser Ser Leu Asp Ser Asn Phe Ser Thr Leu
            20                  25                  30

Gly Trp Lys Arg Leu Leu Arg Phe Glu Thr Leu Ala Gly Lys Lys Met
        35                  40                  45

Gly Glu Lys Val Glu Phe Lys Leu Leu Glu Val Glu Ser Arg Leu Val
    50                  55                  60

Ala Gln Gln Lys Pro Arg Thr Ala Arg Gly Arg Gln Gly Pro Gly
65                  70                  75                  80

Gly Thr Met Ala Ala Gly Ser Ile Thr Thr Leu Pro Ala Leu Pro Glu
                85                  90                  95

Asp Gly Ser Gly Ala Phe Pro Pro Gly His Phe Lys Asp Pro Lys
            100                 105                 110

Arg Leu Tyr Cys Lys Asn Gly Gly Phe Phe Leu Arg Ile His Pro Asp
        115                 120                 125

Gly Arg Val Asp Gly Val Arg Glu Lys Ser Asp Pro His Ile Lys Leu
    130                 135                 140
```

Gln Leu Gln Ala Glu Glu Arg Gly Val Val Ser Ile Lys Gly Val Cys
145                 150                 155                 160

Ala Asn Arg Tyr Leu Ala Met Lys Glu Asp Gly Arg Leu Leu Ala Ser
            165                 170                 175

Lys Cys Val Thr Asp Glu Cys Phe Phe Phe Glu Arg Leu Glu Ser Asn
        180                 185                 190

Asn Tyr Asn Thr Tyr Arg Ser Arg Lys Tyr Thr Ser Trp Tyr Val Ala
    195                 200                 205

Leu Lys Arg Thr Gly Gln Tyr Lys Leu Gly Ser Lys Thr Gly Pro Gly
        210                 215                 220

Gln Lys Ala Ile Leu Phe Leu Pro Met Ser Ala Lys Ser
225                 230                 235

<210> SEQ ID NO 31
<211> LENGTH: 1063
<212> TYPE: DNA
<213> ORGANISM: Macaca mulatta

<400> SEQUENCE: 31
atgccccacg tgtacccctc gtcttttggt gatttagaga ttttcaaagc ctgctctgac      60
acagaatctt ccttggattc caacttctct actttggggt ggaaacggct tctccgtttt     120
gaaacgctag cggggaaaaa atggggggag aaagttgagt ttaaactttt agaagttgag     180
tcacggctgg ttgcgcagca aaagcccccgc acggctcggg gtccccggca gggcccggga     240
gggaccatgg cagccgggag catcaccacg ctgcccgcct tgcccgagga tggcggcagc     300
ggcgccttcc cgcctggcca cttcaaggac cccaagcggc tgtactgcaa aaacgggggc     360
ttcttcctgc gcattcaccc cgacggccga gttgacgggg tccgggagaa gagcgaccct     420
cacatcaaat tacaacttca gcagaagag agaggagttg tgtctatcaa aggagtgtgt     480
gctaaccgtt accttgctat gaaggaagat ggaagattac tggcttctaa atgtgttaca     540
gatgagtgtt tcttttttga acgattggaa tctaataact acaatactta ccggtcaagg     600
aaatacacca gttggtatgt ggcactgaaa cgaactgggc aatataaact tggatccaaa     660
acaggacctg gcagaaaagc tatacttttt cttccaatgt ctgctaagag ctgattttaa     720
tggccacatc taatctcatt tcacatgaaa gaagaagtat attgtagaaa tttgttaatg     780
agagtaaaag aaaataaatg tgtatagctc agtttggata attggtcaaa caacttttca     840
tctggtagta aaatatgtaa ccattgtccc agtaaagaaa actaacaaaa attgttgaaa     900
aatgtataga cttccccctt ttatatagca tctgctgtta cccagtgaag cttacctaga     960
gcaatgatct ttttcatgca tttgctttat tcagaaagag gcttttaaaa tgtgcacatt    1020
tagaaacaaa agttcttcat ggaaatcata tacattagaa aat                      1063

<210> SEQ ID NO 32
<211> LENGTH: 511
<212> TYPE: PRT
<213> ORGANISM: Macaca fascicularis

<400> SEQUENCE: 32

Met Glu Lys Lys Leu His Ala Val Pro Ala Ala Lys Thr Val Lys Phe
1               5                   10                  15

Lys Cys Pro Ser Ser Gly Thr Pro Asn Pro Thr Leu Arg Trp Leu Lys
            20                  25                  30

Asn Gly Lys Glu Phe Lys Pro Asp His Arg Ile Gly Gly Tyr Lys Val
        35                  40                  45

-continued

```
Arg Tyr Ala Thr Trp Ser Ile Ile Met Asp Ser Val Val Pro Ser Asp
 50              55                  60

Lys Gly Asn Tyr Thr Cys Ile Val Glu Asn Glu Tyr Gly Ser Ile Asn
 65              70                  75                  80

His Thr Tyr Gln Leu Asp Val Val Glu Arg Ser Pro His Arg Ser Ile
                 85                  90                  95

Leu Gln Ala Gly Leu Pro Ala Asn Lys Thr Val Ala Leu Gly Ser Asn
                100                 105                 110

Val Glu Phe Met Cys Lys Val Tyr Ser Asp Pro Gln Pro His Ile Gln
            115                 120                 125

Trp Leu Lys His Ile Glu Val Asn Gly Ser Lys Ile Gly Pro Asp Asn
130                 135                 140

Leu Pro Tyr Val Gln Ile Leu Lys Thr Ala Gly Val Asn Thr Thr Asp
145                 150                 155                 160

Lys Glu Met Glu Val Leu His Leu Arg Asn Val Ser Phe Glu Asp Ala
                165                 170                 175

Gly Glu Tyr Thr Cys Leu Ala Gly Asn Ser Ile Gly Leu Ser His His
                180                 185                 190

Ser Ala Trp Leu Thr Val Leu Glu Ala Leu Glu Glu Arg Pro Ala Val
            195                 200                 205

Met Thr Ser Pro Leu Tyr Leu Glu Ile Ile Ile Tyr Cys Thr Gly Ala
210                 215                 220

Phe Leu Ile Ser Cys Met Val Gly Ser Val Ile Val Tyr Lys Met Lys
225                 230                 235                 240

Ser Gly Thr Lys Lys Ser Asp Phe His Ser Gln Met Ala Val His Lys
                245                 250                 255

Leu Ala Lys Ser Ile Pro Leu Arg Arg Gln Val Thr Val Ser Ala Asp
                260                 265                 270

Ser Ser Ala Ser Met Asn Ser Gly Val Leu Leu Val Arg Pro Ser Arg
            275                 280                 285

Leu Ser Ser Ser Gly Thr Pro Met Leu Ala Gly Val Ser Glu Tyr Glu
290                 295                 300

Leu Pro Glu Asp Pro Arg Trp Glu Leu Pro Arg Asp Arg Leu Val Leu
305                 310                 315                 320

Gly Lys Pro Leu Gly Glu Gly Cys Phe Gly Gln Val Val Leu Ala Glu
                325                 330                 335

Ala Ile Gly Leu Asp Lys Asp Lys Pro Asn Arg Val Thr Lys Val Ala
                340                 345                 350

Val Lys Met Leu Lys Ser Asp Ala Thr Glu Lys Asp Leu Ser Asp Leu
            355                 360                 365

Ile Ser Glu Met Glu Met Met Lys Met Ile Gly Lys His Lys Asn Ile
370                 375                 380

Ile Asn Leu Leu Gly Ala Cys Thr Gln Asp Gly Pro Leu Tyr Val Ile
385                 390                 395                 400

Val Glu Tyr Ala Ser Lys Gly Asn Leu Arg Glu Tyr Leu Gln Ala Arg
                405                 410                 415

Arg Pro Pro Gly Leu Glu Tyr Cys Tyr Asn Pro Ser His Asn Pro Glu
                420                 425                 430

Glu Gln Leu Ser Ser Lys Asp Leu Val Ser Cys Ala Tyr Gln Val Ala
            435                 440                 445

Arg Gly Met Glu Tyr Leu Ala Ser Lys Lys Cys Ile His Arg Asp Leu
450                 455                 460

Ala Ala Arg Asn Val Leu Val Thr Glu Asp Asn Val Met Lys Ile Ala
```

```
                465                 470                 475                 480
Asp Phe Gly Leu Ala Arg Asp Ile His His Ile Asp Tyr Tyr Lys Lys
                    485                 490                 495
Lys Arg Ser Thr Ala Cys Glu Val Asp Gly Ala Arg Gly Ile Val
                    500                 505                 510

<210> SEQ ID NO 33
<211> LENGTH: 2890
<212> TYPE: DNA
<213> ORGANISM: Macaca fascicularis

<400> SEQUENCE: 33
ttcagatgct ctcccctcct cagaggatga tgatgatgat gatgactcct cttcagagga      60
gaaagagaca gataacacca aaccaaaccc cgtagctcca tattggacat ccccagaaaa     120
gatggaaaag aaattgcatg cggtgccagc tgccaagaca gtgaagttca aatgcccttc     180
cagtgggacc ccaaacccca cactgcgctg gttgaaaaat ggcaaagaat tcaaacctga     240
ccacaggatt ggaggctaca aggtccgtta tgccacctgg agcatcataa tggactccgt     300
ggtgccctct gacaagggca actacacctg cattgtggag aatgagtatg cagcatcaa     360
ccacacctac cagctggatg tcgtggagcg gtcccctcac cggtccatcc tgcaagcagg     420
gttgcccgcc aacaagacag tggccctggg tagcaacgtg gagttcatgt gtaaggtgta     480
cagtgaccca cagccgcata tccagtggct aaagcacatc gaggtgaacg ggagcaagat     540
tggtccagac aacctgcctt atgtccagat cttgaagact gctggagtta ataccaccga     600
caaagagatg gaggtgcttc acttaagaaa tgtctccttt gaggacgcag gggagtatac     660
gtgcttggcg ggtaactcta tcggactctc ccatcactct gcatggttga ccgttctgga     720
agctctggaa gagaggccgg cggtgatgac ctcgccctg tacctggaga tcatcatcta     780
ttgcacaggg gccttcctca tctcctgcat ggtagggtcg gtcatcgtct acaagatgaa     840
gagtggcacc aagaagagcg acttccacag ccagatggct gtgcacaagc tggccaagag     900
catccctctg cgcagacagg taacagtgtc tgctgactcc agtgcgtcca tgaactctgg     960
ggttcttctg gttcggccat acggctctc ctccagtggg actcccatgc tagcagggt    1020
ctccgagtat gagcttcctg aagaccctcg ctgggagctg cctcgggaca gactggtctt    1080
aggcaaaccc ctgggagagg ctgctttgg gcaggtggtt ttggcagagg ccatcgggtt    1140
ggacaaggac aaacccaacc gtgtgaccaa agtggctgtg aagatgttga gtcggacgc    1200
aacagagaaa gacttgtcag acctgatctc agaaatggag atgatgaaga tgatcggaa    1260
gcataagaat atcatcaacc tgctgggggc ctgcacgcag acggtccct tgtatgtcat    1320
cgtggagtat gcctccaagg caacctgcgg gagtacctg caggcccgga ggccccggg    1380
gctggaatac tgctacaacc ccagccacaa cccagaggag cagctctcct ccaaggacct    1440
ggtgtcctgc gcctatcagg tggcccgagg catggagtat ctggcctcca agaagtgcat    1500
acaccgagac ctggccgcca ggaatgtcct ggtgacagag acaatgtga tgaagatagc    1560
agactttggc ctcgcacggg acattcacca catcgactac tataaaaaga acggtcgac    1620
tgcctgtgaa gtggatggcg cccgaggcat tgttttgaccg gatctacacc caccagagtg    1680
atgtgtggtc tttcggggtg cttctgtggg agatcttcac tctgggcggc tccccatacc    1740
ctggtgtgcc tgtggaggag ctttcaagc tgctgaagga gggtcgccgc atggacaagc    1800
ccagtaactg caccaacgag ctgtacatga tgatgcggga ctgctggcat gcagtgccct    1860
cacagagacc caccttcaag cagctggtgg aagacctgga ccgcatcgtg gccttgacct    1920
```

```
ccaaccagga gtacctggac ctgtccatgc ccctggacca gtactccccg agctttcccg    1980
acacccggag ctctacatgc tcctcagggg aggattccgt cttctctcat gagccgctgc    2040
ccgaggagcc ctgcctgccc cgacacccag cccagcttgc caatggcggt ctcaaacgcc    2100
gctgactgcc acccacacgc cctccccaga ctctaccgtc agctgtaacc ctcacccaca    2160
gcccctgcca ggcccactgc ctgtccgtcc ctgtccccctt tcctgctggc aggagcccgc    2220
tgcctaccgg gggccttcct gtgtggcctg ccttcacccc gctcagctca cctcctcctc    2280
cgcctcctct ccacctgttg gtgagaggtg caaagaggca gatctttgct gccggccact    2340
tcatcccctc ccagatgttg gaccaagacc cctccctgcc accaggcact gcctggaggg    2400
cggggagtgg gagccgatga acaggcatgc aagtgagagc ttcctgagct ttctcctgtc    2460
agtttggtct gtttcgcctt cacccgtaag cccccttgcac tctggtggca ggtgccttgt    2520
cctcagggct acagcaatag ggaggtcagt gcttcgagcc tcgatcgaag gtgacctctg    2580
ctccagatgg gtggtgccag tggctttact aattccgata ctagtttgct ttgctcacta    2640
aatgcctggt accagaggat ggtgaggtga aggccaggtt gggggcagcg ttgtggccct    2700
ggggcccagc cccgaactgg gggctctgta catagctatg aagaaaacac aaagtgtata    2760
aatctgagta tatatttaca tgtctttta aaagggtcgt taccagagat ttacccatcg    2820
ggtaagatgc tcctggtggc tgggaggcat cagttgctat atattaaaaa caaaaaaaaa    2880
aaaaaaaaaa                                                          2890

<210> SEQ ID NO 34
<211> LENGTH: 34
<212> TYPE: PRT
<213> ORGANISM: Macaca mulatta

<400> SEQUENCE: 34

Glu Gln Tyr Ser Pro Ser Tyr Pro Asp Thr Arg Ser Ser Cys Ser Ser
1               5                   10                  15

Gly Asp Asp Ser Gly Phe Ser Pro Asp Pro Met Pro Tyr Glu Pro Cys
            20                  25                  30

Leu Pro

<210> SEQ ID NO 35
<211> LENGTH: 106
<212> TYPE: DNA
<213> ORGANISM: Macaca mulatta

<400> SEQUENCE: 35
tcgaacagta ttcacctagt taccctgaca caagaagttc ttgttcttca ggagatgatt    60
ctggtttttc tccagacccc atgccttacg aaccatgcct cctca                  106

<210> SEQ ID NO 36
<211> LENGTH: 808
<212> TYPE: PRT
<213> ORGANISM: Macaca mulatta

<400> SEQUENCE: 36

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Val Ala Glu Val Ser Gly Pro Glu Pro Ser Gln Gln Glu Gln
        35                  40                  45
```

```
Leu Val Phe Gly Ser Gly Asp Ala Val Glu Leu Ser Cys Pro Pro
         50                  55                  60
Gly Gly Gly Pro Met Gly Pro Thr Val Trp Val Lys Asp Gly Ala Gly
 65              70                  75                  80
Leu Val Pro Ser Glu Arg Val Leu Val Gly Pro Gln Arg Leu Gln Val
                 85                  90                  95
Leu Asn Ala Ser His Glu Asp Ser Gly Ala Tyr Ser Cys Arg Gln Arg
                100                 105                 110
Leu Thr Gln Leu Val Leu Cys His Phe Ser Val Arg Val Thr Asp Ala
            115                 120                 125
Pro Ser Ser Gly Asp Asp Glu Asp Gly Glu Asp Glu Ala Glu Asp Thr
        130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Lys Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
        210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
        290                 295                 300
Tyr Val Thr Val Leu Lys Ser Trp Ile Ser Glu Ser Val Glu Ala Asp
305                 310                 315                 320
Val Arg Leu Arg Leu Ala Asn Val Ser Glu Arg Asp Gly Gly Glu Tyr
                325                 330                 335
Leu Cys Arg Ala Thr Asn Phe Ile Gly Val Ala Glu Lys Ala Phe Trp
                340                 345                 350
Leu Ser Val His Arg Pro Arg Ala Ala Glu Glu Glu Leu Val Glu Ala
            355                 360                 365
Asp Glu Ala Gly Ser Val Tyr Ala Gly Ile Leu Ser Tyr Gly Val Gly
        370                 375                 380
Phe Phe Leu Phe Ile Leu Val Val Ala Ala Val Thr Leu Cys Arg Leu
385                 390                 395                 400
Arg Ser Thr Pro Lys Lys Gly Leu Gly Ser Pro Thr Val His Lys Ile
                405                 410                 415
Ser Arg Phe Pro Leu Lys Arg Gln Val Ser Leu Glu Ser Asn Ala Ser
                420                 425                 430
Met Ser Ser Asn Thr Pro Leu Val Arg Ile Ala Arg Leu Ser Ser Gly
            435                 440                 445
Glu Gly Pro Thr Leu Ala Asn Val Ser Glu Leu Glu Leu Pro Ala Asp
        450                 455                 460
```

| | | | | | | | | | | | | | | |
|---|---|---|---|---|---|---|---|---|---|---|---|---|---|---|
|Pro|Lys|Trp|Glu|Leu|Ser|Arg|Ala|Arg|Leu|Thr|Leu|Gly|Lys|Pro|Leu|
|465| | | |470| | | |475| | | |480| | |

Gly Glu Gly Cys Phe Gly Gln Val Val Met Ala Glu Ala Ile Gly Ile
            485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
515             520                 525

Glu Met Met Lys Met Ile Gly Lys His Lys Asn Ile Ile Asn Leu Leu
        530                 535                 540

Gly Ala Cys Thr Gln Gly Gly Pro Leu Tyr Val Leu Val Glu Tyr Ala
545             550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
610             615                 620

Val Leu Val Thr Glu Asp Asn Val Met Lys Ile Ala Asp Phe Gly Leu
625             630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
690             695                 700

Leu Phe Lys Leu Leu Lys Glu Gly His Arg Met Asp Lys Pro Ala Asn
705             710                 715                 720

Cys Thr His Asp Leu Tyr Met Ile Met Arg Glu Cys Trp His Ala Ala
            725                 730                 735

Pro Ser Gln Arg Pro Thr Phe Lys Gln Leu Val Glu Asp Leu Asp Arg
        740                 745                 750

Val Leu Thr Val Thr Ser Thr Asp Glu Tyr Leu Asp Leu Ser Ala Pro
            755                 760                 765

Phe Glu Gln Tyr Ser Pro Gly Gly Gln Asp Thr Pro Ser Ser Ser Ser
        770                 775                 780

Ser Gly Asp Asp Ser Val Phe Ala His Asp Leu Leu Pro Pro Ala Pro
785             790                 795                 800

Pro Ser Ser Gly Gly Ser Arg Thr
                805

<210> SEQ ID NO 37
<211> LENGTH: 2592
<212> TYPE: DNA
<213> ORGANISM: Macaca mulatta

<400> SEQUENCE: 37
ccccgccatg ggcgccctg cctgcgccct cgcgctctgc gtggcagtgg ccatcgtggc    60
cggcgcctcc tcggagtcct tggggacgga gcagcgcgtc gtgggcgag tgcagaagt   120 gtccggcccg gagcccagcc agcaggagca gttggtcttc ggcagcgggg acgctgtgga   180

-continued

```
gctgagctgt ccccgcccg ggggtggtcc catggggccc actgtctggg tcaaggatgg    240
cgcagggctg gtgccctcgg agcgtgtcct ggtggggccc cagcggctgc aggtgctgaa    300
tgcctcccac gaggactctg gggcctacag ctgccggcag cggctcacac agctcgtact    360
gtgccacttc agtgtgcggg tgacagatgc tccatcctcg ggagatgacg aagacgggga    420
ggacgaggct gaggacacag gtgtggacac aggggcccct tactggactc ggcccgagcg    480
gatggacaag aagctgctgg ctgtgccggc cgccaacacc gtccgcttcc gctgcccggc    540
tgccggcaac cccactccct ccatctcctg gctgaagaat ggcaaggagt ccgcggcga    600 gcaccgcatt ggcggcatca agcttcggca ccagcagtgg agcctggtca tggaaagcgt    660
ggtgccctcg gaccgcggca actacacctg cgtggtggag aacaagtttg cagcatccg    720 gcagacatac acgctggacg tgctggagcg ctccccgcac cggcccatcc tgcaggcggg    780
gctgccggcc aaccagacgg cggtgctggg cagcgatgtg gagtttcact gcaaggtgta    840
cagtgatgcg cagccccaca tccagtggct caagcacgtg gaggtgaatg cagcaaggt    900 gggcccgac ggcacaccct acgtcaccgt gctcaagtcc tggatcagtg agagtgtgga    960
ggccgacgtg cgcctccgcc tggccaatgt gtcggagcgg gacggggggcg agtacctctg   1020 tcgagccacc aatttcatag cgtggccga gaaggccttt tggctgagcg ttcacaggcc   1080
ccgagcagct gaggaggagc tggtggaggc tgacgaggcg ggcagtgtgt acgcaggcat   1140
cctcagctac ggggtgggct tcttcctgtt catcctggtg gtggcggctg tgacgctctg   1200
ccgcctgcgc agcaccccca agaaaggcct gggctccccc accgtgcaca agatctcccg   1260
cttcccactc aagcgacagg tgtccctgga gtccaacgcg tccatgagct ccaacacacc   1320
gctggtgcgc atcgcaaggc tgtcctcagg ggagggtccc acgctggcca atgtctccga   1380
gcttgagctg cctgctgacc ccaaatggga gctgtctcgg gcccggctga ccctgggcaa   1440
gccccttggg gagggctgct tcggccaggt ggtcatggcg gaggctatcg gcattgacaa   1500
ggaccgggcc gccaagcctg tcaccgtagc cgtgaagatg ctgaaagatg atgccactga   1560
caaggacctg tcagacctgg tgtctgagat ggagatgatg aagatgattg ggaaacacaa   1620
gaacattatc aacctgctgg gcgcctgcac gcagggcggg cccctgtacg tgctggtgga   1680
gtacgcggcc aagggcaacc tgagggagtt tctgcgggcg cggcggcccc gggcctgga   1740 ctactccttc gacacctgca gccgcctga ggagcaactc accttcaagg acctggtgtc   1800
ctgtgcctac caggtggccc gaggcatgga gtacctcgcc tcccagaagt gcatccacag   1860
ggacctggct gctcgaaatg tgctggtgac cgaggacaac gtgatgaaga tcgcagactt   1920
cgggctggcc cgcgacgtgc acaaccttga ctactacaag aagacaacca acggccggct   1980
gcccgtgaag tggatggcgc ctgaggccct gtttgaccga gtctacaccc accagagtga   2040
cgtctggtcc tttggggtcc tgctctggga gatcttcacg ctgggggggct ctccgtaccc   2100 cggcatccct gtgaggagc tcttcaagct gctgaaggag ggtcaccgga tggacaagcc   2160
ggccaactgc acacacgacc tgtacatgat catgcgggag tgctggcatg ctgcgccctc   2220
ccagaggccc accttcaagc agctggtgga ggacctggac cgtgtcctca ctgtgacgtc   2280
caccgacgag tacctggacc tgtcagcgcc cttcgagcag tactcccccg gcggccagga   2340
caccccgagc tccagctcct caggggatga ctccgtgttt gcccacgacc tgctgccccc   2400
ggccccaccc agcagtgggg gctcgcggac gtgaagggcc actggtcccc aacaatgtga   2460
gggggtccct agcagcctac cctgctgctg gtgcacagcc actccccggc atgagactca   2520
```

-continued

```
gtgcagatgg agagacagct acacaaagct tcagtctgtg tgcatccgtg tgtgtgtctg    2580
cgtgcgtgtg ca                                                        2592
```

<210> SEQ ID NO 38
<211> LENGTH: 802
<212> TYPE: PRT
<213> ORGANISM: Macaca mulatta

<400> SEQUENCE: 38

| | | | | | | | | | | | | | | |
|---|---|---|---|---|---|---|---|---|---|---|---|---|---|---|
| Met | Arg | Leu | Leu | Ser | Ala | Leu | Leu | Gly | Val | Leu | Leu | Ser | Val | Pro | Gly |
| 1 | | | | 5 | | | | | 10 | | | | | 15 | |
| Pro | Pro | Val | Leu | Ser | Leu | Glu | Ala | Ser | Glu | Glu | Val | Glu | Leu | Glu | Pro |
| | | | 20 | | | | | 25 | | | | | 30 | | |
| Cys | Leu | Ala | Pro | Ser | Met | Glu | Gln | Gln | Glu | Gln | Glu | Leu | Thr | Val | Ala |
| | | 35 | | | | | 40 | | | | | 45 | | | |
| Leu | Gly | Gln | Pro | Val | Arg | Leu | Cys | Cys | Gly | Arg | Ala | Glu | Arg | Gly | Gly |
| | 50 | | | | | 55 | | | | | 60 | | | | |
| His | Trp | Tyr | Lys | Glu | Gly | Ser | Arg | Leu | Ala | Pro | Ala | Gly | Arg | Val | Arg |
| 65 | | | | | 70 | | | | | 75 | | | | | 80 |
| Gly | Trp | Arg | Gly | Arg | Leu | Glu | Ile | Ala | Ser | Phe | Leu | Pro | Glu | Asp | Ala |
| | | | | 85 | | | | | 90 | | | | | 95 | |
| Gly | Arg | Tyr | Leu | Cys | Leu | Ala | Arg | Ala | Ser | Met | Ile | Val | Leu | Gln | Asn |
| | | | 100 | | | | | 105 | | | | | 110 | | |
| Leu | Thr | Leu | Thr | Ile | Asp | Asp | Ser | Leu | Thr | Ser | Ser | Asn | Asp | Asp | Glu |
| | | 115 | | | | | 120 | | | | | 125 | | | |
| Asp | Pro | Gln | Ser | His | Arg | Asp | Ser | Ser | Asn | Gly | His | Ile | Tyr | Pro | Gln |
| | 130 | | | | | 135 | | | | | 140 | | | | |
| Gln | Ala | Pro | Tyr | Trp | Thr | His | Pro | Gln | Arg | Met | Glu | Lys | Lys | Leu | His |
| 145 | | | | | 150 | | | | | 155 | | | | | 160 |
| Ala | Val | Pro | Ala | Gly | Asn | Thr | Val | Lys | Phe | Arg | Cys | Pro | Ala | Ala | Gly |
| | | | | 165 | | | | | 170 | | | | | 175 | |
| Asn | Pro | Thr | Pro | Thr | Ile | Arg | Trp | Leu | Lys | Asp | Gly | Gln | Ala | Phe | His |
| | | | 180 | | | | | 185 | | | | | 190 | | |
| Gly | Glu | Asn | Arg | Ile | Gly | Gly | Ile | Arg | Leu | Arg | His | Gln | His | Trp | Ser |
| | | 195 | | | | | 200 | | | | | 205 | | | |
| Leu | Val | Met | Glu | Ser | Val | Val | Pro | Ser | Asp | Arg | Gly | Thr | Tyr | Thr | Cys |
| | 210 | | | | | 215 | | | | | 220 | | | | |
| Leu | Val | Glu | Asn | Ala | Val | Gly | Ile | Ile | Arg | Tyr | Asn | Tyr | Leu | Leu | Asp |
| 225 | | | | | 230 | | | | | 235 | | | | | 240 |
| Val | Leu | Glu | Arg | Ser | Pro | His | Arg | Pro | Ile | Leu | Gln | Ala | Gly | Leu | Pro |
| | | | | 245 | | | | | 250 | | | | | 255 | |
| Ala | Asn | Thr | Thr | Ala | Val | Val | Gly | Ser | Asp | Val | Glu | Leu | Leu | Cys | Lys |
| | | | 260 | | | | | 265 | | | | | 270 | | |
| Val | Tyr | Ser | Asp | Ala | Gln | Pro | His | Ile | Gln | Trp | Leu | Lys | His | Ile | Val |
| | | 275 | | | | | 280 | | | | | 285 | | | |
| Ile | Asn | Gly | Ser | Ser | Phe | Gly | Ala | Asp | Gly | Phe | Pro | Tyr | Val | Gln | Val |
| | 290 | | | | | 295 | | | | | 300 | | | | |
| Leu | Lys | Thr | Ala | Asp | Ile | Asn | Ser | Ser | Glu | Val | Glu | Val | Leu | Tyr | Leu |
| 305 | | | | | 310 | | | | | 315 | | | | | 320 |
| Arg | Asn | Val | Ser | Ala | Glu | Asp | Ala | Gly | Glu | Tyr | Thr | Cys | Leu | Ala | Gly |
| | | | | 325 | | | | | 330 | | | | | 335 | |
| Asn | Ser | Ile | Gly | Leu | Ser | Tyr | Gln | Ser | Ala | Trp | Leu | Thr | Val | Leu | Pro |
| | | | 340 | | | | | 345 | | | | | 350 | | |
| Glu | Glu | Asp | Leu | Thr | Trp | Thr | Ala | Ala | Thr | Pro | Glu | Ala | Arg | Tyr | Thr |

```
              355                 360                 365
Asp Val Ile Leu Tyr Ala Ser Gly Ser Leu Ala Leu Ala Val Leu Leu
            370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Ser Lys Ser Ser Ser Ser Leu
            420                 425                 430
Val Arg Gly Val Arg Leu Ser Ser Ser Gly Pro Ala Leu Leu Ala Gly
            435                 440                 445
Leu Val Ser Leu Asp Leu Pro Leu Asp Pro Leu Trp Glu Phe Pro Arg
450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
Ala Ser Thr Val Ala Val Lys Met Leu Lys Asp Asn Ala Ser Asp Lys
                500                 505                 510
Asp Leu Ala Asp Leu Val Ser Glu Met Glu Val Met Lys Leu Ile Gly
            515                 520                 525
Arg His Lys Asn Ile Ile Asn Leu Leu Gly Val Cys Thr Gln Glu Gly
            530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Gln Ser Ser Glu Gly Pro Leu Ala Phe Pro Val Leu Val Ser Cys
            580                 585                 590
Ala Tyr Gln Val Ala Arg Gly Met Gln Tyr Leu Glu Ser Arg Lys Cys
            595                 600                 605
Ile His Arg Asp Leu Ala Ala Arg Asn Val Leu Val Thr Glu Asp Asn
            610                 615                 620
Val Met Lys Ile Ala Asp Phe Gly Leu Ala Arg Gly Ile His His Ile
625                 630                 635                 640
Asp Tyr Tyr Lys Lys Thr Ser Asn Gly Arg Leu Pro Val Lys Trp Met
                645                 650                 655
Ala Pro Glu Ala Leu Phe Asp Arg Val Tyr Thr His Gln Ser Asp Val
                660                 665                 670
Trp Ser Phe Gly Val Leu Leu Trp Glu Ile Phe Thr Leu Gly Gly Ser
            675                 680                 685
Pro Tyr Pro Gly Ile Pro Val Glu Glu Leu Phe Ser Leu Leu Arg Glu
            690                 695                 700
Gly His Arg Met Asp Arg Pro Pro His Cys Pro Pro Glu Leu Tyr Gly
705                 710                 715                 720
Leu Met Arg Glu Cys Trp His Ala Ala Pro Ser Gln Arg Pro Thr Phe
                725                 730                 735
Lys Gln Leu Val Glu Ala Leu Asp Lys Val Leu Leu Ala Val Ser Glu
                740                 745                 750
Glu Tyr Leu Asp Leu Arg Leu Thr Phe Gly Pro Tyr Ser Pro Ala Gly
            755                 760                 765
Gly Asp Thr Ser Ser Thr Cys Ser Ser Ser Asp Ser Val Phe Ser His
            770                 775                 780
```

Asp Pro Leu Pro Leu Gly Ser Ser Ser Phe Pro Phe Gly Ser Gly Val
785                 790                 795                 800

Gln Thr

<210> SEQ ID NO 39
<211> LENGTH: 2901
<212> TYPE: DNA
<213> ORGANISM: Macaca mulatta

<400> SEQUENCE: 39

```
agttggtggg aagtccagcc tgggcccctg agagctgcgg gaaggagatg cggctgctgt      60
cggccctctt gggggtcctg ctgagtgtgc ctgggcctcc agtcttgtcc ctggaggcct     120
cggaggaagt ggagctggag ccctgcctgg ctcccagcat ggagcagcaa gagcaggagc     180
tgacagtagc ccttgggcag cctgtgcggc tgtgctgtgg gcgggctgag cgtggtggcc     240
actggtacaa ggagggcagt cgcctggcac ctgctggccg tgtacgggc tggaggggcc      300
gcctagagat tgccagcttc ctacctgagg atgctggcc ctatctctgc ctggcccgag      360
cctccatgat cgtcctgcaa aatctccacct tgactataga tgactccttg acctccagca    420
acgatgatga ggaccccag tcccataggg actcctcgaa tgggcacatt tacccccagc      480
aagcacccta ctggacacac ccccagcgca tggagaagaa actgcatgca gtaccggctg     540
ggaacaccgt caagttccgc tgtccggctg caggcaaccc cacgcccacc atccgctggc     600
ttaaggatgg acaggccttt catggggaga accgcattgg aggcattcgg ctgcgccacc     660
agcactggag tctcgtgatg gagagcgtgg tgccctcgga ccgcggcaca tacacttgcc     720
tggtggagaa cgctgtgggc atcatccgct ataactacct gctggatgtg ctggagcggt     780
ccccgcaccg gccatcctg caggctgggc tcccggccaa caccacagcc gtggtgggca     840
gtgacgtgga gctgctgtgc aaggtgtaca gcgatgccca gccccacatc cagtggctga     900
agcacatcgt catcaacggc agcagcttcg gggccgacgc cttcccctat gtgcaagtcc     960
tgaagactgc agacatcaat agctcagagg tggaggtcct gtacctgcgg aacgtgtcag    1020
ccgaggacgc aggcgagtac acctgccttg caggcaattc catcggcctc tcctaccagt    1080
ctgcctggct cacggtgctg ccagaggagg acctcacatg gaccgcagca acgcccgagg    1140
ccaggtatac ggacgtcatc ctgtacgcgt cgggctccct ggccttggct gtgctcctgc    1200
tgctggccgg gctgtatcga gggcaggcgc tccacggccg gcacccccgc ccacccgcca    1260
ccgtgcagaa gctctcccgc ttccctctgg cccgacagtt ctccctggag tcaggctctt    1320
ccagcaagtc aagctcatcc ctggtgcgag gcgtgcgtct ctcctccagc ggccccgcct    1380
tgctcgccgg cctcgtgagt ctagacctac ctctcgaccc actgtgggag ttccccggg     1440
acaggctggt gcttgggaag cccctgggcg agggctgctt tggacaggta gtacgtgcag    1500
aggcctttgg catggaccct gcccggcctg accaagccag tactgtggct gtcaagatgc    1560
tcaaagacaa cgcctctgac aaggacctgg ctgacctggt ctcggagatg gaggtgatga    1620
agctgattgg ccgacacaag aacatcatca acctgctggg tgtctgcacc caggaagggc    1680
ccctgtatgt aatcgtggag tgcgctgcca agggaaacct tcgggagttc ctgcgggccc    1740
ggcgcccccc gggccctgac ctcagcccgg acggtcctca gagcagtgag gggccactcg    1800
ccttcccagt cctggtctcc tgcgcctacc aggtggccca aggcatgcag tatctggagt    1860
cccgaaagtg tatccaccgg gacctggctg cccgcaatgt gctggtgacg gaggacaatg    1920
tgatgaagat agctgacttt gggctggccc gtggcatcca ccacattgac tactataaga    1980
```

```
aaaccagcaa cggccgcctg cctgtcaagt ggatggcgcc cgaggccttg tttgaccgag    2040
tgtacacaca ccagagtgac gtgtggtctt ttggggtcct gctgtgggag atcttcaccc    2100
tcgggggctc cccgtatcct ggcatcccgg tggaggagct gttctcactg ctgcggagg    2160 gacatcggat ggaccgaccc ccacactgcc cccagagct gtacgggctg atgcgtgagt    2220
gctggcatgc agcaccctcc cagaggccca ccttcaagca gctggtggag gcgctggaca    2280
aggtcttact ggccgtctct gaggagtacc tcgacctccg cctgaccttc ggaccctatt    2340
cccctgctgg tggggacacc agcagcacct gctcctccag tgactccgtc ttcagccacg    2400
accccctgcc actgggatcc agctccttcc cctttgggtc tggggtgcag acatgagtaa    2460
ggctcaaggc tgtgcaggca cataaactag tggccttggg ccttggggct cagccacagc    2520
ctggcacagt gcttgacctt ggcagcacgg ggtccctggc ccagagtgct gtcccaggtc    2580
caaggccgtg cccttgccct tggcgctgca gtgcctgtgt cctgatgggc caaacgtcag    2640
ggttctgctc ggcccttgga ccttggcgct cagcccccac ctcaggtttg ctgagcctg    2700 gctggagagc tgctatgcta atctcctgc ctcccaatac cagcagggggg ttcagggcct    2760 ctgaaccccc tttccccaca cctcccccctg ctgcttgccc cagcgtcttg atgggagcgt    2820
cggcccctga gcccagagaa gctggaagcc cgccaaaaac aggagcaaat ggcgttctat    2880
aaattatttt tttgaaataa a                                              2901
```

<210> SEQ ID NO 40
<211> LENGTH: 154
<212> TYPE: PRT
<213> ORGANISM: Mus musculus

<400> SEQUENCE: 40

```
Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150
```

<210> SEQ ID NO 41
<211> LENGTH: 695
<212> TYPE: DNA
<213> ORGANISM: Mus musculus

<400> SEQUENCE: 41

```
ggccccgggc cgttgtacac tcaaggggct ctctcggctt caggaagagt ccggctgcac    60
tgggctggga gccggcgggg acacggactg ggaggctggc agcccgcggg cgagccgcgc   120 tgggggggccg aggccggggt cggggccggg gagccccaag agctgccaca gcggggtccc   180
ggggccgcgg aagggccatg gctgccagcg gcatcacctc gcttcccgca ctgccggagg   240
acggcggcgc cgccttccca ccaggccact tcaaggaccc caagcggctc tactgcaaga   300
acggcggctt cttcctgcgc atccatcccg acggccgcgt ggatggcgtc cgcgagaaga   360
gcgacccaca cgtcaaacta caactccaag cagaagagag aggagttgtg tctatcaagg   420
gagtgtgtgc caaccggtac cttgctatga aggaagatgg acggctgctg gcttctaagt   480
gtgttacaga agagtgtttc ttctttgaac gactggaatc taataactac aatacttacc   540
ggtcacggaa atactccagt tggtatgtgg cactgaaacg aactgggcag tataaactcg   600
gatccaaaac gggacctgga cagaaggcca tactgtttct tccaatgtct gctaagagct   660
gactcacttt tgacactgtc actgagacac tgtca                              695
```

<210> SEQ ID NO 42
<211> LENGTH: 822
<212> TYPE: PRT
<213> ORGANISM: Mus musculus

<400> SEQUENCE: 42

```
Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Ala Gln
            20                  25                  30

Pro Trp Gly Val Pro Val Glu Val Glu Ser Leu Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Val Glu Ser Asn Arg Thr Arg
65                  70                  75                  80

Ile Thr Gly Glu Glu Val Glu Val Arg Asp Ser Ile Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Arg Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255
```

```
Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Leu Gly Ser Val Ile Ile Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670
```

```
Phe Asp Arg Ile Tyr Thr His Gln Ser Asp Val Trp Ser Phe Gly Val
            675                 680                 685
Leu Leu Trp Glu Ile Phe Thr Leu Gly Gly Ser Pro Tyr Pro Gly Val
        690                 695                 700
Pro Val Glu Glu Leu Phe Lys Leu Leu Lys Glu Gly His Arg Met Asp
705                 710                 715                 720
Lys Pro Ser Asn Cys Thr Asn Glu Leu Tyr Met Met Arg Asp Cys
                725                 730                 735
Trp His Ala Val Pro Ser Gln Arg Pro Thr Phe Lys Gln Leu Val Glu
            740                 745                 750
Asp Leu Asp Arg Ile Val Ala Leu Thr Ser Asn Gln Glu Tyr Leu Asp
        755                 760                 765
Leu Ser Ile Pro Leu Asp Gln Tyr Ser Pro Ser Phe Pro Asp Thr Arg
    770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Thr Gln Leu Ala Asn
                805                 810                 815
Ser Gly Leu Lys Arg Arg
                820

<210> SEQ ID NO 43
<211> LENGTH: 5008
<212> TYPE: DNA
<213> ORGANISM: Mus musculus

<400> SEQUENCE: 43
agccctcgcg cctcgccggc gcacagcgct cggagcgctc ctgcgggtac tttggcgggg    60
ctctccgctg cgggcggcgc ggaacgggag ccggaaccct ggtgcagccg ctgcgtgcag   120
aggacccggg ctgcgcaggg aagcggggcc gagacgtccg gactggactg agactgtgct   180
tagcgcattg cggcgacctc gccttcccg gccgcgagcg cgcgccgcag ctggaaaagc    240
agcggagacc gaggactttt ctcaggtccc aggggcgcac acagccgtg ctgcagtcaa    300
tgcacgccgg agccccagga ggggtgatgg aactcgggct gccagaagcc tgagacgccg   360
ccaccgccgc cgctgcgtac tggagagcgg ggggcgcacg atctggggac cccgggcggc   420
ggacccgagc cctccccccc gccccgcctc cggggcacca gcttcggctc cattgttccc   480
gcccgggctg gaggcgcccg gctcggagtg ccgccgggag tcgtgcctcg gccgcggagc   540
cctcgagacc ccatcaggat ctgaacgag cccgagacg agcggcggga gcgcaagaca    600
cagacacccg ccgcgccacg gcgagctctc cagaggcggg accgcagcgc caagtgagag   660
tcagcttgcg aaggcagacc acgctcacgg tggaatatcc atggaggtac ggagccttgt   720
taccaacctc taaccgcaga actgggatgt ggggctggaa gtgcctcctc ttctgggctg   780
tgctggtcac agccactctc tgcactgcca ggccagcccc aaccttgcct gaacaagctc   840
agccctgggg agtccctgtg gaagtggagt ctctcctggt ccaccctggc gacctgctac   900
agcttcgctg tcggcttcgc gatgatgtgc agagcatcaa ctggctgcgg gatggggtgc   960
agctggtgga gagcaaccgt acccgcatca caggggagga ggtggaggtg cgggactcca  1020
tccccgctga ctctggcctc tacgcttgcg tgaccagcag cccctctggc agcgatacca  1080
cctacttctc cgtcaatgtc tcagatgcac tccatcctc ggaagatgat gacgacgacg  1140
atgactcctc ctcggaggag aaagagacga caacaccaa accaaccgt aggcctgtag   1200
ctccctactg gacatcccca gagaaaatgg agaagaaact gcatgcggtg cccgctgcca  1260
```

-continued

```
agacggtgaa gttcaagtgc ccgtcgagtg ggacacccaa cccccactctg cgctggttga    1320 aaaatggcaa agagtttaag cctgaccacc gaattggagg ctacaaggtt cgctatgcca    1380
cctggagcat cataatggat tctgtggtgc cttctgacaa gggcaactac acctgcatcg    1440
tggagaatga gtatgggagc atcaaccaca cctaccagct tgacgtcgtg aacgatctc     1500 cgcaccgacc catccttcag gcagggctgc ctgccaacaa gacagtggcc ctgggcagca    1560
atgtggagtt catgtgtaag gtgtacagcg atccgcagcc tcacattcag tggctgaagc    1620
acatcgaggt gaacgggagt aagatcgggc cagacaactt gccgtatgtc cagatcctga    1680
agactgctgg agttaatacc accgacaagg aaatggaggt gcttcatcta cggaatgtct    1740
cctttgagga tgcgggggag tatacgtgct tggcgggtaa ctctatcgga ctctcccatc    1800
actctgcatg gttgaccgtt ctggaagccc tggaagagag accagctgtg atgacctcac    1860
cgctctacct ggagatcatt atctactgca ccggggcctt cctgatctcc tgcatgttgg    1920
gctctgtcat catctataag atgaagagcg gcaccaagaa gagcgacttc catagccaga    1980
tggctgtgca caagctggcc aagagcatcc ctctgcgcag acaggtaaca gtgtcagctg    2040
actccagtgc atccatgaac tctggggttc tcctggttcg gccctcacgg ctctcctcca    2100
gcgggacccc catgctggct ggagtctccg aatatgagct ccctgaggat ccccgctggg    2160
agctgccacg agacagactg gtcttaggca aaccacttgg cgagggctgc ttcgggcagg    2220
tggtgttggc tgaggccatc gggctggata aggacaaacc caaccgtgtg accaaagtgg    2280
ccgtgaagat gttgaagtcc gacgcaacgg agaaggacct gtcggatctg atctcggaga    2340
tggagatgat gaaaatgatt gggaagcaca agaatatcat caaccttctg ggagcgtgca    2400
cacaggatgg tcctctttat gtcattgtgg agtacgcctc caaaggcaat ctccgggagt    2460
atctacaggc ccggaggcct cctgggctgg agtactgcta taacccccagc cacaaccccg    2520 aggaacagct gtcttccaaa gatctggtat cctgtgccta tcaggtggct cggggcatgg    2580
agtatcttgc ctctaagaag tgtatacacc gagacctggc tgctaggaac gtcctggtga    2640
ccgaggataa cgtaatgaag atcgcagact ttggcttagc tcgagacatt catcatatcg    2700
actactacaa gaaaaccacc aacggccggc tgcctgtgaa gtggatggcc cctgaggcgt    2760
tgtttgaccg gatctacaca caccagagcg atgtgtggtc ttttggagtg ctcttgtggg    2820
agatcttcac tctgggtggc tccccatacc ccggtgtgcc tgtggaggaa cttttcaagc    2880
tgctgaagga gggtcatcga atggacaagc ccagtaactg taccaatgag ctgtacatga    2940
tgatgcggga ctgctggcat gcagtgccct ctcagagacc tacgttcaag cagttggtgg    3000
aagacctgga ccgcattgtg gccttgacct ccaaccagga gtatctggac ctgtccatac    3060
cgctggacca gtactcaccc agctttcccg acacacggag ctccacctgc tcctcagggg    3120
aggactctgt cttctctcat gagccgttac ctgaggagcc ctgtctgcct cgacacccca    3180
cccagcttgc caacagtgga ctcaaacggg ctgactacc aacctgtcc ccagttttct      3240 cccattccgt cgtcacccgt gcccctcacc cacaatcccc ttgttggaca cactgccttt    3300
ctcctcctcc tttgccgctg caagagcca gtgcctgact gaggccttcc tgtgttgtgg     3360
ccttccccct ccatcacccc caagacccct cttctccctc ttcttagcct gctgtgtgag    3420
agaggagcca agaggcaggt gcttgccgac ggccgcatcc tccttcccag gtgttggacc    3480
aagacccgcc ccgctgcctg gcactgcttg gaggtgtgca gagcggaagc aagtggagca    3540
tccggggcat tcctgttgac ccatcagccc cttctgttct ggcggcaggg gccttggggc    3600
```

```
tcctggaagc cgtgaggttt ctgtttaggc cttaaccgaa ggcaacctct gctccagatg    3660
gatggtacca gtagcttctt aattccaata ctaatttgct ttgctgacca atacctgcc     3720 tggtaccaga agacagggag gcagagactg ggagccgtga tgtgcccttg ggctgagccc    3780
tagacttggg gctctgtaca tagctatgaa gaaaaacaca aagtgtataa atcttgagta    3840
tatatttaca tgtcttttta aaaagggtcg ttactagaga tttacccatg ggggagacgc    3900
ccagggtagc atccgttgct atatattaaa aacaaacgaa cagaaagaaa aaaaaaagga    3960
aaatgttttt taaaaggtca tatatttttt tgctactttt gctgttttat ttttttaaat    4020
tatgttttaa acctatttc agtttaggtt tccctcaata aaaaattgct gctgcttcat      4080
ttttatcctg ggcgtgtgaa aagagagcag gtgtccagcg cagaggaggg agacaggggg    4140
taaagggcca tgagctggtc ttccccctgc cccccatgac ctctgtctcc tggattgtgc    4200
cccagacctc ccagccaagc cttctatctc ccgatgcatt gggaacagca ggagaagact    4260
gaggtcctga gggcagagag ccaagctcgc acacttgatt gtttcctcgg aggagagagt    4320
gagaggatga ggttagccag agggtagaac tggacagaaa cccaaaccct agaccctgta    4380
cattcagatg tcttgtctat cttccccaac ctactcctca tattcctctc ctgtaaatat    4440
cctccccttc cctgttggtc tctgttaccc agttgggtct gtccctgagc ttggcttcct    4500
atagtttttc cttcacaaac tccacccatc cctcaggaaa cagaaaacga tctctttggt    4560
tggggtcaac ttggcaactc aattctgcca cctgctggtt gctttggtac cttggtctct    4620
tattcaaacc cacaccactc aagccttaga gggtttgttt ttgttttttg tttgtttgtt    4680
tggttggttg gttggtcttt tttttctggg tctgctgaat acaaacctgt tcagtatgat    4740
ttcatctgta ggggttaggg ctgcttcttt aaatgcagtt ttggcagctg tggtttgggt    4800
cattgtcata agagttctta tcgttgtttc tctctgtaca catgtaactg tcaaaatatt    4860
atgaatggtt tttatgctga agaagacat catttggcaa agagggctag ggaatgaatt     4920
tagcacaaac tcattttctt ggagaccgtg tatcatagtg gtttttttt ttttctttc       4980 tcttgttaaa actgaacatt atttctgc                                         5008
```

<210> SEQ ID NO 44  
<211> LENGTH: 840  
<212> TYPE: PRT  
<213> ORGANISM: Mus musculus

<400> SEQUENCE: 44

```
Met Gly Leu Pro Ser Thr Trp Arg Tyr Gly Arg Gly Pro Gly Ile Gly
1               5                   10                  15

Thr Val Thr Met Val Ser Trp Gly Arg Phe Ile Cys Leu Val Leu Val
            20                  25                  30

Thr Met Ala Thr Leu Ser Leu Ala Arg Pro Ser Phe Ser Leu Val Glu
        35                  40                  45

Asp Thr Thr Leu Glu Pro Glu Glu Pro Pro Thr Lys Tyr Gln Ile Ser
    50                  55                  60

Gln Pro Glu Ala Tyr Val Val Ala Pro Gly Glu Ser Leu Glu Leu Gln
65                  70                  75                  80

Cys Met Leu Lys Asp Ala Ala Val Ile Ser Trp Thr Lys Asp Gly Val
                85                  90                  95

His Leu Gly Pro Asn Asn Arg Thr Val Leu Ile Gly Glu Tyr Leu Gln
            100                 105                 110

Ile Lys Gly Ala Thr Pro Arg Asp Ser Gly Leu Tyr Ala Cys Thr Ala
        115                 120                 125
```

```
Ala Arg Thr Val Asp Ser Glu Thr Trp Tyr Phe Met Val Asn Val Thr
    130             135                 140
Asp Ala Ile Ser Ser Gly Asp Asp Glu Asp Asp Thr Asp Ser Ser Glu
145             150                 155                 160
Asp Val Val Ser Glu Asn Arg Ser Asn Gln Arg Ala Pro Tyr Trp Thr
                165                 170                 175
Asn Thr Glu Lys Met Glu Lys Arg Leu His Ala Val Pro Ala Ala Asn
                180                 185                 190
Thr Val Lys Phe Arg Cys Pro Ala Gly Gly Asn Pro Thr Pro Thr Met
            195                 200                 205
Arg Trp Leu Lys Asn Gly Lys Glu Phe Lys Gln Glu His Arg Ile Gly
    210                 215                 220
Gly Tyr Lys Val Arg Asn Gln His Trp Ser Leu Ile Met Glu Ser Val
225                 230                 235                 240
Val Pro Ser Asp Lys Gly Asn Tyr Thr Cys Leu Val Glu Asn Glu Tyr
                245                 250                 255
Gly Ser Ile Asn His Thr Tyr His Leu Asp Val Val Glu Arg Ser Pro
            260                 265                 270
His Arg Pro Ile Leu Gln Ala Gly Leu Pro Ala Asn Ala Ser Thr Val
            275                 280                 285
Val Gly Gly Asp Val Glu Phe Val Cys Lys Val Tyr Ser Asp Ala Gln
    290                 295                 300
Pro His Ile Gln Trp Ile Lys His Val Glu Lys Asn Gly Ser Lys Tyr
305                 310                 315                 320
Gly Pro Asp Gly Leu Pro Tyr Leu Lys Val Leu Lys Ala Ala Gly Val
                325                 330                 335
Asn Thr Thr Asp Lys Glu Ile Glu Val Leu Tyr Ile Arg Asn Val Thr
            340                 345                 350
Phe Glu Asp Ala Gly Glu Tyr Thr Cys Leu Ala Gly Asn Ser Ile Gly
            355                 360                 365
Ile Ser Phe His Ser Ala Trp Leu Thr Val Leu Pro Ala Pro Val Arg
    370                 375                 380
Glu Lys Glu Ile Thr Ala Ser Pro Asp Tyr Leu Glu Ile Ala Ile Tyr
385                 390                 395                 400
Cys Ile Gly Val Phe Leu Ile Ala Cys Met Val Val Thr Val Ile Phe
                405                 410                 415
Cys Arg Met Lys Thr Thr Lys Lys Pro Asp Phe Ser Ser Gln Pro
                420                 425                 430
Ala Val His Lys Leu Thr Lys Arg Ile Pro Leu Arg Arg Gln Val Thr
            435                 440                 445
Val Ser Ala Glu Ser Ser Ser Ser Met Asn Ser Asn Thr Pro Leu Val
450                 455                 460
Arg Ile Thr Thr Arg Leu Ser Ser Thr Ala Asp Thr Pro Met Leu Ala
465                 470                 475                 480
Gly Val Ser Glu Tyr Glu Leu Pro Glu Asp Pro Lys Trp Glu Phe Pro
                485                 490                 495
Arg Asp Lys Leu Thr Leu Gly Lys Pro Leu Gly Glu Gly Cys Phe Gly
                500                 505                 510
Gln Val Val Met Ala Glu Ala Val Gly Ile Asp Lys Asp Lys Pro Lys
            515                 520                 525
Glu Ala Val Thr Val Ala Val Lys Met Leu Lys Asp Asp Ala Thr Glu
530                 535                 540
```

```
Lys Asp Leu Ser Asp Leu Val Ser Glu Met Glu Met Lys Met Ile
545                 550                 555                 560
Gly Lys His Lys Asn Ile Ile Asn Leu Leu Gly Ala Cys Thr Gln Asp
                565                 570                 575
Gly Pro Leu Tyr Val Ile Val Glu Tyr Ala Ser Lys Gly Asn Leu Arg
            580                 585                 590
Glu Tyr Leu Arg Ala Arg Arg Pro Gly Met Glu Tyr Ser Tyr Asp
        595                 600                 605
Ile Asn Arg Val Pro Glu Glu Gln Met Thr Phe Lys Asp Leu Val Ser
    610                 615                 620
Cys Thr Tyr Gln Leu Ala Arg Gly Met Glu Tyr Leu Ala Ser Gln Lys
625                 630                 635                 640
Cys Ile His Arg Asp Leu Ala Ala Arg Asn Val Leu Val Thr Glu Asn
                645                 650                 655
Asn Val Met Lys Ile Ala Asp Phe Gly Leu Ala Arg Asp Ile Asn Asn
                660                 665                 670
Ile Asp Tyr Tyr Lys Lys Thr Thr Asn Gly Arg Leu Pro Val Lys Trp
            675                 680                 685
Met Ala Pro Glu Ala Leu Phe Asp Arg Val Tyr Thr His Gln Ser Asp
        690                 695                 700
Val Trp Ser Phe Gly Val Leu Met Trp Glu Ile Phe Thr Leu Gly Gly
705                 710                 715                 720
Ser Pro Tyr Pro Gly Ile Pro Val Glu Glu Leu Phe Lys Leu Leu Lys
                725                 730                 735
Glu Gly His Arg Met Asp Lys Pro Thr Asn Cys Thr Asn Glu Leu Tyr
            740                 745                 750
Met Met Met Arg Asp Cys Trp His Ala Val Pro Ser Gln Arg Pro Thr
        755                 760                 765
Phe Lys Gln Leu Val Glu Asp Leu Asp Arg Ile Leu Thr Leu Thr Thr
    770                 775                 780
Asn Glu Glu Tyr Leu Asp Leu Thr Gln Pro Leu Glu Gln Tyr Ser Pro
785                 790                 795                 800
Ser Tyr Pro Asp Thr Arg Ser Ser Cys Ser Ser Gly Asp Asp Ser Val
                805                 810                 815
Phe Ser Pro Asp Pro Met Pro Tyr Glu Pro Cys Leu Pro Gln Tyr Pro
            820                 825                 830
His Ile Asn Gly Ser Val Lys Thr
            835                 840

<210> SEQ ID NO 45
<211> LENGTH: 5223
<212> TYPE: DNA
<213> ORGANISM: Mus musculus
<400> SEQUENCE: 45
gatgtgcgga taagtacaat tacctattca cgtgttccct tcctaaagga gggtttccca      60
aacactcgtc ccctgtctat tgttcagagg aacaagacaa cgcaacatct cccacgaaca     120
tccgctgctt ccaccctcaa agcttcatga catgaaatgt ctggcccag tatgctgcag      180
acctattcta aggtgtctga agttgcacag cattctgtca tttgtttcct aacttgacat     240
aaaacaacgt aacgcatcca ctgtgcacca agctggcta ggaactgggg cagtggcgta      300
cagaggccgt tcaccaacag ggttccgaga ggtcatctgt gcaccctgc gggcagcgcg      360
gcggggcccc tcgcctgcct ggcgggtgtc tctttgcggc tgctaggctt cggggggcagc    420
```

```
gcggggctcg ggactgcccc agcgcgaggc gctgattggc agagcgggcg ccgccgtcca    480
ggaaacggct cgggtttcag cggggggcgt gacccgcccg aggaggctgc ggcggcggcg    540
cgggcggcga ggggagagag ccgggagagg cgagcggcgg cggcggcagg cgcggaacgg    600
gcgcacggac gatcgaacgc gcggccgcca gagctccggc gcggggggctg cctgtgtgtt    660 cctggcccgg cgtggcgact gctctccggg ctggcggggg ccgggcgtga gccccgggc    720 ctcagcgttc ctgagcgctg cgagtgttca ctactcgcca gcaaagtttg gagtaggcaa    780
cgccaagctc cagtcctttc ttctgctgct gcccagatcc gagagcagct ccggtgtcat    840
gtcctagctg ttctgcgatc cccggcgcgc gtgaagcctc ggaaccttgg cgccggctgc    900
tacccaagga atcgttctct ttttggagtt ttcctccgag atcatcgcct gctccatccc    960
gatccactct gggctccggc gcagcaccga gcgcagagga gcgctgccat tcaagtggca   1020
gccacagcag cagcagcagc agcagtggga gcaggaacag cagtaacaac agcaacagca   1080
gcacagccgc ctcagagctt tggctcctga gcccctgtg ggctgaaggc attgcaggta   1140
gcccatggtc tcagaagaag tgtgcagatg ggattaccgt ccacgtggag atatggaaga   1200
ggaccaggga ttggcactgt gaccatggtc agctgggggc gcttcatctg cctggtcttg   1260
gtcaccatgg caaccttgtc cctggcccgg ccctccttca gtttagttga ggataccact   1320
ttagaaccag aagagccacc aaccaaatac caaatctccc aaccagaagc gtacgtggtt   1380
gcccccgggg aatcgctaga gttgcagtgc atgttgaaag atgccgccgt gatcagttgg   1440
actaaggatg gggtgcactt ggggcccaac aataggacag tgcttattgg ggagtatctc   1500
cagataaaag gtgccacacc tagagactcc ggcctctatg cttgtactgc agctaggacg   1560
gtagacagtg aaacttggta cttcatggtg aatgtcacag atgccatctc atctggagat   1620
gatgaggacg acacagatag ctccgaagac gttgtcagtg agaacaggag caaccagaga   1680
gcaccgtact ggaccaacac cgagaagatg gagaagcggc tccacgctgt ccctgccgcc   1740
aacactgtga gttccgctg tccggctggg gggaatccaa cgcccacaat gaggtggtta   1800
aaaaacggga aggagtttaa gcaggagcat cgcattggag gctataaggt acgaaaccag   1860
cactggagcc ttattatgga aagtgtggtc ccgtcagaca aaggcaacta cacctgcctg   1920
gtggagaatg aatacgggtc catcaaccac acctaccacc tcgatgtcgt tgaacggtca   1980
ccacaccggc ccatcctcca agctggactg cctgcaaatg cctccacggt ggtcggaggg   2040
gatgtggagt ttgtctgcaa ggtttacagc gatgcccagc cccacatcca gtggatcaag   2100
cacgtggaaa agaacggcag taaatacggg cctgatgggc tgccctacct caaggtcctg   2160
aaggccgccg gtgttaacac cacggacaaa gagattgagg ttctctatat tcggaatgta   2220
acttttgagg atgctgggga atatacgtgc ttggcgggta attctatcgg gatatccttt   2280
cactctgcat ggttgacagt tctgccagcg cctgtgagag agaaggagat cacggcttcc   2340
ccagattatc tggagatagc tatttactgc ataggggtct tcttaatcgc ctgcatggtg   2400
gtgacagtca tcttttgccg aatgaagacc acgaccaaga gccagacttt cagcagccag   2460
ccagctgtgc acaagctgac caagcgcatc cccctgcgga gacaggtaac agtttcggcc   2520
gagtccagct cctccatgaa ctccaacacc cgctggtga ggataacaac gcgtctgtcc   2580
tcaacagcgg acacccgat gctagcaggg gtctccgagt atgagttgcc agaggatcca   2640
aagtgggaat tccccagaga taagctgacg ctgggcaaac ccctggggga aggttgcttc   2700
gggcaagtag tcatggctga agcagtggga atcgataaag acaaacccaa ggaggcggtc   2760
accgtggcag tgaagatgtt gaaagatgat gccacagaga aggacctgtc tgatctggta   2820
```

```
tcagagatgg agatgatgaa gatgattggg aaacataaga acattatcaa cctcctgggg    2880
gcctgcacgc aggatggacc tctctacgtc atagttgaat atgcatcgaa aggcaacctc    2940
cgggaatacc tccgagcccg gaggccacct ggcatggagt actcctatga cattaaccgt    3000
gtccccgagg agcagatgac cttcaaggac ttggtgtcct gcacctacca gctggctaga    3060
ggcatggagt acttggcttc ccaaaaatgt atccatcgag atttggctgc cagaaacgtg    3120
ttggtaacag aaaacaatgt gatgaagata gcagactttg gcctggccag ggatatcaac    3180
aacatagact actataaaaa gaccacaaat gggcgacttc cagtcaagtg gatggctcct    3240
gaagcccttt ttgatagagt ttacactcat cagagcgatg tctggtcctt cggggtgtta    3300
atgtgggaga tctttacttt aggggctca ccctacccag ggattcccgt ggaggaactt    3360
tttaagctgc tcaaagaggg acacaggatg gacaagccca ccaactgcac caatgaactg    3420
tacatgatga tgagggattg ctggcatgct gtaccctcac agagacccac attcaagcag    3480
ttggtcgaag acttggatcg aattctgact ctcacaacca atgaggaata cttggatctc    3540
acccagcctc tcgaacagta ttctcctagt taccccgaca caaggagctc ttgttcttca    3600
ggggacgatt ctgtgttttc tccagacccc atgccttatg aaccctgtct gcctcagtat    3660
ccacacataa acggcagtgt taaaacatga gtgaatgtgt cttcctgtcc ccaaacagga    3720
cagcaccagg aacctactta cactgagcag agaggctgtg cctccagagc ctgtgacacg    3780
cctccacttg tatatatgga tcagaggagt aaatagtggg aagcatattt gtcacgtgtg    3840
taaagattta tacagttgga aacatgttac ctaaccagga aaggaagact gtttcctgat    3900
aagtggacag ccgcaagcca ccatgccacc ctctctgacc caccatgtat gctggctgtg    3960
ccccagttgg actcaaggca gacaggtgtt ctgccttcct tgttaatttt gtaataattg    4020
gagaagatat atgtcagcac acacttacag agcacaaacg cagtatatag gtgctggatg    4080
tatgtaaata tattcaaatt atgtataaat atatattata tatttacaag gaattatttt    4140
ttgtattgat tttaaatgga tgtcctgatg cacctagaaa attggtctct cttttttta    4200 aatagatatt tgctaaatgc tgttcttaga gtttcttaat tttcaccgag cagaggtggg    4260
aaaatacttt tgctttcagg gaaaatggtg tcacattaat ttattaacga attggtaata    4320
tacgaaacga ttaatcatct atagttttt tttttttgta atttaagtgg catttctatg    4380
caggcagcac ggaggactag ttaatctatt gcttggactt aactggttat tggatccttt    4440
gagaagagaa atatttacga tatatgacta atttgggggg aaatggtgtt ttgatttatt    4500
tgtgtttcaa ctctgctgtc cgatgagcat gtctagacac cctaatgccc atgtttcaag    4560
aaacctgtta aactctgtca ccccagggta acaattaacc agacttccca agacaaatgg    4620
taccagcatc ctcatcccaa gatgccttaa tccacttctc tggagaacag acttccatgg    4680
gaatgatagc agggtcctct cgtccggcag ctggccttct gcccgggtta cacattcatc    4740
acgtttgcct tgcttctcag tgagttttaa taacagcttc agattcttca gcaccaagag    4800 cccctttgggg aatctccatc ctctcgaagg atggcaaaag cccagcatca ttcggttgag    4860
agtctgggac ctccttccat cttcttaagg gtttgcttct ggcttctacc cacttctgac    4920
aagacctcac ctcacaaaaa gatctggcct aatagctaca tccgacaaga taacgcttat    4980
tgttgatttc cgtattcaag tattgttttg ctttggatac gcccactcac tttgctacag    5040
tcatgcgaca tgtatgcaga ttacactgat tttatgtgtt ttggaattgg agaaagtatt    5100
taataaaacc tgttaatttt tatactgaca ataaaaatgt ttctacagat attaatgtta    5160
```

```
acaagacaaa ataaatgtca cgcagcttat tttttttaaaa aaaaaaaaaa aaaaaaaaaa    5220
aaa                                                                   5223
```

<210> SEQ ID NO 46
<211> LENGTH: 800
<212> TYPE: PRT
<213> ORGANISM: Mus musculus

<400> SEQUENCE: 46

```
Met Val Val Pro Ala Cys Val Leu Val Phe Cys Val Ala Val Ala
1               5                   10                  15

Gly Ala Thr Ser Glu Pro Pro Gly Pro Glu Gln Arg Val Arg Arg
                20                  25                  30

Ala Ala Glu Val Pro Gly Pro Glu Pro Ser Gln Gln Glu Gln Val Ala
            35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Val Gly Pro Asp Gly Thr Pro Tyr Val Thr Val Leu Lys
    290                 295                 300

Thr Ala Gly Ala Asn Thr Thr Asp Lys Glu Leu Glu Val Leu Ser Leu
305                 310                 315                 320

His Asn Val Thr Phe Glu Asp Ala Gly Glu Tyr Thr Cys Leu Ala Gly
                325                 330                 335

Asn Ser Ile Gly Phe Ser His His Ser Ala Trp Leu Val Val Leu Pro
            340                 345                 350

Ala Glu Glu Glu Leu Met Glu Thr Asp Glu Ala Gly Ser Val Tyr Ala
```

-continued

```
              355                 360                 365
Gly Val Leu Ser Tyr Gly Val Phe Phe Leu Phe Ile Leu Val Val
    370                 375                 380
Ala Ala Val Ile Leu Cys Arg Leu Arg Ser Pro Pro Lys Lys Gly Leu
385                 390                 395                 400
Gly Ser Pro Thr Val His Lys Val Ser Arg Phe Pro Leu Lys Arg Gln
                    405                 410                 415
Val Ser Leu Glu Ser Asn Ser Ser Met Asn Ser Asn Thr Pro Leu Val
                420                 425                 430
Arg Ile Ala Arg Leu Ser Ser Gly Glu Gly Pro Val Leu Ala Asn Val
                435                 440                 445
Ser Glu Leu Glu Leu Pro Ala Asp Pro Lys Trp Glu Leu Ser Arg Thr
    450                 455                 460
Arg Leu Thr Leu Gly Lys Pro Leu Gly Glu Gly Cys Phe Gly Gln Val
465                 470                 475                 480
Val Met Ala Glu Ala Ile Gly Ile Asp Lys Asp Arg Thr Ala Lys Pro
                    485                 490                 495
Val Thr Val Ala Val Lys Met Leu Lys Asp Asp Ala Thr Asp Lys Asp
                500                 505                 510
Leu Ser Asp Leu Val Ser Glu Met Glu Met Met Lys Met Ile Gly Lys
                515                 520                 525
His Lys Asn Ile Ile Asn Leu Leu Gly Ala Cys Thr Gln Gly Gly Pro
    530                 535                 540
Leu Tyr Val Leu Val Glu Tyr Ala Ala Lys Gly Asn Leu Arg Glu Phe
545                 550                 555                 560
Leu Arg Ala Arg Arg Pro Pro Gly Met Asp Tyr Ser Phe Asp Ala Cys
                565                 570                 575
Arg Leu Pro Glu Glu Gln Leu Thr Cys Lys Asp Leu Val Ser Cys Ala
                580                 585                 590
Tyr Gln Val Ala Arg Gly Met Glu Tyr Leu Ala Ser Gln Lys Cys Ile
                595                 600                 605
His Arg Asp Leu Ala Ala Arg Asn Val Leu Val Thr Glu Asp Asn Val
    610                 615                 620
Met Lys Ile Ala Asp Phe Gly Leu Ala Arg Asp Val His Asn Leu Asp
625                 630                 635                 640
Tyr Tyr Lys Lys Thr Thr Asn Gly Arg Leu Pro Val Lys Trp Met Ala
                645                 650                 655
Pro Glu Ala Leu Phe Asp Arg Val Tyr Thr His Gln Ser Asp Val Trp
                660                 665                 670
Ser Phe Gly Val Leu Leu Trp Glu Ile Phe Thr Leu Gly Gly Ser Pro
                675                 680                 685
Tyr Pro Gly Ile Pro Val Glu Glu Leu Phe Lys Leu Leu Lys Glu Gly
            690                 695                 700
His Arg Met Asp Lys Pro Ala Ser Cys Thr His Asp Leu Tyr Met Ile
705                 710                 715                 720
Met Arg Glu Cys Trp His Ala Val Pro Ser Gln Arg Pro Thr Phe Lys
                    725                 730                 735
Gln Leu Val Glu Asp Leu Asp Arg Ile Leu Thr Val Thr Ser Thr Asp
                740                 745                 750
Glu Tyr Leu Asp Leu Ser Val Pro Phe Glu Gln Tyr Ser Pro Gly Gly
            755                 760                 765
Gln Asp Thr Pro Ser Ser Ser Ser Ser Gly Asp Asp Ser Val Phe Thr
    770                 775                 780
```

His Asp Leu Leu Pro Pro Gly Pro Pro Ser Asn Gly Gly Pro Arg Thr
785                 790                 795                 800

<210> SEQ ID NO 47
<211> LENGTH: 4232
<212> TYPE: DNA
<213> ORGANISM: Mus musculus

<400> SEQUENCE: 47

| | | | | | |
|---|---|---|---|---|---|
| tcggggcgtg | gcgggagcac | cccccaaccc | ccgcccgggc | tgctgcgcgc | cgggcagccc | 60 |
| cagttcagtg | cactgtggca | gcggggggtgg | cgggagcagc | tggcgccgtg | cgatccactc | 120 |
| cggcgggggg | actcagtggt | gggcggccgg | ccactgggac | agaggagacc | ctggaaaagc | 180 |
| gggccgagag | acgagccgc | gcgtgtctcc | acagaggcgt | tctcccaccg | cgcgccggagc | 240 |
| cgggcgtggg | gggttgcagc | atgcccgcgc | gcgctgcttg | aggacgccgc | ggcccccgct | 300 |
| ctggagccat | ggtagtcccg | gcctgcgtgc | tagtgttctg | cgtggcggtc | gtggctggag | 360 |
| ctacttccga | gcctcctggt | ccagagcagc | gagttgtgcg | gagagcggca | gaggttccag | 420 |
| ggcctgaacc | tagccagcag | gagcaggtgg | ccttcggcag | tggggacacc | gtggagctga | 480 |
| gctgccatcc | tcctggaggt | gcccccacag | ggcccacggt | ctgggctaag | gatggtacag | 540 |
| gtctggtggc | ctcccaccgc | atcctggtgg | ggcctcagag | gctgcaagtg | ctaaatgcct | 600 |
| cccacgaaga | tgcaggggtc | tacagctgcc | agcaccggct | cactcggcgt | gtgctgtgcc | 660 |
| acttcagtgt | gcgtgtaaca | gatgctccat | cctcaggaga | tgacgaagat | ggggaggacg | 720 |
| tggctgaaga | cacaggggct | ccttattgga | ctcgcccgga | gcgaatggat | aagaaactgc | 780 |
| tggctgtgcc | agccgcaaac | actgtccgct | tccgctgccc | agctgctggc | aaccctaccc | 840 |
| cctccatctc | ctggctgaag | aatggcaaag | aattccgagg | ggagcatcgc | attggggggca | 900 |
| tcaagctccg | gcaccagcag | tggagcttgg | tcatggaaag | tgtggtaccc | tccgatcgtg | 960 |
| gcaactatac | ctgtgtagtt | gagaacaagt | ttggcagcat | ccggcagaca | tacacactgg | 1020 |
| atgtgctgga | gcgctcccca | caccggccca | tcctgcaggc | tgggctgccg | ccaaccagca | 1080 |
| cagccattct | aggcagtgac | gtggagttcc | actgcaaggt | gtacagcgat | gcacagccac | 1140 |
| acatccagtg | gctgaagcac | gtggaagtga | acggcagcaa | ggtgggccct | gacggcacgc | 1200 |
| cctacgtcac | tgtactcaag | actgcaggcg | ctaacaccac | cgacaaggag | ctagaggttc | 1260 |
| tgtccttgca | caatgtcacc | tttgaggacg | cgggggagta | cacctgcctg | gcgggcaatt | 1320 |
| ctattgggtt | ttcccatcac | tctgcgtggc | tggtggtgct | gccagctgag | gaggagctga | 1380 |
| tggaaactga | tgaggctggc | agcgtgtacg | caggcgtcct | cagctacggg | gtggtcttct | 1440 |
| tcctcttcat | cctggtggtg | gcagctgtga | tactctgccg | cctgcgcagt | cccccaaaga | 1500 |
| agggcttggg | ctcgcccacc | gtgcacaagg | tctctcgctt | cccgcttaag | cgacaggtgt | 1560 |
| ccttggaatc | taactcctct | atgaactcca | acacaccct | tgtccggatt | gcccggctgt | 1620 |
| cctcaggaga | aggtcctgtt | ctggccaatg | tttctgaact | tgagctgcct | gctgacccca | 1680 |
| agtgggagct | atccaggacc | cggctgacac | ttggtaagcc | tcttggagaa | ggctgctttg | 1740 |
| gacaggtggt | catggcagaa | gctattggca | tcgacaagga | ccgtactgcc | aagcctgtca | 1800 |
| ccgtggccgt | gaagatgctg | aaagatgatg | cgactgacaa | ggacctgtcg | gacctggtat | 1860 |
| ctgagatgga | gatgatgaaa | atgattggca | agcacaagaa | catcattaac | ctgctggggg | 1920 |
| cgtgcacaca | gggtgggccc | ctgtatgtgc | tggtggagta | cgcagccaag | ggcaatctcc | 1980 |
| gggagttcct | tcgggcgcgg | cggcctccag | gcatggacta | ctcctttgat | gcctgcaggc | 2040 |

```
tgccagagga acagctcacc tgcaaggatc tagtgtcctg tgcctaccag gtggcacggg   2100
gcatggaata cttggcttct cagaagtgta ttcacagaga cttggctgcc agaaacgtcc   2160
tggtgaccga ggacaatgtg atgaagattg cggactttgg cctggctcga gatgtgcaca   2220
acctggacta ctacaagaag accacaaatg gccggctacc tgtgaagtgg atggcaccag   2280 aggcccttt tgaccgagtc tacacccacc agagtgatgt ttggtctttt ggtgtcctcc   2340
tctgggagat ctttacgctg gggggctcac cgtatcctgg catcccagtg gaagagcttt   2400
tcaagctgtt gaaagagggc caccgcatgg acaagccagc cagctgcaca catgacctgt   2460
acatgatcat gcgggaatgt tggcatgcgg tgccttcaca gaggcccacc ttcaagcagt   2520
tggtagagga tttagaccgc atcctcactg tgacatcaac cgacgagtac ttggacctct   2580
ccgtgccgtt tgagcagtac tcgccaggtg gccaggacac gcctagctcc agctcgtccg   2640
gagatgactc ggtgttcacc catgacctgc tacccccagg tccacccagt aacgggggac   2700
ctcggacgtg aagggccaac agtcccacag accaagcccc aggcaatgtt tacgcggacc   2760
ctagcccgcc ctgctactgc tggtgtgcag tggaccctag ccagcccagt gcaatgggcc   2820
aacagtagac aagacttcct gcgtgtttat ccttggctcc tgggtgcaga ggccccttgg   2880
gaacatgcac tgctgtagag taatctcctg actggccagg gccaggagca ccaaacaaga   2940
atgtaagagg cccaccctgt gcaaccctgg ggttctggcc ctctcatttc ccactgctac   3000
cttccaggga ccattgtgga gagggctaga ctccatgtcc agagtgggcc ttggccttct   3060
tggtgcccca agctgagcct acagggaggc tctgctctgt gtggcaaacc tctctcctac   3120 atggcaccctt gtgcctgggg gtgtcatagc tcgacatctc caggctgcct gctttccacc   3180
ctgcccctca gagacaaatt acgggtacct gaagggggggg cataatgtct atcagaaagg   3240
tttattccag aggaaaatgt acatttatat aaatagatgt tgtgtatgat ataaatatat   3300
acatacatat atataagaat atctatatgg aaaaaggcaa agttgaggcc caagggagca   3360
agatactcca tgggtctcac taggaaactg gcaagagcag gctgagaagc aagggctttt   3420
tctggcacgg cagttttgtt tgtactggac ctgtatattt gtaaagctat ttatcaaccc   3480
ccagagcgcc agtccccgac cccaggttca tagcgtttag tcccagggta ttgcagccat   3540
cttaagttgt aacttattaa cagcggaaga ggttcatgct ggatttaggg aattgctgag   3600
aacgtgcgtc tggcctccac caggctggcc gtggccccttt ggcgcttgaa tggctctcct   3660
agtcagagct ggctccaggg agcatttttct gttgcctttg gccctctttt gtgggggatt   3720
agatttatat aggaactttc tttaggagat gtttaaaaat tttaaggtga actggtattt   3780
ttcatacaga ttattctaat tgctatgtat tccaggcagg agcctgtgcc cagggaaggg   3840
ctggccctgc aagaaggttc agatgttaat agttatctgt tacaagttta tctatctata   3900
atttattgag tttttacaag ttgttttgct gtaggcttaa cacttcctat gcagtgcttc   3960
tagactttta tagcctagac tgctaccttt caaagcttgg gagacagtgg tgaatgcaat   4020
tttgttactt ttgtactgtc actgggccct aggcttgggt ggctgtccct tgcctgtcaa   4080
ccagcagggt caggacagtg gctcagggtg actttcttgg ggcctagcac atggtttgtc   4140
agcccacact ggcagatgtg gttttgttaa cacaaccaac ttactttcca aaaaataaag   4200
agataactgg ttccaaaaaa aaaaaaaaaa aa                                 4232
```

<210> SEQ ID NO 48
<211> LENGTH: 799
<212> TYPE: PRT

<213> ORGANISM: Mus musculus

<400> SEQUENCE: 48

```
Met Trp Leu Leu Leu Ala Leu Leu Ser Ile Phe Gln Gly Thr Pro Ala
1               5                   10                  15

Leu Ser Leu Glu Ala Ser Glu Glu Met Glu Gln Glu Pro Cys Leu Ala
            20                  25                  30

Pro Ile Leu Glu Gln Gln Glu Gln Val Leu Thr Val Ala Leu Gly Gln
        35                  40                  45

Pro Val Arg Leu Cys Cys Gly Arg Thr Glu Arg Gly Arg His Trp Tyr
    50                  55                  60

Lys Glu Gly Ser Arg Leu Ala Ser Ala Gly Arg Val Arg Gly Trp Arg
65                  70                  75                  80

Gly Arg Leu Glu Ile Ala Ser Phe Leu Pro Glu Asp Ala Gly Arg Tyr
                85                  90                  95

Leu Cys Leu Ala Arg Gly Ser Met Thr Val Val His Asn Leu Thr Leu
            100                 105                 110

Leu Met Asp Asp Ser Leu Thr Ser Ile Ser Asn Asp Glu Asp Pro Lys
        115                 120                 125

Thr Leu Ser Ser Ser Ser Ser Gly His Val Tyr Pro Gln Gln Ala Pro
    130                 135                 140

Tyr Trp Thr His Pro Gln Arg Met Glu Lys Lys Leu His Ala Val Pro
145                 150                 155                 160

Ala Gly Asn Thr Val Lys Phe Arg Cys Pro Ala Ala Gly Asn Pro Met
                165                 170                 175

Pro Thr Ile His Trp Leu Lys Asp Gly Gln Ala Phe His Gly Glu Asn
            180                 185                 190

Arg Ile Gly Gly Ile Arg Leu Arg His Gln His Trp Ser Leu Val Met
        195                 200                 205

Glu Ser Val Val Pro Ser Asp Arg Gly Thr Tyr Thr Cys Leu Val Glu
    210                 215                 220

Asn Ser Leu Gly Ser Ile Arg Tyr Ser Tyr Leu Leu Asp Val Leu Glu
225                 230                 235                 240

Arg Ser Pro His Arg Pro Ile Leu Gln Ala Gly Leu Pro Ala Asn Thr
                245                 250                 255

Thr Ala Val Val Gly Ser Asp Val Glu Leu Leu Cys Lys Val Tyr Ser
            260                 265                 270

Asp Ala Gln Pro His Ile Gln Trp Leu Lys His Val Val Ile Asn Gly
        275                 280                 285

Ser Ser Phe Gly Ala Asp Gly Phe Pro Tyr Val Gln Val Leu Lys Thr
    290                 295                 300

Thr Asp Ile Asn Ser Ser Glu Val Glu Val Leu Tyr Leu Arg Asn Val
305                 310                 315                 320

Ser Ala Glu Asp Ala Gly Glu Tyr Thr Cys Leu Ala Gly Asn Ser Ile
                325                 330                 335

Gly Leu Ser Tyr Gln Ser Ala Trp Leu Thr Val Leu Pro Glu Glu Asp
            340                 345                 350

Leu Thr Trp Thr Thr Ala Thr Pro Glu Ala Arg Tyr Thr Asp Ile Ile
        355                 360                 365

Leu Tyr Val Ser Gly Ser Leu Val Leu Leu Leu Leu Leu Leu Leu Ala
    370                 375                 380

Gly Val Tyr His Arg Gln Val Ile Arg Gly His Tyr Ser Arg Gln Pro
385                 390                 395                 400
```

```
Val Thr Ile Gln Lys Leu Ser Arg Phe Pro Leu Ala Arg Gln Phe Ser
                405                 410                 415

Leu Glu Ser Arg Ser Ser Gly Lys Ser Ser Leu Ser Leu Val Arg Gly
            420                 425                 430

Val Arg Leu Ser Ser Ser Gly Pro Pro Leu Leu Thr Gly Leu Val Asn
        435                 440                 445

Leu Asp Leu Pro Leu Asp Pro Leu Trp Glu Phe Pro Arg Asp Arg Leu
    450                 455                 460

Val Leu Gly Lys Pro Leu Gly Glu Gly Cys Phe Gly Gln Val Val Arg
465                 470                 475                 480

Ala Glu Ala Phe Gly Met Asp Pro Ser Arg Pro Asp Gln Thr Ser Thr
                485                 490                 495

Val Ala Val Lys Met Leu Lys Asp Asn Ala Ser Asp Lys Asp Leu Ala
            500                 505                 510

Asp Leu Val Ser Glu Met Glu Val Met Lys Leu Ile Gly Arg His Lys
        515                 520                 525

Asn Ile Ile Asn Leu Leu Gly Val Cys Thr Gln Glu Gly Pro Leu Tyr
    530                 535                 540

Val Ile Val Glu Cys Ala Ala Lys Gly Asn Leu Arg Glu Phe Leu Arg
545                 550                 555                 560

Ala Arg Arg Pro Pro Gly Pro Asp Leu Ser Pro Asp Gly Pro Arg Ser
                565                 570                 575

Ser Glu Gly Pro Leu Ser Phe Pro Ala Leu Val Ser Cys Ala Tyr Gln
            580                 585                 590

Val Ala Arg Gly Met Gln Tyr Leu Glu Ser Arg Lys Cys Ile His Arg
        595                 600                 605

Asp Leu Ala Ala Arg Asn Val Leu Val Thr Glu Asp Asp Val Met Lys
    610                 615                 620

Ile Ala Asp Phe Gly Leu Ala Arg Gly Val His His Ile Asp Tyr Tyr
625                 630                 635                 640

Lys Lys Thr Ser Asn Gly Arg Leu Pro Val Lys Trp Met Ala Pro Glu
                645                 650                 655

Ala Leu Phe Asp Arg Val Tyr Thr His Gln Ser Asp Val Trp Ser Phe
            660                 665                 670

Gly Ile Leu Leu Trp Glu Ile Phe Thr Leu Gly Gly Ser Pro Tyr Pro
        675                 680                 685

Gly Ile Pro Val Glu Glu Leu Phe Ser Leu Leu Arg Glu Gly His Arg
    690                 695                 700

Met Glu Arg Pro Pro Asn Cys Pro Ser Glu Leu Tyr Gly Leu Met Arg
705                 710                 715                 720

Glu Cys Trp His Ala Ala Pro Ser Gln Arg Pro Thr Phe Lys Gln Leu
                725                 730                 735

Val Glu Ala Leu Asp Lys Val Leu Leu Ala Val Ser Glu Glu Tyr Leu
            740                 745                 750

Asp Leu Arg Leu Thr Phe Gly Pro Phe Ser Pro Ser Asn Gly Asp Ala
        755                 760                 765

Ser Ser Thr Cys Ser Ser Ser Asp Ser Val Phe Ser His Asp Pro Leu
    770                 775                 780

Pro Leu Glu Pro Ser Pro Phe Pro Phe Ser Asp Ser Gln Thr Thr
785                 790                 795

<210> SEQ ID NO 49
<211> LENGTH: 3146
<212> TYPE: DNA
```

<213> ORGANISM: Mus musculus

<400> SEQUENCE: 49

```
gacattcctg gctcttcggc ccggggcgga ggagctccgg gcgggtgagt gtgccagccc      60
tgccgggatc gtgacccgcg cgcgcgggag ccgggcggcg gaggagccag gaaggtggtc     120
agtgggaagt ctggccctga tcctgagatc agctggaagg aaatgtggct gctcttggcc     180
ctgttgagca tctttcaggg gacaccagct ttgtcccttg aggcctctga ggaaatggag     240
caggagccct gcctagcccc aatcctggag cagcaagagc aggtgttgac ggtggccctg     300
gggcagcctg tgaggctgtg ctgtgggcgc accgagcgtg gtcgtcactg gtacaaagag     360
ggcagccgcc tagcatctgc tgggcgagta cggggttgga gaggccgcct ggagatcgcc     420
agcttccttc ctgaggatgc tggccgatac ctctgcctgg cccgtggctc catgaccgtc     480
gtacacaatc ttacgttgct tatggatgac tccttaacct ccatcagtaa tgatgaagac     540
cccaagacac tcagcagctc ctcgagtggt catgtctacc acagcaagc accctactgg     600
acacaccccc aacgcatgga gaagaaactg catgcagtgc ctgccgggaa tactgtcaaa     660
ttccgctgtc cagctgcagg gaaccccatg cctaccatcc actggctcaa ggatggacag     720
gccttccacg gggagaatcg tattggaggc attcggctgc gccaccaaca ctggagcctg     780
gtgatggaaa gtgtggtacc ctcggaccgt ggcacataca catgccttgt ggagaactct     840
ctgggtagca ttcgctacag ctatctcctg gatgtgctgg agcggtcccc gcaccggccc     900
atcctgcagg cggggctccc agccaacacc acagctgtgg ttggcagcga tgtggagcta     960
ctctgcaagg tgtacagcga cgcccagccc cacatacagt ggctgaaaca cgtcgtcatc    1020
aacggcagca gcttcggcgc cgacggtttc ccctacgtac aagtcctgaa gacaacagac    1080
atcaatagct cggaggtaga ggtcttgtat ctgaggaacg tgtccgctga ggatgcagga    1140
gagtatacct gtctggcggg caactccatc ggccttttcct accagtcagc gtggctcacg    1200
gtgctgccag aggaagacct cacgtggaca acagcaaccc ctgaggccag atacacagat    1260
atcatcctgt atgtatcagg ctcactggtt ctgcttgtgc tcctgctgct ggccggggtg    1320
tatcatcggc aagtcatccg tggccactac tctcgccagc ctgtcactat acaaaagctg    1380
tcccgtttcc cttttggcccg acagttctct ttggagtcga ggtcctctgg caagtcaagt    1440
ttgtccctgg tgcgaggtgt ccgtctctcc tccagcggcc cgcccttgct cacgggcctt    1500
gtgaatctag acctgcctct cgatccgctt tgggaattcc cccgggacag gttggtgctc    1560
ggaaagcccc tgggtgaggg ctgctttggg caagtggttc gtgcagaggc ctttggtatg    1620
gatccctccc ggcccgacca aaccagcacc gtggctgtga agatgctgaa agacaatgcc    1680
tccgacaagg atttggcaga cctggtctcc gagatggagg tgatgaagct aatcggaaga    1740
cacaagaaca tcatcaacct gctgggtgtc tgcactcagg aagggcccct gtacgtgatt    1800
gtggaatgtg ccgccaaggg aaaccttcgg gaattcctcc gtgcccggcg ccccccaggc    1860
cctgatctca gccctgatgg acctcggagc agcgaaggac cactctcctt cccggcccta    1920
gtctcctgtg cctaccaggt ggcccgaggc atgcagtatc tggagtctcg gaagtgcatc    1980
caccgggacc tggctgcccg aaatgtgctg gtgaccgagg atgatgtgat gaagatcgct    2040
gactttgggc tggcacgtgg tgtccaccac attgactact ataagaaaac cagcaacggc    2100
cgcctgccag tcaaatggat ggctccagag gcattgttcg accgcgtgta cacacaccag    2160
agtgacgtgt ggtctttcgg gatcctgctg tgggaaatct tcaccctcgg ggctccccca    2220
tacccctggca ttccggtgga ggagctcttc tcactgctgc gagaggggca caggatggag    2280
```

-continued

```
cggcccccaa actgccctc agagctgtat gggctaatga gggagtgctg gcacgcagcc    2340
ccatctcaga ggcctacttt taagcagctg gtggaagctc tggacaaggt cctgctggct    2400
gtctctgaag agtaccttga cctccgcctg acctttggac cctttctcc ctccaatggg     2460 gatgccagca gcacctgctc ctccagtgac tcggttttca gccacgaccc tttgcccctc    2520
gagccaagcc ccttccctttt ctctgactcg cagacgacat gagccgggga gcagcaatgt   2580
tgtatgggct acgcggccca tggccgtggg tctcctcgct gagctgcaac ctgatgcatc    2640
gacatttaat gttggcagtg tcaggcctct gacttgagac tactgctgtc gcagatcctc    2700
tctctggccc tgttttgggg agggccattc ttggtcctaa ggttcatagt tgaggccttc    2760
tgttccagcc ttatgctccc atctcagagt tcaactctca tctcaagatc atggccttgc    2820
ccttggactc atcctcagag aagttaagca ttaaggcctt ggcacgcagc ctccgtctcc    2880
ggggctctcc gggactagct gcaaaactta tgctctaaac atttctagtt cccccaaaca    2940
acctagaggc cttgggactt cacatccccc agcacacaag cctcaccacc ccctgccatc    3000 cccctccat tgcttgttcc agcatcttgg tgaaggggc atcagctctg gtgtccctga     3060
gagacgagaa gcctgtggga acgacagaag aacatggcat ttttataaat tatttttttg    3120
aaataaatct ctgtgtgcct ggtggc                                         3146
```

```
<210> SEQ ID NO 50
<211> LENGTH: 158
<212> TYPE: PRT
<213> ORGANISM: Gallus gallus

<400> SEQUENCE: 50
```

```
Met Ala Gly Ala Ala Gly Ser Ile Thr Thr Leu Pro Ala Leu Pro
1               5                   10                  15

Asp Asp Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140

Gly Gln Lys Ala Ile Leu Phe Leu Pro Met Ser Ala Lys Ser
145                 150                 155
```

```
<210> SEQ ID NO 51
<211> LENGTH: 574
<212> TYPE: DNA
<213> ORGANISM: Gallus gallus

<400> SEQUENCE: 51
gaggctggac ggccgcggca gggggcgagc ccgcccggcg ctggcggcgg cggccggcgg    60
```

```
gggcccggggg cggcggggag ccgccggggc cggcgcatg gcggcggggg cggcgggag    120 catcaccacg ctgccggcgc tgcccgacga cggggggcggc ggcgcttttc ccccgggca    180 cttcaaggac cccaagcggc tctactgcaa gaacggcggc ttcttcctgc gcatcaaccc    240
cgacggcagg gtggacggcg tccgcgagaa gagccgatccg cacatcaaac tgcagcttca    300
agcagaagaa agaggagtag tatcaatcaa aggcgtaagt gcaaaccgct ttctggctat    360
gaaggaggat ggcagattgc tggcactgaa atgtgcaaca gaggaatgtt tcttttttcga   420 gcgcttggaa tctaataact ataacactta ccggtcacgg aagtactctg attggtatgt    480
ggcactgaaa aggactggac agtacaagcc cggaccaaaa actggacctg gacagaaagc    540
tatccttttt cttccaatgt ctgctaaaag ctga                                574
```

<210> SEQ ID NO 52
<211> LENGTH: 819
<212> TYPE: PRT
<213> ORGANISM: Gallus gallus

<400> SEQUENCE: 52

```
Met Phe Thr Trp Arg Cys Leu Ile Leu Trp Ala Val Leu Val Thr Ala
1               5                  10                  15

Thr Leu Ser Ala Ala Arg Pro Ala Pro Thr Leu Pro Asp Gln Ala Leu
            20                  25                  30

Pro Lys Ala Asn Ile Glu Val Glu Ser His Ser Ala His Pro Gly Asp
        35                  40                  45

Leu Leu Gln Leu Arg Cys Arg Leu Arg Asp Asp Val Gln Ser Ile Asn
    50                  55                  60

Trp Val Arg Asp Gly Val Gln Leu Pro Glu Asn Asn Arg Thr Arg Ile
65                  70                  75                  80

Thr Gly Glu Glu Val Glu Val Arg Asp Ala Val Pro Glu Asp Ser Gly
                85                  90                  95

Leu Tyr Ala Cys Met Thr Asn Ser Pro Ser Gly Ser Glu Thr Thr Tyr
            100                 105                 110

Phe Ser Val Asn Val Ser Asp Ala Leu Pro Ser Ala Glu Asp Asp Asp
        115                 120                 125

Asp Glu Asp Asp Ser Ser Ser Glu Glu Lys Glu Ala Asp Asn Thr Lys
    130                 135                 140

Pro Asn Gln Ala Val Ala Pro Tyr Trp Thr Tyr Pro Glu Lys Met Glu
145                 150                 155                 160

Lys Lys Leu His Ala Val Pro Ala Ala Lys Thr Val Lys Phe Lys Cys
                165                 170                 175

Pro Ser Gly Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Lys Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Val Cys Lys Val Tyr Ser Asp Pro Gln Pro His Ile Gln Trp Leu
        275                 280                 285
```

```
Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Ile Ser His His Ser Ala
                340                 345                 350

Trp Leu Thr Val Leu Glu Ala Thr Glu Gln Ser Pro Ala Met Met Thr
                355                 360                 365

Ser Pro Leu Tyr Leu Glu Ile Ile Ile Tyr Cys Thr Gly Ala Phe Leu
370                 375                 380

Ile Ser Cys Met Val Val Thr Val Ile Ile Tyr Lys Met Lys Ser Thr
385                 390                 395                 400

Thr Lys Lys Thr Asp Phe Asn Ser Gln Leu Ala Val His Lys Leu Ala
                405                 410                 415

Lys Ser Ile Pro Leu Arg Arg Gln Val Thr Val Ser Ala Asp Ser Ser
                420                 425                 430

Ser Ser Met Asn Ser Gly Val Met Leu Val Arg Pro Ser Arg Leu Ser
                435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Ile Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
                515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Met Glu Tyr Cys Tyr Asn Pro Thr Arg Ile Pro Glu Glu Gln
                580                 585                 590

Leu Ser Phe Lys Asp Leu Val Ser Cys Ala Tyr Gln Val Ala Arg Gly
                595                 600                 605

Met Glu Tyr Leu Ala Ser Lys Lys Cys Ile His Arg Asp Leu Ala Ala
610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
                660                 665                 670

Arg Ile Tyr Thr His Gln Ser Asp Val Trp Ser Phe Gly Val Leu Leu
                675                 680                 685

Trp Glu Ile Phe Thr Leu Gly Gly Ser Pro Tyr Pro Gly Val Pro Val
690                 695                 700
```

```
Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Met Thr Ser Asn Gln Glu Tyr Leu Asp Leu Ser
        755                 760                 765

Val Pro Leu Asp Gln Tyr Ser Pro Gly Phe Pro Ala Thr Arg Ser Ser
    770                 775                 780

Thr Cys Ser Ser Gly Glu Asp Ser Val Phe Ser His Asp Pro Leu Pro
785                 790                 795                 800

Asp Glu Pro Cys Leu Pro Arg Cys Pro Pro His Ser His Gly Ala Leu
                805                 810                 815

Lys Arg His

<210> SEQ ID NO 53
<211> LENGTH: 2925
<212> TYPE: DNA
<213> ORGANISM: Gallus gallus

<400> SEQUENCE: 53
cgccccatgg aggggcggtt gagcgcagtc gctgagcagt agccgcagca gtgggatgtt        60
tacctggagg tgcctcatcc tttgggctgt gctggtcaca gccacgctgt ctgctgccag       120
accggccccc acgctgcccg accaagctct gcccaaagcg aacatcgagg tggagtccca       180
ctcggcgcac cccggcgatc tcctccagct gcgctgccgg ctgcgcgatg acgtgcagag       240
catcaactgg gtgcgtgatg gagtgcagct gcccgagaac aaccgcacgc gcatcaccgg       300
cgaggaggta gaggtgcggg acgcggtgcc cgaggactcg gggctctatg cctgcatgac       360
caacagcccc tcggggagcg agaccaccta cttctccgtc aacgtctcag acgcactccc       420
ttctgcagag gatgatgatg atgaagatga ttcctcctcg gaggagaagg aggcggataa       480
caccaagccg aaccaggctg tagctcctta ctggacctat cccgagaaga tggagaagaa       540
gctgcatgcc gtcccgctg ccaaaacagt gaaattcaag tgcccctcag gtgggacgcc       600
caaccccacg ctgcgctggc tgaagaacgg caaggagttc aagcctgacc accgcatcgg       660
ggggtacaag gtccgctatg ccacctggag catcatcatg gactcggtgg tgccatcaga       720
taagggcaac tacacgtgca tcgtggagaa caaatacggg agcatcaacc acacctacca       780
gctggatgtc gtggagcgct ccccgcatcg gcccatcctg caggcagggc tccccgccaa       840
caaaacggtg gccctgggca gcaacgtgga gtttgtctgc aaggtctaca gcgacccgca       900
gccccacatc cagtggctga acacatcga ggtgaacggc agcaagatcg ccccgacaa       960 cttgccctac gtgcagatcc tgaagacggc tggcgttaac acgacagaca agagatggaa      1020
agtccttcac ttaaggaatg tctcatttga ggatgctggg gagtatacat gtttggcggg      1080
taattctatt gggatctccc atcactctgc atggttgaca gttctcgaag ctactgagca      1140
gtcaccagcc atgatgacgt ccccctcta cctggagatc atcatttact gcaccggcgc      1200
cttcctcatc tcctgcatgg tggtgacagt catcatctac aagatgaaga gcaccaccaa      1260
gaagacagac ttcaacagcc agctggccgt gcacaagctg gccaagagca tcccactgcg      1320
cagacaggta acagtgtcag cagattccag ctcctccatg aactcgggtg tgatgttggt      1380
gcggccctca cggctctcct ccagcggaac ccccatgctg gccggcgtct ccgagtatga      1440
```

-continued

```
gctgcccgag gacccgcgct gggagctgcc acgggacagg ctgatcctgg gcaagccgct   1500
gggagaaggc tgctttgggc aggtggtgct ggcggaggcc atcggcctgg acaaggacaa   1560
gccaaaccgc gtcaccaaag tggctgtaaa gatgctcaag tccgatgcca cagagaagga   1620
cctgtccgac ctcatctccg agatggagat gatgaagatg atcggcaagc acaagaacat   1680
catcaacctg ctgggtgcct gcacgcagga cgggcccctc tatgtcatcg tggagtacgc   1740
cagcaaaggc aacctgcgtg agtacctgca ggcacgccgc ccaccgggca tggagtactg   1800
ctacaacccc acacgcatcc ccgaggagca gctctccttc aaggacctgg tgtcctgtgc   1860
gtaccaggtg gcgcgcggca tggagtacct ggcctccaaa aagtgcatcc acagggacct   1920
ggcggccagg aacgtgctgg tgaccgagga caacgtgatg aagatcgctg acttcgggct   1980
ggcccgcgac atccaccaca tcgattacta caagaagacg acaaacggcc gcttgccggt   2040
gaagtggatg gccccggagg ctctgttcga ccgaatatac acccatcaga gtgatgtttg   2100
gtcgttcggt gtgctgctgt gggagatctt cacgttgggt ggttcgccct accccggcgt   2160
gcccgtggag gagctcttca agctgctgaa ggaaggccac aggatggaca agcccagcaa   2220
ctgcaccaac gagctgtaca tgatgatgcg cgactgctgg cacgccgtgc cctcccagcg   2280
ccccaccttc aagcagctgg tggaggacct ggacaggatc gtggccatga cctccaatca   2340
ggagtacctg gacctgtcgg tgccgttgga tcagtactcg cccggcttcc cggccacgcg   2400
cagctccacc tgctcctcgg gggaggactc ggtgttctcc cacgacccgc tgcccgacga   2460
gccctgcctg ccgcgctgcc ccccgcacag ccacggagcg ctgaagcggc actgaggctc   2520
cgcacgcagc tgtgcccccc cgggcaccac caccgcaggg aactgcccaa agctttcggc   2580
tgctgttggg ctgttggtcg gctctttttt tttatcaccc atttaaaccc ttcccacgag   2640
gtctgtgctt ggacatcccc acgtggcggt gccgccgtgt ccctatgggg ccgatgcgcg   2700
ctgtgagcat cgcatcccag cgctgcccca acccacacgt gtgggtgtg cagcacacgg   2760
ggccgccccg gggatcagcg ctaggacaga agtcccgtgt acatagctaa atatgtata   2820
aatatgaata tatatttaca tgtctttta aaagggtggt taccagagct gtgccaggct   2880
gggtagggag gtgctggtgg ctggtagata tcagttgcta tatat             2925
```

<210> SEQ ID NO 54
<211> LENGTH: 823
<212> TYPE: PRT
<213> ORGANISM: Gallus gallus

<400> SEQUENCE: 54

```
Met Val Ser Trp Asp Ser Gly Cys Leu Ile Cys Leu Val Val Val Thr
 1               5                  10                  15
Met Ala Gly Leu Ser Leu Ala Arg Pro Ser Phe Asn Leu Val Val Glu
            20                  25                  30
Asp Ala Thr Leu Glu Pro Glu Glu Pro Pro Thr Lys Tyr Gln Ile Ser
        35                  40                  45
Gln Pro Asp Val His Ser Ala Leu Pro Gly Glu Pro Leu Glu Leu Arg
    50                  55                  60
Cys Gln Leu Lys Asp Ala Val Met Ile Ser Trp Thr Lys Asp Gly Val
65                  70                  75                  80
Pro Leu Gly Pro Asp Asn Arg Thr Val Ile Ile Gly Glu Tyr Leu Gln
                85                  90                  95
Ile Lys Asp Ala Ser Pro Arg Asp Ser Gly Leu Tyr Ala Cys Thr Ala
           100                 105                 110
```

```
Ile Arg Thr Leu Asp Ser Asp Thr Leu Tyr Phe Ile Val Asn Val Thr
            115                 120                 125

Asp Ala Leu Ser Ser Gly Asp Glu Asp Asn Asp Gly Ser Glu
        130                 135                 140

Asp Phe Val Asn Asp Ser Asn Gln Met Arg Ala Pro Tyr Trp Thr His
145                 150                 155                 160

Thr Asp Lys Met Glu Lys Arg Leu His Ala Val Pro Ala Ala Asn Thr
                165                 170                 175

Val Lys Phe Arg Cys Pro Ala Met Gly Asn Pro Thr Pro Thr Met Arg
            180                 185                 190

Trp Leu Lys Asn Gly Lys Glu Phe Lys Gln Glu His Arg Ile Gly Gly
            195                 200                 205

Tyr Lys Val Arg Asn Gln His Trp Ser Leu Ile Met Glu Ser Val Val
        210                 215                 220

Pro Ser Asp Lys Gly Asn Tyr Thr Cys Ile Val Glu Asn Gln Tyr Gly
225                 230                 235                 240

Ser Ile Asn His Thr Tyr His Leu Asp Val Val Glu Arg Ser Pro His
                245                 250                 255

Arg Pro Ile Leu Gln Ala Gly Leu Pro Ala Asn Ala Ser Ala Val Val
            260                 265                 270

Gly Gly Asp Val Glu Phe Val Cys Lys Val Tyr Ser Asp Ala Gln Pro
        275                 280                 285

His Ile Gln Trp Ile Lys His Val Glu Arg Asn Gly Ser Lys Tyr Gly
        290                 295                 300

Pro Asp Gly Leu Pro Tyr Leu Gln Val Leu Lys Ala Ala Gly Val Asn
305                 310                 315                 320

Thr Thr Asp Lys Glu Ile Glu Val Leu Tyr Ile Arg Asn Val Thr Phe
                325                 330                 335

Glu Asp Ala Gly Glu Tyr Thr Cys Leu Ala Gly Asn Ser Ile Gly Ile
            340                 345                 350

Ser Phe His Thr Ala Trp Leu Thr Val Leu Pro Ala Pro Glu Lys Glu
        355                 360                 365

Lys Glu Phe Pro Thr Ser Pro Asp Tyr Leu Glu Ile Ala Ile Tyr Cys
        370                 375                 380

Ile Gly Val Phe Leu Ile Ala Cys Met Val Leu Thr Val Ile Leu Cys
385                 390                 395                 400

Arg Met Lys Asn Thr Thr Lys Lys Pro Asp Phe Ser Ser Gln Pro Ala
                405                 410                 415

Val His Lys Leu Thr Lys Arg Ile Pro Leu Arg Arg Gln Val Thr Val
            420                 425                 430

Ser Ala Asp Ser Ser Ser Ser Met Asn Ser Asn Thr Pro Leu Val Arg
        435                 440                 445

Ile Thr Thr Arg Leu Ser Ser Thr Ala Asp Ala Pro Met Leu Ala Gly
        450                 455                 460

Val Ser Glu Tyr Glu Leu Pro Glu Asp Pro Lys Trp Glu Phe Pro Arg
465                 470                 475                 480

Asp Lys Leu Thr Leu Gly Lys Pro Leu Gly Glu Gly Cys Phe Gly Gln
                485                 490                 495

Val Val Met Ala Glu Ala Val Gly Ile Asp Lys Asp Arg Pro Lys Glu
            500                 505                 510

Ala Val Thr Val Ala Val Lys Met Leu Lys Asp Asp Ala Thr Glu Lys
        515                 520                 525

Asp Leu Ser Asp Leu Val Ser Glu Met Glu Met Met Lys Met Ile Gly
```

```
            530                 535                 540
Lys His Lys Asn Ile Ile Asn Leu Leu Gly Ala Cys Thr Gln Asp Gly
545                 550                 555                 560

Pro Leu Tyr Val Ile Val Glu Tyr Ala Ser Lys Gly Asn Leu Arg Glu
                565                 570                 575

Tyr Leu Arg Ala Arg Arg Pro Pro Gly Met Glu Tyr Ser Phe Asp Ile
            580                 585                 590

Asn Arg Val Pro Glu Glu Gln Met Thr Phe Lys Asp Leu Val Ser Cys
        595                 600                 605

Thr Tyr Gln Leu Ala Arg Gly Met Glu Tyr Leu Ala Ser Gln Lys Cys
610                 615                 620

Ile His Arg Asp Leu Ala Ala Arg Asn Val Leu Val Thr Glu Asn Asn
625                 630                 635                 640

Val Met Lys Ile Ala Asp Phe Gly Leu Ala Arg Asp Ile Asn Asn Ile
                645                 650                 655

Asp Tyr Tyr Lys Lys Thr Thr Asn Gly Arg Leu Pro Val Lys Trp Met
            660                 665                 670

Ala Pro Glu Ala Leu Phe Asp Arg Val Tyr Thr His Gln Ser Asp Val
        675                 680                 685

Trp Ser Phe Gly Val Leu Met Trp Glu Ile Phe Thr Leu Gly Gly Ser
690                 695                 700

Pro Tyr Pro Gly Ile Pro Val Glu Glu Leu Phe Lys Leu Leu Lys Glu
705                 710                 715                 720

Gly His Arg Met Asp Lys Pro Ala Asn Cys Thr Asn Glu Leu Tyr Met
                725                 730                 735

Met Met Arg Asp Cys Trp Gln Ala Val Pro Ser Gln Arg Pro Thr Phe
            740                 745                 750

Lys Gln Leu Val Glu Asp Leu Asp Arg Ile Leu Thr Leu Thr Thr Asn
        755                 760                 765

Glu Glu Tyr Leu Asp Leu Ser Gly Pro Leu Gln Tyr Ser Pro Ser
770                 775                 780

Tyr Pro Asp Thr Arg Ser Ser Cys Ser Ser Gly Asp Asp Ser Val Phe
785                 790                 795                 800

Ser Pro Asp Pro Met Pro Tyr Glu Pro Cys Leu Pro Lys Tyr Gln His
                805                 810                 815

Met Asn Gly Ser Val Lys Thr
            820

<210> SEQ ID NO 55
<211> LENGTH: 2716
<212> TYPE: DNA
<213> ORGANISM: Gallus gallus

<400> SEQUENCE: 55
cgcgcggaac cctccggctg cagccgctgc cgttcccggt gaggagggat tgccctggcc      60
gaaggcactg cgttctgtcc atgctcctgt agaggtgctc agatgggatt aaagtccaca     120
tggagatatg gaaatggacc aggaacttac tctaaaaaga tggtcagctg ggattcgggt     180
tgccttatct gcctggtggt ggtcaccatg gctggacttt ccctggctcg accgtcattt     240
aacttagttg ttgaagatgc cactttggaa cccgaagagc cgccaaccaa ataccaaatc     300
tctcagccag atgtacactc tgcacttcca ggagaaccac ttgagttgcg ctgtcaattg     360
aaagacgccg tcatgatcag ttggactaag gatgggtcc ccttggggcc cgacaatagg     420
acagtgatta ttgggagta cttacaaatt aaagatgctt cacccagaga ttcgggcctc     480
```

```
tatgcttgca ctgctattag gaccctagac agtgatactc tgtacttcat tgtaaatgtt    540
acagatgctc tttcttctgg ggatgatgaa gatgacaatg atgggtctga ggactttgtg    600
aatgacagca accagatgag ggcgccctat tggacacaca cagacaaaat ggagaaaagg    660
ttacacgcag tgccagcagc aaacactgtc aagtttcgtt gcccagccat gggaaaccca    720
acaccaacca tgagatggct gaaaaatggg aaagagttta acaagaaca tcgtattggc     780
ggctataagg tccgcaacca gcactggagt ctcatcatgg agagcgtagt cccatccgac    840
aaaggaaatt acacgtgcat cgtggaaaac cagtatggct ccatcaacca cacttaccat    900
ctcgatgttg tcgagcgatc accgcacagg cccatcctcc aggctggcct tccagcaaac    960
gcctcggctg tagtcggagg tgatgtcgag tttgtctgca aagtctacag tgatgctcaa   1020
ccccacattc agtggataaa acacgtagag aggaatggga gtaaatacgg accagatgga   1080
ctgccttacc ttcaggtttt aaaggctgcc ggtgttaaca ctacggacaa agaaattgag   1140
gttctctata tacggaatgt aacttttgag gatgctgggg agtatacatg cttggcgggt   1200
aattctattg ggatatcctt tcacactgca tggttgacag ttctgccagc tcctgaaaag   1260
gaaaaggaat ttcccacatc tccagactac ctggaaatag caatttactg catagggtc    1320
ttcctgatcg cctgcatggt gctgacagtc atcctgtgcc gcatgaagaa caccaccaag   1380
aagcctgact tcagcagcca gccgctgtc cacaagctga caaagcgaat ccctctgcgc    1440
agacaggtaa cagtgtcagc tgactcaagc tcctccatga actccaacac gcctctggtg   1500
aggataacta cacgcctctc ctccactgct gatgccccaa tgctggcagg ggtctcggaa   1560
tatgaactgc cagaggatcc aaaatgggag tttccaaggg ataagctgac gctgggtaaa   1620
ccctgggggg aaggctgctt tgggcaagtg gtgatggctg aagcggtggg gattgacaaa   1680
gaccggccca agaagcagt gactgtggca gtgaagatgc tgaaagatga tgctacggaa    1740
aaggatctat ccgacctggt gtcagagatg gagatgatga agatgattgg gaaacataaa   1800
aatatcatca atcttcttgg agcctgtacc caggatggtc cgctgtatgt gattgtagaa   1860
tatgcttcca aggaaaacct gcgtgagtac ctgcgagcac gccgccctcc tgggatggaa   1920
tactccttg atattaacag ggtcccagag gagcagatga cattcaagga cttggtatcc    1980
tgcacgtacc agttggcaag aggcatggag tacttggctt cacaaaaatg tatccaccga   2040
gacctagctg caagaaatgt tttggtaact gaaaataacg tcatgaaaat agcagacttc   2100
ggtttagcca gagacatcaa caatatagat tattataaaa agactactaa tggacggctt   2160
ccagtaaagt ggatggctcc agaagctctg tttgacagag tttacacaca ccaaagcgac   2220
gtatggtcat ttggtgtgct aatgtgggag atcttcacct taggaggatc gccctaccca   2280
ggaatcccag tggaggaact ttttaagctg cttaaagaag gcaccgaat ggataaacct    2340
gccaactgca ccaatgaact ctacatgatg atgagagatt gctggcaggc tgtgccttca   2400
caaagaccaa cttttaaaca gttggtagaa gacttggatc ggatccttac tctcacaact   2460
aacgaggagt atctggacct cagcggacct ctggagcagt attcacctag ctaccctgac   2520
accaggagtt cgtgttcttc aggtgatgac tctgtttttt ctcctgatcc aatgccttat   2580
gaaccctgtc ttcccaagta ccaacacatg aatgggagcg ttaaaacatg aaaagaagca   2640
agaacatcaa gctacctacc acatacagaa catctttttct ccgggaccct aaagattctg   2700
cttgtacata tgaaat                                                   2716
```

<210> SEQ ID NO 56

<211> LENGTH: 827
<212> TYPE: PRT
<213> ORGANISM: Gallus gallus

<400> SEQUENCE: 56

```
Met Ser Glu Ala Gly Gly Ala Ala Ala Ala Ser Leu Pro Arg
1               5                   10                  15

Ser Arg Ala Gly Gly Met Arg Ala Ala Trp Gly Ser Val Trp Cys Leu
            20                  25                  30

Cys Leu Ala Ala Ala Val Gly Ala Leu Pro Ala Ala Arg Arg Gly
        35                  40                  45

Ala Glu Arg Ser Gly Gly Gln Ala Ala Glu Tyr Leu Arg Ser Glu Thr
    50                  55                  60

Ala Phe Leu Glu Glu Leu Val Phe Gly Ser Gly Asp Thr Ile Glu Leu
65              70                  75                  80

Ser Cys Asn Thr Gln Ser Ser Val Ser Val Phe Trp Phe Lys Asp
                85                  90                  95

Gly Ile Gly Ile Ala Pro Ser Asn Arg Thr His Ile Gly Gln Lys Leu
            100                 105                 110

Leu Lys Ile Ile Asn Val Ser Tyr Asp Asp Ser Gly Leu Tyr Ser Cys
        115                 120                 125

Lys Pro Arg His Ser Asn Glu Val Leu Gly Asn Phe Thr Val Arg Val
    130                 135                 140

Thr Asp Ser Pro Ser Ser Gly Asp Asp Glu Asp Asp Asp Glu Ser
145                 150                 155                 160

Glu Asp Thr Gly Val Pro Phe Trp Thr Arg Pro Asp Lys Met Glu Lys
                165                 170                 175

Lys Leu Leu Ala Val Pro Ala Ala Asn Thr Val Arg Phe Arg Cys Pro
            180                 185                 190

Ala Gly Gly Asn Pro Thr Pro Thr Ile Tyr Trp Leu Lys Asn Gly Lys
        195                 200                 205

Glu Phe Lys Gly Glu His Arg Ile Gly Gly Ile Lys Leu Arg His Gln
    210                 215                 220

Gln Trp Ser Leu Val Met Glu Ser Val Val Pro Ser Asp Arg Gly Asn
225                 230                 235                 240

Tyr Thr Cys Val Val Glu Asn Lys Tyr Gly Asn Ile Arg His Thr Tyr
                245                 250                 255

Gln Leu Asp Val Leu Glu Arg Ser Pro His Arg Pro Ile Leu Gln Ala
            260                 265                 270

Gly Leu Pro Ala Asn Gln Thr Val Val Gly Ser Asn Val Glu Phe
        275                 280                 285

His Cys Lys Val Tyr Ser Asp Ala Gln Pro His Ile Gln Trp Leu Lys
    290                 295                 300

His Val Glu Val Asn Gly Ser Lys Tyr Gly Pro Asp Gly Thr Pro Tyr
305                 310                 315                 320

Val Thr Val Leu Lys Thr Ala Gly Val Asn Thr Thr Asp Lys Glu Leu
                325                 330                 335

Glu Ile Leu Tyr Leu Arg Asn Val Thr Phe Glu Asp Ala Gly Glu Tyr
            340                 345                 350

Thr Cys Leu Ala Gly Asn Ser Ile Gly Phe Ser His His Ser Ala Trp
        355                 360                 365

Leu Thr Val Leu Pro Ala Glu Glu Leu Met Glu Met Asp Asp Ser Gly
    370                 375                 380

Ser Val Tyr Ala Gly Ile Leu Ser Tyr Gly Thr Gly Leu Val Leu Phe
```

```
            385                 390                 395                 400
        Ile Leu Val Leu Val Ile Val Ile Cys Arg Met Lys Met Pro Asn
                        405                 410                 415
        Lys Lys Ala Met Asn Thr Thr Val Gln Lys Val Ser Lys Phe Pro
                        420                 425                 430
        Leu Lys Arg Gln Gln Val Ser Leu Glu Ser Asn Ser Ser Met Asn Ser
                        435                 440                 445
        Asn Thr Pro Leu Val Arg Ile Thr Arg Leu Ser Ser Ser Asp Gly Pro
                    450                 455                 460
        Met Leu Ala Asn Val Ser Glu Leu Glu Leu Pro Pro Asp Pro Lys Trp
        465                 470                 475                 480
        Glu Leu Ala Arg Ser Arg Leu Thr Leu Gly Lys Pro Leu Gly Glu Gly
                            485                 490                 495
        Cys Phe Gly Gln Val Val Met Ala Glu Ala Ile Gly Ile Asp Lys Asp
                        500                 505                 510
        Lys Pro Asn Lys Ala Ile Thr Val Ala Val Lys Met Leu Lys Asp Asp
                    515                 520                 525
        Ala Thr Asp Lys Asp Leu Ser Asp Leu Val Ser Glu Met Glu Met Met
                    530                 535                 540
        Lys Met Ile Gly Lys His Lys Asn Ile Ile Asn Leu Leu Gly Ala Cys
        545                 550                 555                 560
        Thr Gln Asp Gly Pro Leu Tyr Val Leu Val Glu Tyr Ala Ser Lys Gly
                            565                 570                 575
        Asn Leu Arg Glu Tyr Leu Arg Ala Arg Arg Pro Pro Gly Met Asp Tyr
                        580                 585                 590
        Ser Phe Asp Thr Cys Lys Leu Pro Glu Glu Gln Leu Thr Phe Lys Asp
                    595                 600                 605
        Leu Val Ser Cys Ala Tyr Gln Val Ala Arg Gly Met Glu Tyr Leu Ala
                        610                 615                 620
        Ser Gln Lys Cys Ile His Arg Asp Leu Ala Ala Arg Asn Val Leu Val
        625                 630                 635                 640
        Thr Glu Asp Asn Val Met Lys Ile Ala Asp Phe Gly Leu Ala Arg Asp
                            645                 650                 655
        Val His Asn Ile Asp Tyr Tyr Lys Lys Thr Thr Asn Gly Arg Leu Pro
                        660                 665                 670
        Val Lys Trp Met Ala Pro Glu Ala Leu Phe Asp Arg Val Tyr Thr His
                    675                 680                 685
        Gln Ser Asp Val Trp Ser Phe Gly Val Leu Leu Trp Glu Ile Phe Thr
                    690                 695                 700
        Leu Gly Gly Ser Pro Tyr Pro Gly Ile Pro Val Glu Glu Leu Phe Lys
        705                 710                 715                 720
        Leu Leu Lys Glu Gly His Arg Met Asp Lys Pro Ala Asn Cys Thr His
                            725                 730                 735
        Asp Leu Tyr Met Ile Met Arg Glu Cys Trp His Ala Val Pro Ser Gln
                        740                 745                 750
        Arg Pro Thr Phe Lys Gln Leu Val Glu Asp Leu Asp Arg Val Leu Thr
                    755                 760                 765
        Met Thr Ser Thr Asp Glu Tyr Leu Asp Leu Ser Val Pro Phe Glu Gln
                    770                 775                 780
        Tyr Ser Pro Ala Gly Gln Asp Thr His Ser Thr Cys Ser Ser Gly Asp
        785                 790                 795                 800
        Asp Ser Val Phe Ala His Asp Leu Leu Pro Asp Glu Pro Cys Leu Pro
                            805                 810                 815
```

Lys His Val Pro Cys Asn Gly Val Ile Arg Thr
            820                 825

<210> SEQ ID NO 57
<211> LENGTH: 5395
<212> TYPE: DNA
<213> ORGANISM: Gallus gallus

<400> SEQUENCE: 57

| | | | | | |
|---|---|---|---|---|---|
| cgcagcagcg | gagcggagcg | ctgagcggcg | gcagcatgcg | gccggggat | gtctgaggcg | 60 |
| ggcggcggtg | cggcggcggc | ggcctcgctg | ccccggagcc | gcgccggagg | gatgcgggcg | 120 |
| gcctggggct | ccgtctggtg | cctgtgcctg | gcggcggccg | tcggagcgct | gccggcggcg | 180 |
| cgccggcgcg | gagcggagcg | gagcggcggg | caggcggcag | aatacttgag | gagcgagacc | 240 |
| gcctttctgg | aagagttggt | gtttggaagt | ggagatacca | ttgaactttc | ctgtaacacc | 300 |
| cagagctctt | ctgtgtcagt | tttctggttt | aaagatggta | ttgggattgc | accttccaac | 360 |
| agaactcata | ttggacaaaa | actgttgaag | ataatcaatg | tgtcatatga | cgattcgggg | 420 |
| ctgtacagtt | gcaagccaag | gcattccaac | gaggtcctgg | aaactttac | agtcagagtg | 480 |
| acagattccc | cttcgtcagg | tgatgatgaa | atgatgacga | tgagtcaga | ggatacaggt | 540 |
| gtccccttct | ggacccggcc | agataagatg | gagaagaagc | tgctggcagt | cctgccgcc | 600 |
| aacaccgttc | gcttccgatg | tccagcaggt | ggaaacccaa | ctcccaccat | ttactggctg | 660 |
| aagaatggca | agaattcaa | gggagagcac | aggatcgggg | gcatcaagtt | gcgacaccag | 720 |
| cagtggagct | tggtgatgga | gagcgttgtg | ccgtcagatc | gaggaaacta | cacctgtgtt | 780 |
| gtggagaaca | aatatggcaa | tattaggcac | acataccagc | ttgatgtttt | agaacggtca | 840 |
| ccccaccgac | caatcctgca | agcaggactc | cctgccaatc | agactgtggt | ggtcgggagc | 900 |
| aatgtggaat | tcactgcaa | ggtctacagc | gatgcccagc | ctcatatcca | gtggctgaaa | 960 |
| cacgtagaag | tcaacggcag | caagtatgga | cctgatggga | caccctatgt | cacagtgctg | 1020 |
| aagacggcag | gtgttaacac | aacggataag | gagctagaga | ttctgtactt | gcgaaatgtt | 1080 |
| actttgaag | atgctgggga | atatacttgt | ctcgcaggga | attctattgg | gttctcacat | 1140 |
| cactctgctt | ggctgacggt | gctaccagca | gaggagctga | tggaaatgga | tgattcgggc | 1200 |
| tcagtgtacg | ctggcattct | cagctatggc | actggcttag | tcctcttcat | cctggtgctg | 1260 |
| gtcattgtga | ttatctgcag | gatgaaaatg | ccaaacaaaa | aggccatgaa | caccaccact | 1320 |
| gtacagaaag | tctccaaatt | tccactcaag | agacagcagg | tgtcgttgga | gtccaactct | 1380 |
| tccatgaatt | ccaacacacc | cctggtccgg | atcactcgtc | tctcctccag | cgatgggccg | 1440 |
| atgctggcca | acgtctctga | gctggaactt | cctccagatc | ccaagtggga | attggcacgt | 1500 |
| tctcgcctga | ccctggggaa | gccgcttggt | gagggctgtt | ttggccaagt | ggtgatggcg | 1560 |
| gaagcaattg | ggattgataa | agacaagcca | aacaaggcca | tcaccgtggc | tgtcaagatg | 1620 |
| ttaaaagatg | atgccacaga | caaggacctt | tcagacctgg | tctctgagat | ggaaatgatg | 1680 |
| aaaatgattg | ggaagcacaa | aaacatcatt | aacctgctcg | gtgcttgcac | gcaggacgga | 1740 |
| ccgctctacg | tgttggttga | atatgcatcg | aaggggaact | tgcgggaata | cctcagggca | 1800 |
| cgtcgcccac | ctggcatgga | ctattccttc | gacacctgca | agctgcccga | ggagcagttg | 1860 |
| acatttaaag | acctggtttc | ctgcgcctac | caggtggccc | ggggcatgga | gtacttggcg | 1920 |
| tcacagaaat | gcattcatcg | tgacttggca | gccaggaatg | tgttagtcac | tgaggacaat | 1980 |
| gtgatgaaaa | tagctgattt | tggccttgct | agagacgttc | acaacatcga | ctattacaag | 2040 |

```
aaaaccacca atggtcggct gcctgtgaaa tggatggctc cagaagcatt gtttgaccgg   2100
gtctatactc accagagcga tgtctggtct tttggagtgc tactatggga gatcttcact   2160
ttgggagggt ctccgtaccc gggaattcct gttgaagaac tcttcaaact cttgaaagaa   2220
ggccatcgga tggataaacc cgccaactgt acccacgacc tgtacatgat catgcgggag   2280
tgctggcacg ctgtcccctc gcagcgaccc acattcaagc agctggtgga agacctggac   2340
agagtcctca ccatgacatc cactgatgag tacctgacc tctcggtgcc ctttgagcaa    2400
tactcacccg ctggccagga cacccacagc acctgctcct caggggacga ctcggttttt   2460
gcacatgacc tgctgcctga tgagccctgc ctgcccaagc acgtgccctg taatggcgtc   2520
atccgcacgt gacggccccc caggacagac ggatggacag acaggcagtg ttcccaccct   2580
ggcgcaagcg cagagcgccg aagacaaacc catagtgaag gatgtttcca tgaaactgct   2640
cggtgatgcc ggaggatttt tgttgtcaag ttttttttg ttttgtttgg ttggtttttt     2700
tcccatttgc tgtataaaaa gtcaagaagc actgttggc ctgaaggaac tcatctcttg     2760
ccaagatgat ctatcgtgta tgatttttt tattattatt attattatta ttttctttt     2820
ttcctaagca gaatgttaaa cctgagggta ctgccctccc gcctgcgctt gccgagcgcc   2880
tgagtagcca atctgtgcct actatatgaa aaagaggaaa aaatcttcc tagaagaaga    2940
aaagctaatg aaaaaaaaa tgtaaagaat gtagaaattc tttgcttatg caatctgtac     3000
atgaaccttt ttggtggagc tgaaaagcca cgttgcctgc agggattcat atatttatag   3060
aaatatctat attttttgttg tcgtcgttt tatagcttcg tgaccttatt tcccagctac   3120
atagaaggaa tcttgtccag aagaagaaga aaataaata aatgatacgc aaatcaacat    3180
ggaggaagaa ttaaaaataa ttaaaataaa aaaaaagac agtcaagtca tcctatagga   3240
ggagagcacc gcctggccgc tggccatgtc ctgtagggat tgcacaccca tgtggcatct   3300
tgagctgtgt cccagcctgc aggaagagcc aatgtgggga aaatcttgct ttttggagac   3360
gggggtttgc atacttttgc ttacaaaggg caagttgtag gggagaagct cctccagccc   3420
ttggcaccag cggtttggct ccatctacat gcagtgactt ggagaaagaa gttacgggta   3480
cctgtaggca agagccttta acttatatca aaaaggttta ttccagagaa tctgtgtata   3540
tatctataaa tatatcctgt atatatataa ataaatatat ggggaaaaaa aaaagaatg    3600
tataatacta attcaacgta aagcagtact gagagagagt ctcaaaatac gagcattgca   3660
atctaggata tactgatctg gatgaaagag aagagttgtg tttgttttat atcttcacag   3720
ttttgtttta aaaattgtac gttaacatgt atatttgtaa agttatttat agacattaac   3780
agatctgttc ttcggtttaa atagcgtagc gttactgtaa actttaaatt tcaccgagtt   3840
taagggtggt ttttttttta acttattaaa aatggagaaa aagtatatta atcaagtttt   3900
tcttttgtgt ttatgggaaa tattgaaaga atgtatagat gtacagtcct ttaacaaatt   3960
acatttaatg ttttatatat atatatatat atatatgtat tcgttaaaaa aaatattagt   4020
ttatcctgga ttgcagtgag caaaggtaag tttattttc aatacatcac cagtggttaa    4080
aaccaaacca atagcagaga gatggttttt acgtatttca gaaaaaaaga gggccaagat   4140
ttcttccatc actttaacca ctgtgcatta cgggggcgtg ggtgtttatt tttctatttt   4200
ggaatgaagg tattctttgt ggtcgagtca ataagaagca cgcagcaaag caacgtgttg   4260
actttggatg acgcgcatta attttttttc cccctgtgcc agtaatgttg tattttgggt   4320
ttaagaaata ccatacgggc aaaatagaga gaggagcgac attgtttgca ggggagatgc   4380
```

```
aacgactgca tatttctttt gcatttaaca cattgaaaaa tgccagtgat gcctagtttt    4440
ctgtgttcga aatgctgtgc ttttttttgtt cctgaatgtc agacagcaca tgagtgaaaa    4500
aagaaccttc acgtggctca ggctgacgag ggggggagg tttggggtgg gctttttttg     4560
ttgttgtttg ttccttttttt tttccttttttt tttttttttttt tttttttttg tccagaagac    4620
tgtatctact accacaaaga ggcaaggaga attgcatcct gaattcctcc tttatgtttt    4680
gctctggtgc atattacata tcaaggtttc agaatagcag gatggcagca tctcattttt    4740
aaggtggttt gttgttttttt ttttggtttt tttttttcct tcttagagcc acaaaatcct    4800
taccctaaaa taataattt atagtttgag gttatttcaa tggaagtttg agaaggtaga    4860
tttctataga attttgtttt gttgggatta aaaaaaaaag aaaaaaaaga attttttggt    4920
attttcttac aaatgtctgc taattgtgta cattccaagt actcgaagcg ttgcgtttcg    4980
tgtactgaaa aagaaaatg tacaaaactg tgcatgattt caaatgttac tagatattat     5040
aaatatatat ataatttatt gagtttttac aagatgtatc tgttgtagac ttgttgactt    5100
aacatttctt attcaatgct tatatagttt tatagcctgg actgttatct ttaagagctt    5160
aaaaaaatta aaattccaat tttgttacat tttatactgt tgatgttaca atccacaggt    5220
ttgcgtagcg tgatttttca acgagcaact ctgttcagtt tattttaata atgtacttct    5280
gtgcctgaca gctgcagctg tccaaggtgt gagacaaaca ctaaataaaa ctattctgct    5340
tttgttaaaa aaaaaaaaaa aaaaaaaaaa aaaaaaaaaa aaaaaaaaaa aaaaa        5395
```

FGF MODULATION OF IN VIVO ANTIBODY PRODUCTION AND HUMORAL IMMUNITY

CROSS-REFERENCE TO RELATED APPLICATIONS

This application is a continuation-in-part of U.S. patent application Ser. No. 12/941,070 filed Nov. 7, 2010 (now U.S. Pat. No. 8,435,525) which claims the benefit of U.S. provisional patent application Ser. No. 61/324,947 filed Apr. 16, 2010, each of which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on May 3, 2013, is named AB001D1Sq.txt and is 275,405 bytes in size.

FIELD OF THE INVENTION

The invention relates to the field of humoral immunity.

BACKGROUND OF INVENTION

Organisms control antibody production at multiple steps during an immune response and this response must be carefully adjusted to the invading pathogen. If the response is excessive, autoimmune defects can damage host tissues, whereas if it is inadequate, the pathogen may persist and threaten survival. Soluble factors have been identified that stimulate the humoral immune response, but our knowledge of negative regulators of this process has been quite limited (Ravetch et al., 2000, Science 290:84). Indeed, few soluble cytokines have been identified whose loss of function leads to enhanced antibody production.

During the humoral immune response, a complex set of signaling events orchestrate antibody production. The process begins with antigen presentation to mature peripheral B cells, which proliferate and migrate to germinal centers. Cells possessing B cell receptors with the highest affinity for antigen are favored to survive while their low-affinity counterparts more readily undergo apoptosis. The activated B cells which survive this selection differentiate into memory B cells or antibody-secreting plasma cells. Many B cells also secrete antibody outside of the germinal center selection process in the extrafollicular response (MacLennan et al., 2003, Immunol Rev 194:8). Extrafollicular responses are thought to be important following exposure to T-independent antigens (Fagarasan et al., 2000, Science 290:89; Martin et al., 2001, Immunity 14:617). Once the antigen has been removed, B cells return to a resting state. Turning off B cell activation is necessary both for homeostatic resetting of antibody secretion and also for preventing pathologic autoimmune conditions. Little is known about the soluble factors which control the deactivation process.

The fibroblast growth factor (FGF) family of extracellular regulators has been shown to control the physiology and development of virtually all higher vertebrate tissues. Twenty-three FGF ligands have been identified in mammals, and these ligands interact with cell surface receptors encoded by five different genes (Wiedemann et al., 2000, Genomics 69:275; Ornitz et al., 2001, Genome Biol 2). Alternative splicing in the ligand-binding domain generates variable forms of the FGF receptors, thereby increasing diversity.

FGF2, or basic FGF, was the first identified FGF family member (Abraham et al., 1986, Embo J 5:2523) and is one of the most extensively studied. Expressed in most embryonic and adult tissues, it exists in high and low molecular weight isoforms due to initiation of translation at alternative start sites. It binds to all five receptors with preference for the "c" alternate splice form of receptors 1-3 (Ornitz et al, 1996, J Biol Chem 271:15292). FGF2 has been shown to stimulate widely varying effects, including proliferation, differentiation, apoptosis, and migration. Consequently, the FGF2 signal is interpreted differently depending on cellular context.

U.S. Pat. No. 4,994,559 discloses human basic fibroblast growth factor.

U.S. Pat. No. 5,229,501 discloses expression and use of human fibroblast growth factor receptor.

U.S. Pat. No. 5,228,855 discloses an extracellular form of human fibroblast growth factor receptor.

U.S. Pat. No. 5,707,632 discloses receptors for fibroblast growth factors.

U.S. Pat. No. 5,891,655 discloses methods for identifying molecules that regulate FGF activity and oligosacharide modulators of FGF receptor activation.

U.S. Pat. No. 6,071,885 discloses treatment of FGF-mediated conditions by administration of cardiac glycoside and aglycone derivatives thereof.

U.S. Pat. No. 6,350,593 discloses receptors for fibroblast growth factors and methods for evaluating compositions for antagonism to fibroblast growth factors and fibroblast growth factors receptors.

U.S. Pat. No. 6,255,454 discloses expression and use of a human fibroblast growth receptor and a soluble version of the receptor.

U.S. Pat. No. 6,900,053 discloses antisense modulation of fibroblast growth factor receptor 2 expression.

Multiple human therapeutics are designed to enhance the immune response, but their use in humans are complicated by severe side effects. For example, exogenous IL-2 is administered to patients with advanced melanoma in order to stimulate the anti-tumor immune response. But this biologic, acting as a systemic cytokine which directly activates T cells, is beset by harsh side effects, such as dangerous hypotension. What is needed are new methods for enhancing immune function and, in particular, humoral immunity.

SUMMARY OF INVENTION

A new role for fibroblast growth factor (FGF) signaling in the negative regulation of the humoral immune response has been discovered by the present inventor. It has been found that antibody production to a Type I Independent antigen is enhanced in the absence of FGF2 and conversely, is suppressed when FGF2 is over-expressed. Therefore, FGF2 is an inhibitor of the humoral immune response. In addition, it has been discovered that splenic germinal centers require FGF2 for efficient formation.

One embodiment of the invention provides a method for increasing humoral immune response to vaccination with an immunogen, for example, an antigen or a live or killed vaccine, in a mammal or other higher vertebrate, that includes: in conjunction with the vaccination of a mammal to the immunogen other than FGF2, inhibiting the activity of a fibroblast growth factor, such as FGF2, in the mammal, thereby increasing the humoral immune response to the antigen. In one variation, the immunogen is other than a fibroblast growth factor and other than a fibroblast growth factor receptor.

Another embodiment of the invention provides a method for treating an immune deficiency in a mammal, such as a human, that includes: increasing the production of endogenous antibodies in the mammal by inhibiting the activity of a fibroblast growth factor, such as FGF2, in the mammal.

A further embodiment of the invention provides a method for treating a microbial infection in a mammal, such as a human, that includes: inhibiting the activity of a fibroblast growth factor, such as FGF2 in a mammal in need of treatment for a microbial infection, to an extent effective to increase antibody production in the mammal. The inhibiting step may include or consist of administering a fibroblast growth factor antagonist, such as a FGF2 antagonist, to the mammal in an amount effective to increase antibody production in the mammal. The method may further include the step of administering an antibiotic or anti-viral agent to the mammal which is active against the microbial infection.

Another embodiment of the invention provides a method for increasing in vivo antibody production in a mammal, such as a human, that does not have a cancer that includes the step of by inhibiting the activity of a fibroblast growth factor, such as FGF2, in the mammal. In one variation, the mammal is a geriatric human.

A still further embodiment of the invention provides a method for decreasing antibody production, such as pathological antibody production, in a mammal such as a human, in need of such reduction, by administering to the mammal, in an amount effective to decrease antibody production in the mammal, a fibroblast growth factor or agonist thereof, such as FGF2 or an FGF2 agonist, or an agonist of a receptor that binds a fibroblast growth factor such as FGF2, for example FGFR1, FGFR2 and FGFR3.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention.

DETAILED DESCRIPTION

It is now shown that the humoral immune response is altered in FGF2 mutant mice. FGF2 deficient mice produce more antibody to a Type I independent antigen while FGF2 over-expressing mice show suppressed antibody production to the same pathogenic stimulus. In addition, germinal center formation is compromised in the absence of FGF2. Surprisingly, changes in both antibody production and germinal center formation are observed in mice lacking a single copy of FGF2, demonstrating that lymphocytes are particularly sensitive to FGF2 gene dosage. These studies provide the first evidence that FGF signaling is a crucial regulator of the humoral immune response and mature B cell function.

Materials and Methods

Mice.

Figure 3:
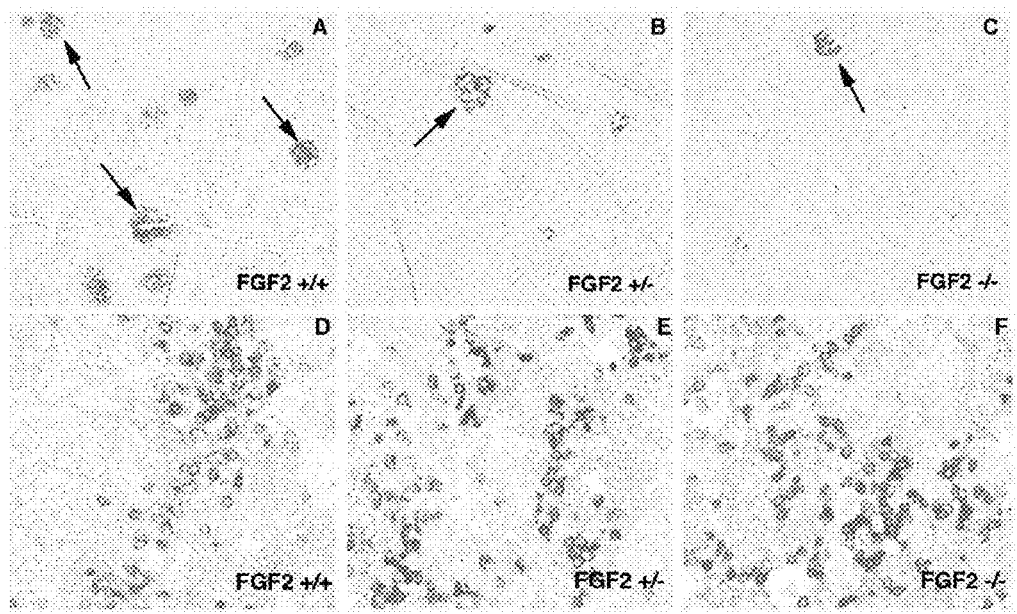
FIG. 3, panels A-F, show that FGF2 deficiency affects germinal centers but not syndecan expression.
Figure 4:
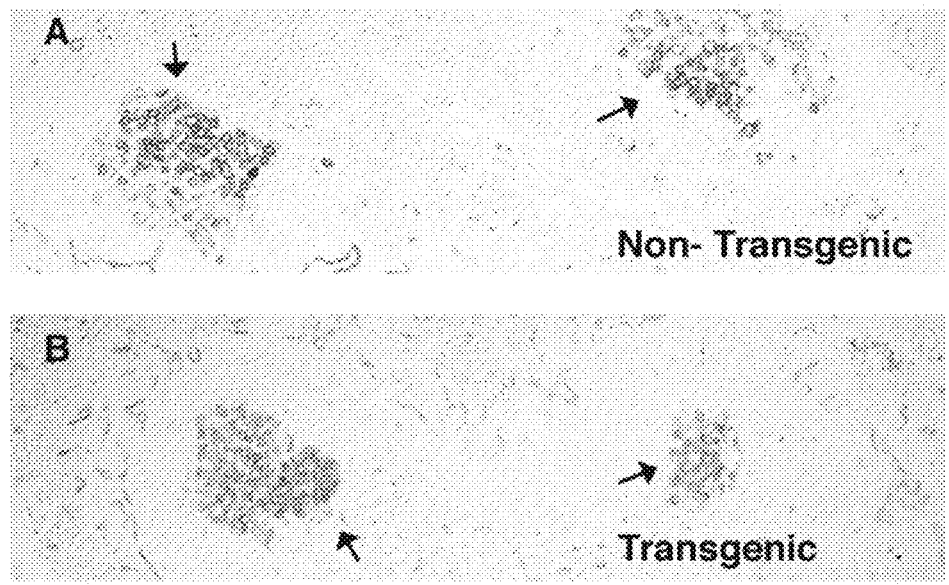
FIG. 4, panels A and B, show shows that ectopic expression of FGF2 does not suppress germinal center formation.

FGF2−/− (homozygous gene knockout) mice were obtained from two academic sources. These mice display relatively benign defects in wound healing, blood pressure regulation and cortical neurogenesis and do not express detectable levels of FGF2 protein (Ortega et al., 1998. Proc Natl Acad Sci USA 95:5672; Zhou et al., 1998, Nature Medicine 4:20). Both sets of knockouts showed increases in antibody production and data in FIGS. 1 and 3 are for animals obtained from the University of Cincinnati. Heterozygous animals (mixture of 129SvEv:Black Swiss) were mated and heterozygous and null animals were compared to littermate controls. Adult mice of both sexes were used. FGF2 transgenic animals exhibit bone dysplasia and disruption of endothelial homeostasis (Fulgham et al., 1999, Endothelium 6:185; Coffin et al., 1995, Mol Biol Cell 6:1861). Animals (FVBN) heterozygous for the transgene were mated to wild type and adult animals of both sexes were compared to littermate controls. Animals were maintained in a pathogen-free facility, following institutional standards. Protocols adhered to IACUC guidelines.

Humoral Immune Response.

Mice were immunized intraperitoneally with 50 ug TNP-LPS (tri-nitrophenol lipopolysachharide) emulsified with complete Freund's adjuvant in PBS (200 ul final volume). Serum was harvested from retro-orbital eye bleeds. After coagulation, bleeds were centrifuged and sodium azide (0.01%) was added. ELISAs for TNP specific antisera were performed on plates coated with TNP-BSA (Biosearch) and primary antisera were bound overnight at 4° C. Goat anti-mouse IgG (all Ig isotypes) coupled to Alkaline Phosphatase was used as secondary antisera (Jackson). The genotype of the serum was unknown to the experimenter. Absorbance (405 nM) was measured in triplicate on a Molecular Devices spectrophotometer. Values were averaged and measurements were taken from absorbance in the middle of the dynamic range. For quantification of difference in antibody titer, serial dilutions were performed and the average value from the serum of all animals (minimum n=5, +/−s.e.m.) was plotted. Omission of either primary or secondary anitsera reduced signal to background levels.

Immunohistochemistry

Histochemistry was performed on 5 micrometer histologic sections made from formalin fixed, paraffin-embedded spleens. Sections were blocked in PBST (PBS with 0.1% Tween-20) containing 10% normal rabbit serum, stained with the lectin peanut agglutinin, then biotinlyated anti-peanut agglutinin (Vector Laboratories, Burlingame, Calif.), or rat anti-CD138 (syndecan-1) (Becton Dickinson) followed by biotinylated goat anti-rat IgG secondary antibody (Jackson Immunoresearch). Primary antibody was incubated either overnight at 4° C. or for one hour at room temperature. Removal of either primary or secondary antiserum abolished specific signal.

Germinal center number was scored by experimenters blind to the source of the sections. At least three serial sections were scored for each spleen. Results are based on three independent experiments from two or more animals per genotype. Data are presented from the final experiment which used the largest number of animals.

Proliferation of B Cells In Vitro.

Adult wild type mice (C57B16) were sacrificed and spleens were rapidly removed. After dissociation into single cell suspension and red blood cell lysis with NH4Cl, splenocytes were isolated by centrifugation over a Ficoll gradient. Subsequently, B lymphocytes were purified by one of two methods, complement mediated lysis or CD43 negative selection. For complement lysis, cells were incubated with anti-Thy 1 antibody (J1J), anti-L3T4 (GK 1.5), anti-Ly2 (TIB105, ATCC) and rabbit complement (Sigma) for two hours at 37°. CD43 negative selection was carried out using anti-CD43 (Serotec) and Miltenyi microbeads according to the manufacturer's instructions. Cells were cultured in RPMI 1640, 10% fetal calf serum for three days in the presence of anti-CD40 (mAb 1C10, generous gift of Hsiou-Chi Liou, Weill Medical College of Cornell University) and anti-IgM Fab'2 fragments (Jackson Immunoresearch). FGF1 (100 ng/ml) and Heparin (10 ug/ml) were added, and the number of cells was determined in triplicate compared to Heparin alone using a Coulter Counter (Coulter) or trypan blue exclusion with the same results.

Results

FGF2 Regulates the Humoral Immune Response

In the course of studies to evaluate the role of FGF signaling in multiple myeloma, we decided to investigate whether B cell function might be altered in FGF mutant mice. If FGF signaling affects mature B cell activity, one would predict that the humoral immune response would be affected by loss of function mutations in one of the FGF family members. To address this issue, we examined the humoral immune response in FGF2 deficient mice, one of the most widely expressed FGFs.

Figure 1A:
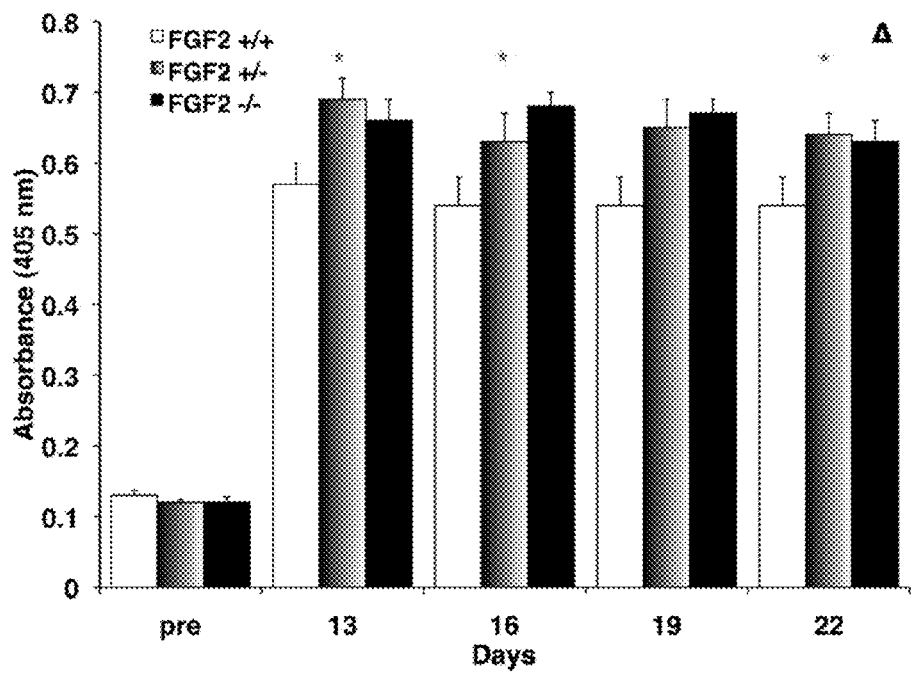
FIG. 1A shows that FGF2 deficient mice respond more strongly to a Type I Thymus Independent Antigen.
Figure 1B:
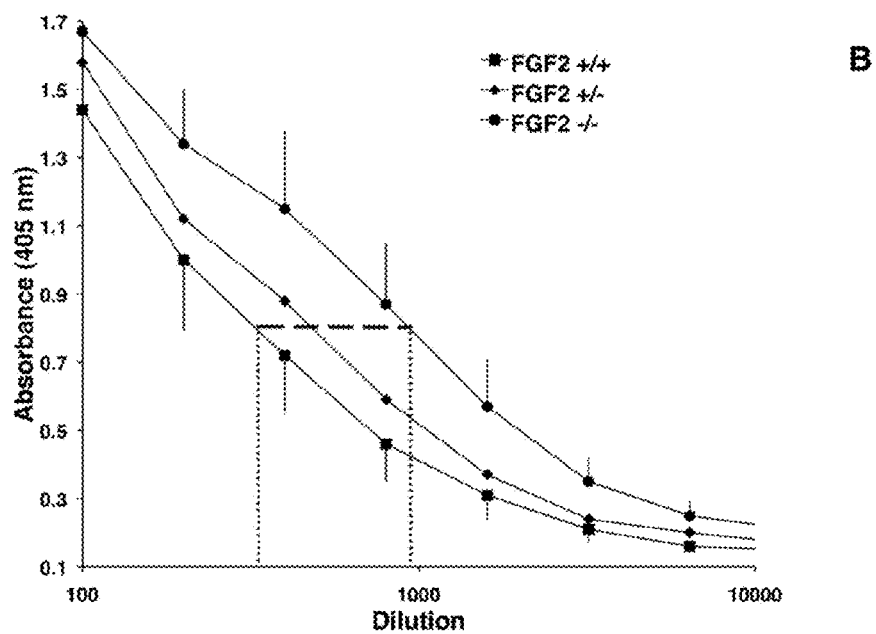
FIG. 1B shows the difference in antibody titer of FGF2 deficient animals compared to littermate controls following immunization.

Immunization with a type I independent antigen, TNP-LPS, typically stimulates polyclonal B cell activation and proliferation. This antigen can elicit antibody production in T cell depleted animals, suggesting that the response can be largely independent of T cell help. The humoral response to TNP-LPS was enhanced in the absence of FGF2 (FIG. 1A). The magnitude of the peak response and the decay to baseline are potentiated by FGF2 deficiency. Three weeks after immunization, anti-TNP antibody titers are approximately three-fold higher than littermate controls (FIG. 1B). The size of this potentiation is greater than that seen with the inhibitory FC receptor, FCγRIIB, a gene intrinsic to B cells (Takai et al., 1996, Nature 379:346). Surprisingly, mice lacking a single copy of FGF2 produce more anti-TNP antibody (FIG. 1A, day 13 and day 22 time point). These results demonstrate that FGF2 negatively regulates the primary humoral immune response and is required for the normal inactivation of antibody secretion.

FIG. 1.

FGF2 deficient mice respond more strongly to a Type I Thymus Independent Antigen. Mice were immunized with 50 ug TNP-LPS and anti-TNP specific antibodies were measured by ELISA. In FIG. 1A, data points represent average absorbance from the serum of at least five animals. Asterisks indicate statistical differences at $p<0.05$ (student's t test). FIG. 1B shows the quantification of the difference in antibody titer of FGF2 deficient animals compared to littermate controls at day nineteen after immunization. Data points represent the mean absorbance+/−s.e.m. at the indicated dilutions for each genotype. Broken line between curves with corresponding vertical line delineates difference in antibody titer at the same absorbance.

To determine whether FGF2 is sufficient to regulate antibody production, we examined the humoral immune response in FGF2 transgenic mice. These animals express a human FGF2 gene driven by the ubiquitously active promoter, phosphoglycerate kinase (Coffin et al., 1995, Mol Biol Cell 6:1861). Different forms of FGF2 protein are produced from the FGF2 gene, including several high and low molecular weight isoforms. In FGF2 transgenic animals, there is a marked increase in the expression of the 18-Kd form of FGF2 in selected tissues, including spleen (Coffin et al., 1995, Mol Biol Cell 6:1861).

FIG. 2.

FGF2 transgenic mice respond more weakly to a Type I Thymus Independent Antigen. Mice were immunized with 50 ug TNP-LPS and anti-TNP specific antibodies were measured by ELISA using TNP-BSA coated plates. Asterisks indicate statistical differences at $p<0.05$ (student's t test). FIG. 2B shows the quantification of antibody titer of FGF2 transgenic animals compared to littermate controls at day twenty one after immunization. Data points represent the mean absorbance+/−s.e.m. at the indicated dilutions. Broken line between curves with corresponding vertical line delineates difference in antibody titer at the same absorbance.

Figure 2A:
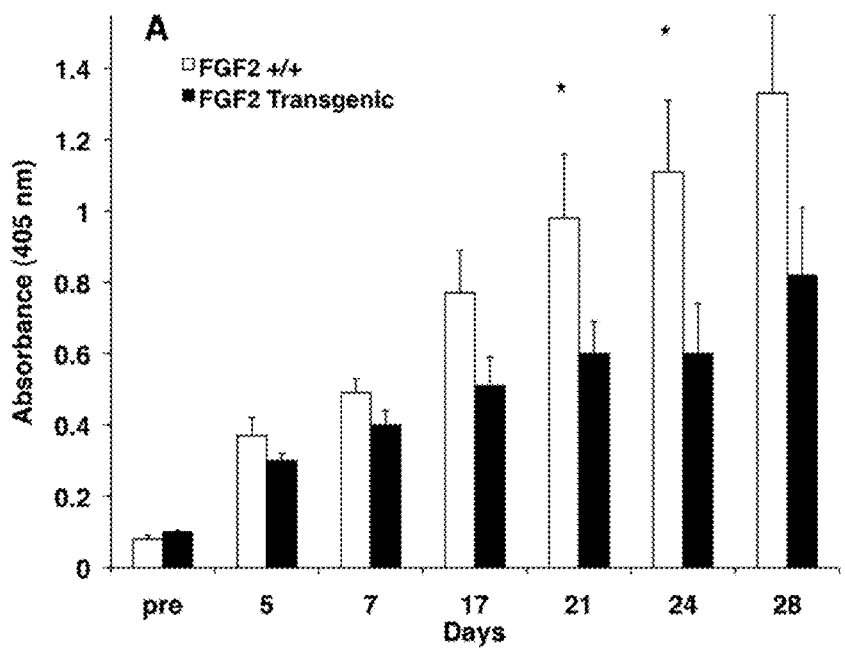
FIG. 2A shows FGF2 transgenic mice respond more weakly to a Type I Thymus Independent Antigen.
Figure 2B:
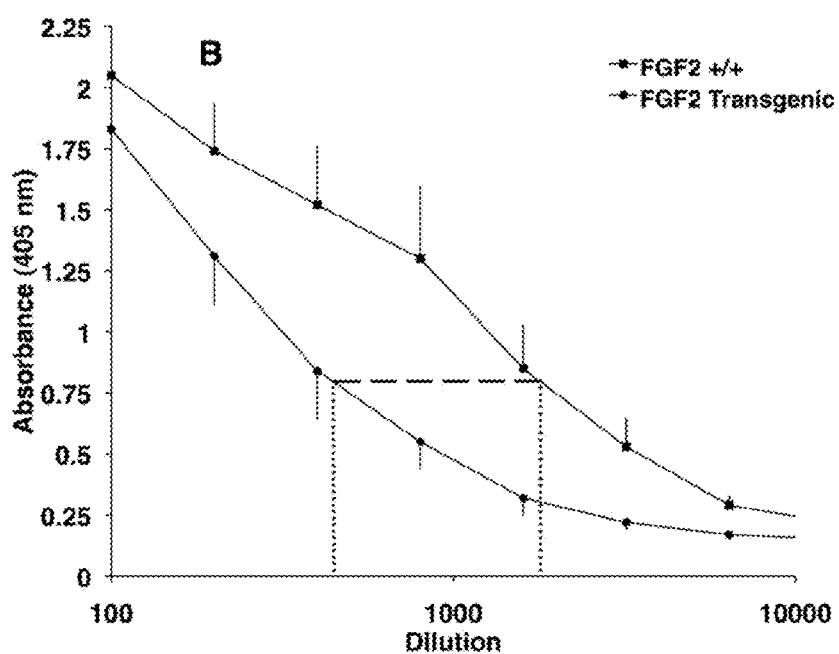
FIG. 2B shows the quantification of antibody titer of FGF2 transgenic animals compared to littermate controls following immunization.

It was found that antibody production in response to TNP-LPS is significantly diminished in FGF2 transgenic animals, as shown in FIG. 2A. Suppression of antibody production begins relatively late during the primary response, with statistically significant differences not observable until twenty one days after administration of immunogen. The reduction in antibody titers is slightly larger than the enhancement seen in the absence of FGF2 (four-fold). Therefore, FGF2 is both necessary and sufficient to control the humoral immune response. Taken together, these observations identify FGF2 as a soluble regulator of antibody production.

Once activated by antigen, B cells migrate to germinal centers, where high affinity, somatically mutated antibodies are generated. To determine whether germinal centers are affected by FGF2, we examined the number of splenic germinal centers formed in the FGF2 null mice. Lectin staining reveals that the number of germinal centers is substantially reduced approximately two weeks after immunization with TNP-LPS, with six-fold fewer germinal centers formed in null animals (FIG. 3, panels a-c; Table 2). Fewer germinal centers are also observed two days after immunization (Table 1). Unexpectedly, germinal centers are also reduced in heterozygous animals.

TABLE 1

| Mouse | +/+ | +/− | −/− |
|---|---|---|---|
| 1 | 4 | 2 | 1 |
| 2 | 3 | 0 | 0 |
| 3 | 0 | 0 | 0 |
| 4 | 8 | 0 | 0 |
| 5 | 3 | 2 | — |
| 6 | 1 | 2 | — |
| 7 | 0 | 1 | — |
| 8 | 0 | 4 | — |
| 9 | 1 | 0 | — |
| 10 | 4 | 0 | — |
| 11 | 4 | 3 | — |
| 12 | 3 | 3 | — |
| 13 | — | 4 | — |
| Mean | 2.6 | 1.6 | 0.25 |
| s.e.m. | 0.7 | 0.4 | 0.25 |
| N | 12 | 13 | 4 |

TABLE 2

| Mouse | +/+ | +/− | −/− |
|---|---|---|---|
| 1 | 5 | 3 | 11 |
| 2 | 13 | 0 | 3 |
| 3 | 11 | 0 | 3 |
| 4 | 9 | 0 | 0 |
| 5 | 14 | 0 | 0 |
| 6 | 8 | 0.5 | 0 |
| 7 | — | — | 4 |
| Mean | 10 | 0.6 | 1.7 |
| s.e.m. | 1.4 | 0.5 | 0.76 |
| N | 6 | 6 | 7 |

Tables 1 and 2.

Germinal center formation is dependent on FGF2 gene dosage. FGF2+/+, +/−, −/− mice were immunized i.p. with 50 ug TNP-LPS. Spleens were stained for expression of germinal centers with peanut agglutinin two days (Table 1) and approximately two weeks (Table 2) after immunization. Significantly fewer germinal centers were formed in FGF2 heterozygous ($p<0.01$) and null mice ($p<0.01$) sixteen days after immunization (Student's t test). Significantly fewer germinal centers were formed in FGF2 null mice ($p<0.05$) two days after immunization.

Gross morphologic features of the spleen are similar in the three genotypes. To determine whether plasma cell development is affected in FGF2 deficient animals, we examined the expression of syndecan-1, a cell surface heparin sulfate proteoglycan which is expressed on plasma cells. The number of syndecan positive plasma cells is not noticeably different, suggesting that FGF2 does not influence the adoption of the plasma cell fate in the spleen (FIG. 3, panels d-f). These results demonstrate that splenic germinal center formation is dependent on FGF2 gene dosage.

FIG. 3. FGF2 deficiency affects germinal centers but not syndecan expression. FGF2+/+, +/−, −/− mice were immunized i.p. with 50 ug TNP-LPS. A-C) Spleens were stained for expression of germinal centers with peanut agglutinin two weeks after immunization. D-F) Expression of syndecan-1 was determined by monoclonal antibody anti-CD138 (BD).

TABLE 3

| Mouse | Transgenic | Wild-type |
|---|---|---|
| 1 | 3.5 | 6 |
| 2 | 2 | 6 |
| 3 | 0 | 2 |
| 4 | 0.5 | 0 |
| 5 | 2 | 2 |
| 6 | 3 | 4 |
| 7 | 0 | 1 |
| 8 | 2 | 2 |
| 9 | 4 | 8.5 |
| 10 | 2 | — |
| Mean | 1.9 | 3.5 |
| s.e.m. | 0.4 | 0.9 |
| n | 10 | 9 |

Table 3.

Germinal center formation is not affected by ectopic expression of FGF2. FGF2 transgenic mice and littermate controls were immunized i.p. with 50 ug TNP-LPS. Spleens were stained for expression of germinal centers with peanut agglutinin fourteen days after immunization.

To determine whether germinal centers were affected by over-expression of FGF2, we performed the same experiment in FGF2 transgenic animals. We find that although there is a trend towards fewer germinal centers when FGF2 is over-expressed, the difference is not statistically significant (Table 3). These data show that over-expression of FGF2 is not sufficient to regulate germinal center formation two weeks after immunization with a Type 1 independent antigen.

FIG. 4.

Ectopic expression of FGF2 does not suppress germinal center formation. FGF2 transgenic and littermate controls were immunized i.p. with 50 ug TNP-LPS. A,B) Spleens were stained for expression of germinal centers with peanut agglutinin two weeks after immunization.

FGF2 is one of the more widely expressed members of the FGF family of ligands, with strong expression in multiple tissues. To determine whether FGF2 is expressed in the spleen we evaluated FGF2 levels by ELISA (R and D Systems). We find that FGF2 is found at 302+/−17 pg/ml (mean+/−s.d. n=4), demonstrating levels that are comparable to those found in other FGF2 responsive tissues. In addition, functional studies have demonstrated that both FGF-1 and FGF2 are present in the spleen in forms which can stimulate liver cell proliferation (Suzuki et al., 1992, Biochem Biophys Res Commun 186:1192).

To determine whether FGF can directly control B cell activation, we explored whether addition of exogenous FGF would affect B cell proliferation in vitro. B cells were purified from spleen and CD40 and BCR signaling were simultaneously activated using stimulating antibodies. Inducing these systems transmits powerful growth and survival signals, leading to rapid proliferation. To investigate whether FGF signaling might affect this response, we incubated the cells in the presence of FGF-1. We used FGF-1 instead of FGF2 because it stimulates the widest range of FGF receptors (8). Under these conditions, B cell number is inhibited by FGF stimulation (Table 3), suggesting that it can directly inhibit antigen stimulated B cells.

TABLE 4

| Experiment | % Decrease |
|---|---|
| 1 | 27 |
| 2 | 25 |
| 3 | 10 |
| 4 | 15 |
| 5 | 16 |
| 6 | 25 |
| X | 19.7 +/− 2.8 |

Table 4.

FGF signaling inhibits splenic B cell proliferation. Spleens from adult wild-type mice were dissected and highly enriched populations of B cells were purified. Cells were cultured in serum-containing medium for 3 days in the presence of a CD40 activating monoclonal antibody (1C10) and anti-mouse IgM Fab'2 fragments (Jackson). The values represent the percent decrease in total cell number observed with addition of 100 ng/ml FGF1 (determined in triplicate) as compared to heparin (10 ug/ml) alone. x=mean+/−s.e.m. One sample t test, $p<0.01$.

Discussion

Using gain and loss-of-function mouse models, it was shown that FGF2 controls the humoral immune response. These observations constitute the first indication that any member of this large family of pleiotropic signaling factors affects the humoral immune response.

Based on its widespread expression and its robust effects on a diverse array of cell types, FGF2 is postulated to control multiple biological processes. However, studies with mice lacking this gene have challenged this belief, implicating other FGF family members or suggesting that FGF signaling is not essential (Ortega et al., 1998. Proc Natl Acad Sci USA 95:5672; Zhou et al., 1998, Nature Medicine 4:201; Dono et al., 1998, Embo J 17:4213). In light of these limited phenotypes, it was not expected that mice lacking a single copy of FGF2 would show abnormalities in immune function. Thus, in contrast to other systems, lymphoid tissue appears to be especially sensitive to FGF2 gene dosage. Since FGF family members are widely expressed, these results raise the possibility that further investigation will uncover additional evidence for FGF-dependent effects on lymphocyte function.

Given the ability of FGF ligands to bind more than one receptor family member, it is surprising that compensation for FGF2 deficiency by one of the twenty-two other FGFs was not observed. In this regard, FGF-1 constitutes a plausible candidate because it structurally resembles FGF2 and also is expressed in the spleen (Suzuki et al., 1992, Biochem Biophys Res Commun 186:1192). On the other hand, studies with FGF-1/2 double knock out mice suggest that the mild wound healing and neural phenotypes in FGF2 null mice are not a result of FGF-1 substituting for FGF2 (Miller et al., 2000, Mol Cell Biol 20:2260). The type I independent antigen lipopolysaccharide is a key pathogenic substance in the cell wall of gram negative bacteria. The repeating epitope in this molecule leads to massive engagement of receptors on the surface of B cells, including the BCR, TLR2 and TLR4 (Yang et al., 1998, Nature 395:284; Takeuchi et al., 1999, Immunity 11:443). B cell evolution has developed rapid and vigorous pre-existing defenses against such frequent threats and consequently, antibody secretion in response to this stimulus is robust. The greater response in the absence of FGF2 demonstrates that FGF2 negatively regulates the primary humoral immune response. The magnitude of the enhanced response is greater than the enhancement seen with FC receptor, FC□RIIB, whose deletion shows no effect on the response to LPS at three weeks post immunization (Takai et al., 1996, Nature 379:346). It is believed that this represents the first example of enhanced antibody production in response to LPS due to genetic deficiency.

Animals over-expressing FGF2 have a suppressed humoral immune response to LPS, demonstrating that the gain of function phenotype is the opposite of the loss of function phenotype. It is concluded that FGF2 is both necessary and sufficient to regulate antibody production.

While not being limited by theory, it is not presently clear which step in the humoral immune response is inhibited by FGF2 signaling. Although the possibility that differences in plasma cell generation take place in other lymphoid tissues cannot be excluded, inhibition occurs without a substantial difference in the number of syndecan positive cells in the spleen (FIG. 3, panels D-F). Hence, FGF2 may regulate a step subsequent to the expression of syndecan-1, such as plasmablast migration, full terminal differentiation, or metabolic function of antibody secreting cells in the bone marrow. Consistent with this latter idea, FGF2 is strongly expressed by multiple cell types in the bone marrow (Brunner et al., 1993, Blood 81:631; Chou et al., 2003, Leuk Res 27:499.).

FGF2 may control antibody production either by directly signaling to B cells or indirectly by affecting cells which regulate plasma cell activity. The direct model is consistent with our data showing decreased proliferation in response to FGF signaling of primary mature B lymphocytes (Table 3). While the reduction in cell number is modest, it should be borne in mind that few substances can overcome the strong growth and survival signals turned on by simultaneous CD40 and BCR engagement. In agreement with a direct mode of action, a previous study reported that FGF receptors exist on normal human peripheral blood B cells (Genot, et al., 1989, Cell Immunol 122:424). However, the possibility that other cell types could mediate the observed effects cannot presently be excluded.

A negative correlation between antibody production and germinal center number was found. At first glance, this observation appears contradictory since one might expect that a reduction in germinal centers would decrease antibody production. However, numerous examples have demonstrated that germinal center number can be uncoupled from the humoral response. TNF receptor null animals lack germinal centers but produce substantial antibody titers in response to vesicular stomatitis virus (Karrer et al., 2000, J Immunol 164:768). Similarly, TNF-α null animals display dramatic alterations in splenic morphology but their antibody production to LPS is unaffected (Pasparakis et al., 1996, J Exp Med 184:1397).

Thus, the work described herein demonstrates that FGF2 plays two distinct and complementary roles in the humoral immune response. FGF2 facilitates germinal center formation, thereby contributing to the generation of activated B cells which defend against pathogenic stimuli. On the other hand, FGF2 reduces plasma cell activity and in so doing provides a limit on antibody production. Since FGF2 exerts opposing forces at different times during the B cell response, its activities in the immune system are certainly complex. Such complexity is consistent with observations in other tissues, where FGF signaling can stimulate radically different effects depending on its temporal and spatial locus of action.

Embodiments Relating to Inhibition of FGF2 Activity in a Mammal

In multiple disease states, vaccination provides inadequate protection and low percentages of seroconversion are observed (Cohen D et al., Diagnosis and management of the antiphospholipid syndrome. BMJ. 2010 May 14; 340:c2541). Non-limiting examples of vaccines for which the invention may be employed to increase humoral immune response include, Malaria vaccine (M. Esen et al. Vaccine. 2009 Nov. 16; 27(49):6862-8. Safety and immunogenicity of GMZ2—a MSP3-GLURP fusion protein malaria vaccine candidate); HIV vaccine (Hoxie J A. Annu Rev Med. 2010; 61:135-52. Toward an antibody-based HIV-1 vaccine.); Influenza vaccine (Nguyen M L et al Infect Immun. 2009 November; 77(11):4714-23. The major neutralizing antibody responses to recombinant anthrax lethal and edema factors are directed to non-cross-reactive epitopes); Influenza Vaccine in geriatric patients (Frasca D, Diaz, A, Romero, M et al. Vaccine. 2010 Oct. 22. Intrinsic defects in B cell response to seasonal influenza vaccination in elderly humans.); and Anthrax vaccine (Nguyen M L et al Infect Immun. 2009 November; 77(11): 4714-23. The major neutralizing antibody responses to recombinant anthrax lethal and edema factors are directed to non-cross-reactive epitopes.).

The invention may, for example, be used to increase antibody production and/or humoral immunity in patients, such as human patients, suffering from immunodeficiencies including but not limited to: Common variable immunodeficiency (Rezaei N et al Clin Vaccine Immunol. 2008 April; 15(4):607-11 Serum bactericidal antibody responses to meningococcal polysaccharide vaccination as a basis for clinical classification of common variable immunodeficiency.); primary immunodeficiency disorder (PIDD), Ig deficiency, IgG deficiency; and HIV disease (Acquired Immune Deficiency Syndrome).

One embodiment of the invention provides a method for increasing the humoral immune response to vaccination with an immunogen, for example, an antigen or a live vaccine, in a mammal, that includes: in conjunction with the vaccination of a mammal to the immunogen other than FGF2, inhibiting the activity of FGF2 in the mammal, thereby increasing the humoral immune response to the antigen. In one variation the immunogen is other than a fibroblast growth factor and other than a fibroblast growth factor receptor. The mammal may be a human, such as a geriatric human. The mammal, which may be human, may have an immune deficiency, such as but not limited to Common variable immunodeficiency; primary immunodeficiency disorder (PIDD), an immunoglobulin deficiency such as IgG deficiency, and HIV disease.

Another embodiment of the invention provides a method for treating an immune deficiency in a mammal, such as a human, that includes: increasing the production of endogenous antibodies in the mammal by inhibiting the activity of FGF2 in the mammal. In one variation, the mammal does not have cancer. The immune deficiency may be, for example, but is not limited to: Common variable immunodeficiency; primary immunodeficiency disorder (PIDD), an immunoglobulin deficiency such as IgG deficiency, and HIV disease. Non-human mammals also suffer from immunodeficiencies and may be treated according to the invention. For example, the method may be used to treat immunodeficiency associated with feline immunodeficiency virus (FIV) in a cat, such as a domesticated cat.

A further embodiment of the invention provides a method for treating a microbial infection in a mammal, such as a human, that includes: administering an FGF2 antagonist to a mammal in need of treatment for a microbial infection, wherein the FGF2 antagonist is administered in an amount effective to increase antibody production in the mammal. The method may further include the step of: administering an antibiotic or anti-viral agent to the mammal which is active against the microbial infection. The antibiotic or anti-viral agent is administered such that the effect of the antibiotic or anti-viral agent and that of the FGF2 antagonist are temporally overlapping in the mammal. The microbial infection may, for example, be a bacterial infection, a viral infection or a eukaryotic parasite infection. The method may further include the step of determining that the mammal has a microbial infection prior to administering the FGF2 antagonist.

Another embodiment of the invention provides a method for increasing in vivo antibody production in a mammal, such as a human, that does not have a cancer, which includes the step of inhibiting the activity of FGF2 in the mammal. In one variation, the mammal is a geriatric human or non-human mammal, such as a geriatric domesticated dog or cat.

A related embodiment provides a method for enhancing the production of antisera or polyclonal antibodies generally against a desired immunogen in a non-human mammal that includes the steps of: inhibiting FGF2 activity in the non-human mammal according to any of methods and ways described herein and immunizing the non-human mammal with an immunogen that is not a fibroblast growth factor or a fibroblast growth factor receptor, whereby the production of antibodies against the immunogen in the mammal is enhanced, increased and/or accelerated versus a comparable immunization without the inhibition of FGF2 activity. The method may further include the step of retrieving the polyclonal sera from the non-human mammal and optionally the step of isolating. The immunizing step may, for example, include more than one temporally separated immunization with the immunogen and may, for example, be aided by inclusion of an immunization adjuvant. The methods for production of antisera and polyclonal antibodies are well known and long-established in the art. See, for example, U.S. Pat. No. 5,440,021.

The increase in antibody production in response to inhibition of FGF2 activity in a mammal is a general characteristic of the invention which is not limited to the type of FGF2 inhibitor that is administered to the mammal to inhibit the activity of FGF2. Preferred types of inhibitors of FGF2 activity include antibodies and binding fragments thereof, both monoclonal and polyclonal, which bind to FGF2 and block its interaction with FGF binding receptors and antibodies, both monoclonal and polyclonal, which bind to an FGF receptor such as FGFR1, FGFR2 and FGFR3 and block binding of the ligand (FGF2) to the receptor. For example, a single chain, monoclonal scFv antibody that neutralizes FGF2 may be used such as that described in Tao et al, Selection and characterization of a human neutralizing antibody to human fibroblast growth factor-2, Biochem Biophys Res Commun. 2010 Apr. 9; 394(3):767-73. Epub 2010 Mar. 17 or one obtained by the method described therein. Antibodies blocking FGFR1 such as those those described in Sun et al., Am J Physiol Endocrinol Metab 292:964-976, 2007, or obtained according to the method of this article may be used. Gorbenk et al, Hybridoma, Volume 28, Number 4, 2009 also describes the production of anti-FGFR1 antibodies and their production. Monoclonal antibodies against FGFR3 and their production are described in Qing et al., J. Clin. Invest. 119:1216-1229 (2009) and in Gorbenko et al, Hybridoma, Volume 28, Number 4, 2009, 295-300.

Antibodies contain one or more antigen binding sites that specifically binds with an antigen. Antibodies include, but are not limited to polyclonal, monoclonal, chimeric, and humanized antibodies. Immunologically active portions include monovalent and divalent fragments such as Fv, single chain Fv (scFv), single variable domain (sVD), Fab, Fab' and F(ab')2 fragments. Immunologically active portions can be incorporated into multivalent from such as diabodies, triabodies, and the like. Antibodies further include antigen binding fragments displayed on phage, and antibody conjugates.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Isolated antibodies may, for example, be used as inhibitors of FGF2 activity according to the invention. Examples of isolated antibodies include an anti-FGF2 antibody that has been affinity purified using FGF2, an anti-FGF2 antibody that has been made by a hybridoma or other cell line in vitro, a human anti-FGF2 antibody isolated from a library such as a phage library, and a human anti-FGF2 antibody derived from a transgenic mouse.

In general, naturally occurring antibody molecules are composed of two identical heavy chains and two light chains. Each light chain is usually covalently linked to a heavy chain by an interchain disulfide bond, and the two heavy chains are further linked to one another by multiple disulfide bonds at the hinge region. The individual chains fold into domains having similar sizes (about 110-125 amino acids) and structures, but different functions. The light chain comprises one variable domain ($V_L$) and one constant domain ($C_L$). The heavy chain comprises one variable domain ($V_H$) and, depending on the class or isotype of antibody, three or four constant domains ($C_H1$, $C_H2$, $C_H3$ and $C_H4$). In mice and humans, the isotypes are IgA, IgD, IgE, IgG, and IgM, with IgA and IgG further subdivided into subclasses or subtypes.

The portion of an antibody consisting of $V_L$ and $V_H$ domains is designated "Fv" and constitutes the antigen-binding site. A single chain Fv (scFv) is an engineered protein containing a $V_L$ domain and a $V_H$ domain on one polypeptide chain, wherein the N terminus of one domain and the C terminus of the other domain are joined by a flexible linker. "Fab" refers to the portion of the antibody consisting of $V_L$-$C_L$ (i.e., a light chain) and $V_H$-$C_H1$ (also designated "Fd").

Antibodies include without limitation single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

The antibody variable domains show considerable amino acid sequence variablity from one antibody to the next, particularly at the location of the antigen binding site. Three regions, called "complementarity-determining regions" (CDRs) are found in each of $V_L$ and $V_H$. The CDRs of an antibody are often referred to as "hypervariable regions."

"Fc" is the designation for the portion of an antibody which comprises paired heavy chain constant domains. In an $IgG_1$ antibody, for example, the Fc comprises $C_H2$ and $C_H3$ domains. The Fc of an IgA or an IgM antibody further comprises a $C_H4$ domain. The Fc is associated with Fc receptor binding, activation of complement-mediated cytotoxicity and antibody-dependent cellular-cytotoxicity. For natural antibodies such as IgA and IgM, which are complexes of multiple IgG like proteins, complex formation requires Fc constant domains.

Finally, the "hinge" region separates the Fab and Fc portions of the antibody, providing for mobility of Fabs relative to each other and relative to Fc, as well as including multiple disulfide bonds for covalent linkage of the two heavy chains. Thus, antibodies of the invention include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

Antibody fragments also include polypeptides with amino acid sequences substantially similar to the amino acid sequence of the variable or hypervariable regions of the antibodies of the invention. Substantially the same amino acid sequence is defined herein as a sequence with at least 70%, at least about 80%, at least about 90%, at least about 95% or at least about 99% homology or identity to a compared amino acid sequence, as determined by the FASTA search method in accordance with Pearson and Lipman, Proc. Natl. Acad. Sci. USA 85:2444-2448 (1988).

Antibodies that may be employed as inhibitors according to the invention also include "chimeric" antibodies and binding fragments thereof. Such antibodies generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

Antibodies that may be employed as inhibitors according to the invention also include "humanized" antibodies. Humanized variable domains are constructed in which amino acid sequences which comprise one or more complementarity determining regions (CDRs) of non-human origin are grafted to human framework regions (FRs). For examples, see: Jones, P. T. et al., 1996, Nature 321, 522-25; Riechman, L. et al., 1988, Nature 332, 323-27; and U.S. Pat. No. 5,530,101 to Queen et al. A humanized construct is particularly valuable for elimination of adverse immunogenic characteristics, for example, where an antigen binding domain from a non-human source is desired to be used for treatment in a human. Variable domains have a high degree of structural homology, allowing easy identification of amino acid residues within variable domains which corresponding to CDRs and FRs. See, e.g., Kabat, E. A., et al., 1991, Sequences of Proteins of Immunological Interest. 5th ed. National Center for Biotechnology Information, National Institutes of Health, Bethesda, Md. Thus, amino acids which are likely to participate directly in antigen binding are easily identified. In addition, methods have been developed to preserve or to enhance affinity for antigen of humanized binding domains comprising grafted CDRs. One way is to include in the recipient variable domain the foreign framework residues which influence the conformation of the CDR regions. A second way is to graft the foreign CDRs onto human variable domains with the closest homology to the foreign variable region. Queen, C. et al., 1989, Proc. Natl. Acad. Sci. USA 86, 10029-33. CDRs are most easily grafted onto different FRs by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

Antibodies with variable domains that have been made less immunogenic by replacing surface-exposed residues so as to make the antibody appear as self to the immune system may also be employed as inhibitors (Padlan, E. A., 1991, Mol. Immunol. 28, 489-98). Antibodies have been modified by this process with no loss of affinity (Roguska et al., 1994, Proc. Natl. Acad. Sci. USA 91, 969-973). Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

It is often preferable to employ variable domains that are essentially human as when the recipient of the antibody is human. Human antibodies comprise human $V_H$ and $V_L$ framework regions (FWs) as well as human complementary determining regions (CDRs). Preferably, the entire $V_H$ and $V_L$ variable domains are human or derived from human sequences. The antibodies can be obtained directly from human cells, for example by creating human hybridomas.

Alternatively, human antibodies can be obtained from transgenic animals into which unrearranged human Ig gene segments have been introduced and in which the endogenous mouse Ig genes have been inactivated (reviewed in Brüggemann and Taussig, 1997, Curr. Opin. Biotechnol. 8, 455-58). Preferred transgenic animals contain very large contiguous Ig gene fragments that are over 1 Mb in size (Mendez et al., 1997, Nature Genet. 15, 146-56) but human Mabs of moderate affinity can be raised from transgenic animals containing smaller gene loci (See, e.g., Wagner et al., 1994, Eur. J. Immunol. 42, 2672-81; Green et al., 1994, Nature Genet. 7, 13-21).

Human antibodies can also be obtained from libraries of antibody $V_H$ and/or $V_L$ domains. For example, a variable domain library can be obtained from human genomic sequences, or from peripheral blood lymphocyte expressing productively rearranged variable region genes. Furthermore, the human gene library can be synthetic. In one embodiment, variable domain libraries can be created which comprise human framework regions with one or more CDRs that are synthesized to include random or partial random sequences. For example, a human $V_H$ variable domain library can be created in which members are encoded by a human $V_H$ gene segment and a synthetic sequence for the CDR3H region (i.e., a synthetic $D_H$-$J_H$ gene segment). Likewise, a human $V_L$ variable domain may be encoded by a human $V_L$ gene segment and a synthetic sequence for the CDR3L region (i.e., a synthetic $J_L$ gene segment). In another embodiment, the human frameworks may be synthetic in that they have a consensus sequence derived from known human antibody sequences or subgroups of human sequences. In another alternative, one or more CDRs is obtained by amplification from human lymphocytes expressing rearranged variable domains and then recombined into a particular human framework.

In order to screen libraries of variable domains, it is common to employ phage display libraries wherein combinations of human heavy and light chain variable domains are displayed on the surface of filamentous phage (see, e.g., McCafferty et al., 1990, Nature 348, 552-54; Aujame et al., 1997, Human Antibodies 8, 155-68). Combinations of variable domains are typically displayed on filamentous phage in the form of Fabs or scFvs. The library is screened for phage bearing combinations of variable domains having desired antigen binding characteristics. Preferred single domain and variable domain combinations display high affinity for a selected antigen and little cross-reactivity to other related antigens. By screening very large repertoires of antibody fragments, (see e.g., Griffiths et al., 1994, EMBO J. 13, 3245-60) a good diversity of high affinity binding domains are isolated, with many expected to have sub-nanomolar affinities for the desired antigen.

In a physiological immune response, mutation and selection of expressed antibody genes leads to the production of antibodies having high affinity for their target antigen. The $V_H$ and $V_L$ domains incorporated into antibodies of the invention can similarly be subject to in vitro or in vivo mutation and screening procedures in order to modify affinity and/or specificity. Thus, binding domains of the invention include those for which binding characteristics have been improved by mutating CDRs and/or FW regions by direct mutation, methods of affinity maturation, or chain shuffling. It is understood that amino acid residues that are primary determinants of binding of single domain antibodies can be within Kabat defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

Inhibitors that may be used according to the invention also include antigen binding proteins engineered from non-immunoglobulin scaffolds. For example, affibodies, which are derived from an immunoglobulin-binding domain of S. aureus protein A, possess no disulfide bonds and display reversible folding. Another example is fibronectin, which has an antibody-like structure and displays CDR-like loops. In contrast to antibodies, the fibronectin domain structure does not rely on disulfide bonds, yet displays high thermodynamic stability. Binding sites can be engineered into such scaffolds by, for example, diversifying codons at specified positions and screening for binding to a desired antigen. Codons can be randomized in loops, flat surfaces, cavities, or combinations of such locations. Further, peptide sequences can be inserted, usually in loops. Target-binding variants of resulting libraries can be isolated using selection of screening techniques that are well known in the art, not limited to phage display, ribosome display, bacteria or yeast surface display, and the like. For antigen-binding proteins intended for therapy, various strategies are available for minimizing potential immunogenicity. Human scaffolds can be employed, and immunogenicity can be minimized, for example, by PEGylation or T-cell epitope engineering (i.e., minimizing T-cell reactive sequences).

Antigen-binding proteins from non-immunoglobulin scaffolds often can be produced more economically than immunoglobulin-type proteins. For example, the absence of disulfide bonds or free cysteines allows for expression of functional molecules in the reducing environment of the bacterial cytoplasm, which usually gives higher yields than periplasmic expression, and is more convenient than refolding in vitro. Binz, H. K. et al. (Nat. Biotech. 23:1257-68, 2005) discloses a variety of such antigen-specific binding proteins and techniques for their development.

The identification or selection of antibodies or other molecules that inhibit binding of FGF2 or other FGFs to their receptors may be performed according to routine ligand-receptor binding assays, comparing binding in presence and absence of test agent, since the full sequences of FGF2 and its receptors are known in various mammals such as human. See, for example, U.S. Pat. No. 5,440,021 for ligand-receptor binding assays.

Another preferred type of inhibitor of FGF2 activity is a soluble FGF2-binding receptor or soluble portion of an FGF-binding receptor, such as a soluble form of FGFR1, FGFR2 and FGFR3. The soluble receptor sequence may, for example match the species in which it will be administered, i.e., a human receptor sequence may be used for a human recipient and so on. For example, FP-1039 is a soluble fusion protein consisting of the extracellular domains of human FGFR1 linked to the Fc region of human Immunoglobulin G1 (IgG1), which may be used as an FGF2 inhibitor/antagonist according to the invention (Five Prime Therapeutics, Inc., San Francisco, Calif.; Keer et al, ASCO 2010, Abstract no. TPS260).

FGF2 activity may also be inhibited according to the invention by vaccinating the subject mammal against FGF2 itself or against FGFR1, FGFR2 and/or FGFR3. For example, a peptide vaccine targeting the heparin-binding portion of FGF2 can be used to generate a specific anti-FGF2 antibody response in a mammal according the method of Plum et. al., Generation of a specific immunological response to FGF2 does not affect wound healing or reproduction, Immunopharmacol Immunotoxicol. 2004 February; 26(1):29-41.

For embodiments in which a soluble polypeptide, such as an antibody or soluble receptor, is used to inhibit FGF2 activity, a composition for intravenous administration, for example, to a human, may include 0.1 to 20 mg, such as 0.1 to 10 mg, of the polypeptide, and this may be a daily dose. More generally, dosages from 0.1 mg to about 100 mg per subject per day for one or more days may be used. Methods for preparing administrable compositions are well known to those skilled in the art and are described in more detail in such publications as Remington's Pharmaceutical Science, 19th ed., Mack Publishing Company, Easton, Pa. (1995). Polypeptides for administration to a subject may, for example, be provided in lyophilized form and rehydrated with sterile water before administration. The solution of polypeptide may then be added to an infusion bag containing 0.9% sodium chloride, USP, and, for example administered at a dosage of from 0.5 to 15 mg/kg body weight. Alternatively, for example, the polypeptide can be administered as a bolus injection, for example, at a dosage of 0.5 to 30 mg/kg body weight.

Still other suitable types of FGF2 activity inhibitors include, for example, antisense oligonucleotides targeting FGF2 or one or more of FGFR1, FGFR2 and FGFR3. Still further suitable inhibitors are small molecule inhibitors, for example cardiac glycosides or aglycone derivatives as described in U.S. Pat. No. 6,071,885 and FGF activity modulating oligosaccharides as described in U.S. Pat. No. 5,891,655. TKI258 (also known as CHIR-258) described in Sarker et al., Clin Cancer Res, 2008; 14(7) 2075-81, is another suitable small molecule FGF receptor inhibitor. Brivanib, a FGFR1 Kinase inhibitor described in Bhide et al, Mol Cancer Ther; 9(2) February 2010, 369-78, is still another suitable small molecule inhibitor.

Embodiments Relating to Increasing FGF2 Activity in a Mammal

The invention also provides embodiments in which antibody production in vivo is purposefully reduced in a mammal, such as a human, by increasing FGF2 activity in the mammal, for example, by administration of FGF2 to the mammal or administration of an agonist of FGF2 or an agonist of an FGF2 receptor, such as FGFR1, FGFR2 or FGFR3 to the mammal, in an amount effective to decrease antibody production in the mammal. Where FGF2 is administered to a mammal recipient, the peptide sequence may, for example at least substantially or identically match the species in which it will be administered, i.e., a human receptor sequence may be used for a human recipient and so on.

This aspect of the invention finds practical application is the suppression of antibody production in acutely toxic states. In many cases, response to invading pathogens can lead to pathological autoimmune effects, with lymphocyte activity spiraling out of control. In situations like this, administration of FGF2 attenuates the uncontrolled secretion of antibody.

Similarly, multiple human pathologies result from secretion of autoimmune antibodies. Administration of FGF2 and FGF ligands will serve to attenuate the production of these antibodies and thus ameliorate the autoimmune disease. For example, autoimmune antibodies are observed in both systemic lupus erythematosus (Cohen D et al., Diagnosis and management of the antiphospholipid syndrome. BMJ. 2010 May 14; 340:c2541) and diverse arthritic disease (Calero I, et al., B cell therapies for rheumatoid arthritis: beyond B cell depletion. Rheum Dis Clin North Am 2010 May; 36(2):325-43), including rheumatoid arthritis, psoriatic arthritis, ankylosing spondylitis and juvenile idiopathic arthritis. In addition, increasing FGF2 activity in a mammal may be used to decrease or maintain a decreased level of antibody production in organ transplant patients, such as human organ transplant patients in order to decrease negative immune responses to and increase tolerance to the transplanted organ in the patient.

Accordingly, one embodiment of the invention provides a method for decreasing antibody production, such as pathological antibody production, in a mammal such as a human in need thereof by administering to the mammal FGF2 or an FGF2 agonist or an agonist of a receptor that binds FGF2 such as FGFR1, FGFR2 and FGFR3 in an amount effect to decrease antibody production in the mammal. In one variation, the mammal may have and be in need of treatment for systemic lupus erythematosus and diverse arthritic disease, including rheumatoid arthritis, psoriatic arthritis, ankylosing spondylitis and juvenile idiopathic arthritis and the method decreases the production of autoimmune antibodies in these mammals thereby treating the condition. In another variation, the mammal is an organ transplant patient such as a human organ transplant patient and the method reduces antibody response against the transplanted organ.

The sequences of fibroblast growth factors and their receptors are well characterized in humans and non-human mammals. For example, the following sequences are known and form part of this disclosure: Human FGF2 (NCBI Reference Sequence NM_002006.4; SEQ ID NO:1 peptide, SEQ ID NO:2 nucleotide), Human FGFR1 (GenBank Accession No. M34185.1; SEQ ID NO:3 peptide, SEQ ID NO:4 nucleotide), Human FGFR2 (NCBI Reference Sequence NM_000141.4; SEQ ID NO:5 peptide, SEQ ID NO:6 nucleotide), Human FGFR3 (NCBI Reference Sequence NM_000142.4; SEQ ID NO:7 peptide, SEQ ID NO:8 nucleotide), Human FGFR4 (GenBank Accession No. AF202063.1; SEQ ID NO:9 peptide, SEQ ID NO:10 nucleotide), *Bos taurus* FGF2 (NCBI Reference Sequence NM_174056.3; SEQ ID NO:11 peptide, SEQ ID NO:12 nucleotide), *Bos taurus* FGFR1 (Genbank Accession No. NM_001110207.1; SEQ ID NO:13 peptide, SEQ ID NO:14 nucleotide), *Bos taurus* FGFR2 (NCBI Reference Sequence XM_002698546.1; SEQ ID NO:15 peptide, SEQ ID NO:16 nucleotide); *Bos taurus* FGFR3 (NCBI Reference Sequence NM_174318.3; SEQ ID NO:17 peptide, SEQ ID NO:18 nucleotide), *Bos taurus* FGFR4 (NCBI Reference Sequence XM_002689008.1; SEQ ID NO:19 peptide, SEQ ID NO:20 nucleotide), *Sus scrofa* FGF2 (NCBI Reference Sequence XM_003129213.1; SEQ ID NO:21 peptide, SEQ ID NO:22 nucleotide), *Sus scrofa* FGFR1 (NCBI Reference Sequence: XM_001928678.2; SEQ ID NO:23 peptide, SEQ ID NO:24 nucleotide), *Sus scrofa* FGFR2 (NCBI Reference Sequence NM 001099924.1; SEQ ID NO:25 peptide, SEQ ID NO:26 nucleotide), *Sus scrofa* FGFR3 (GenBank Accession No. BV726808.1; SEQ ID NO:27 cds nucleotide), *Sus scrofa* FGFR4 (NCBI Reference Sequence XM_003123682.1; SEQ ID NO:28 peptide, SEQ ID NO:29 nucleotide), *Macaca mulatta* FGF2 (NCBI Reference Sequence XM_001099284.2; SEQ ID NO:30 peptide, SEQ ID NO:31 nucleotide), *Macaca fascicularis* FGFR1 (GenBank Accession No. AB220417.1; SEQ ID NO:32 peptide, SEQ ID NO:33 nucleotide), Macaca mulatta FGFR2 partial (GenBank Accession No. AY083548.1; SEQ ID NO:34 peptide, SEQ ID NO:35 nucleotide), *Macaca mulatta* FGFR3 (NCBI Reference Sequence XM_002802167.1; SEQ ID NO:36 peptide, SEQ ID NO:37 nucleotide), *Macata mulatta* FGFR4 (NCBI Reference Sequence XM_001087243.2; SEQ ID NO:38 peptide, SEQ ID NO:39 nucleotide), *Mus musculus* FGF2 (NCBI Reference Sequence NM_008006.2; SEQ ID NO:40 peptide, SEQ ID NO:41 nucleotide), *Mus musculus* FGFR1 (NCBI Reference Sequence NM 010206.2; SEQ ID NO:42 peptide, SEQ ID NO:43 nucleotide), *Mus musculus* FGFR2 (NCBI Reference Sequence NM_010207.2; SEQ ID NO:44 peptide, SEQ ID NO:45 nucleotide), *Mus musculus* FGFR3 (NCBI Reference Sequence NM_008010.4; SEQ ID NO:46 peptide, SEQ ID NO:47 nucleotide), and *Mus musculus* FGFR4 (NCBI Reference Sequence NM_008011.2; SEQ ID NO:48 peptide, SEQ ID NO:49 nucleotide).

Without limitation, the invention also provides methods for increasing endogenous antibody production in mammals such as humans by administering any of the following enumerated compounds or pharmacologically acceptable salts thereof:

1. BIBF1120 (Vargatef) Boehringer Ingelheim, chemical name: Methyl (3Z)-3-[({4-[N-methyl-2-(4-methylpiperazin-1-yl)acetamido]phenyl}amino)(phenyl)methylidene]-2-oxo-2,3-dihydro-1H-indole-6-carboxylate.

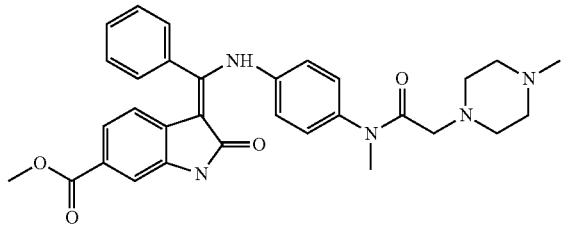

F. Hilberg et al Cancer Res. 2008 Jun. 15; 68(12):4774-82. doi: 10.1158/0008-5472.CAN-07-6307. BIBF 1120: triple angiokinase inhibitor with sustained receptor blockade and good antitumor efficacy.

2. TKI258 (Dovitinib) Novartis, chemical name: 4-amino-5-fluoro-3-[5-(4-methylpiperazin-1-yl)-1H-benzo[d]imidazol-2-yl]-3,4-dihydronaphthalen-2(1H)-one

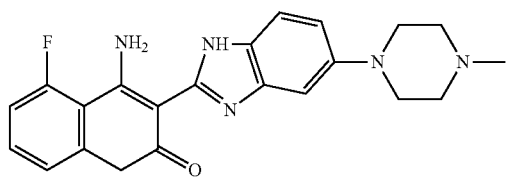 [SMILES: CN1CCN(c2ccc3[nH]c(C4=C(N)c5c(F)cccc5CC4=O)nc3c2)CC1]

Trudel S, et al Blood. 2005 Apr. 1; 105(7):2941-8. Epub 2004 Dec. 14. CHIR-258, a novel, multitargeted tyrosine kinase inhibitor for the potential treatment of t(4;14) multiple myeloma.

3. BMS582664 (Brivanib) Bristol Myers Squib chemical name: (1R)-2-[[4-[(4-fluoro-2-methyl-1H-indol-5-yl)oxy]-5-methylpyrrolo[2,1-f][1,2,4]triazin-6-yl]oxy]-1-methylethyl(2S)-2-aminopropanoate

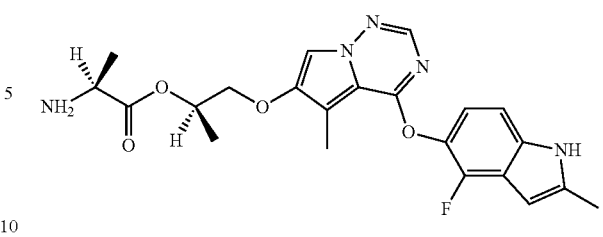

Bhide R S et al J Med. Chem. 2006 Apr. 6; 49(7):2143-6. Discovery and preclinical studies of (R)-1-(4-(4-fluoro-2-methyl-1H-indol-5-yloxy)-5-methylpyrrolo[2,1-f][1,2,4]triazin-6-yloxy)propan-2-ol (BMS-540215), an in vivo active potent VEGFR-2 inhibitor.

4. E7080 Eisai chemical name: 4-[3-Chloro-4-(3-cyclopropylureido)phenoxy]-7-methoxyquinoline-6-carboxamide

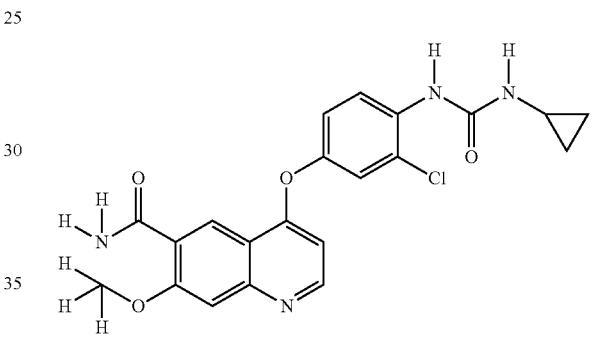

Boss D S et al Br J. Cancer. 2012 May 8; 106(10):1598-604. doi: 10.1038/bjc.2012.154. Epub 2012 Apr. 19. A phase I study of E7080, a multitargeted tyrosine kinase inhibitor, in patients with advanced solid tumours.

5. AZ2171 (Cediranib) Astra Zeneca chemical name: 4-[(4-Fluoro-2-methyl-1H-indol-5-yl)oxy]-6-methoxyl-7-(3-pyrrolidin-1-ylpropoxy)quinazoline

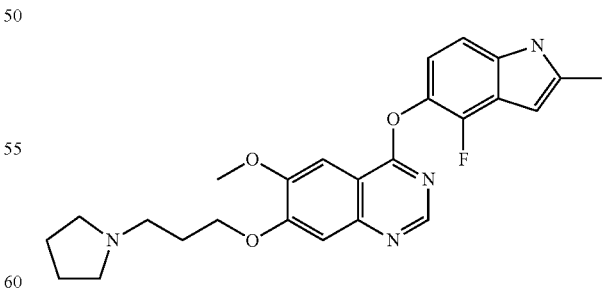

Wedge S R et al Cancer Res. 2005 May 15; 65(10):4389-400. AZD2171: a highly potent, orally bioavailable, vascular endothelial growth factor receptor-2 tyrosine kinase inhibitor for the treatment of cancer.

6. AZD4547 Astra Zeneca chemical name: N-[5-[2-(3,5-Dimethoxyphenyl)ethyl]-2H-pyrazol-3-yl]-4-(3,5-dimethylpiperazin-1-yl)benzamide

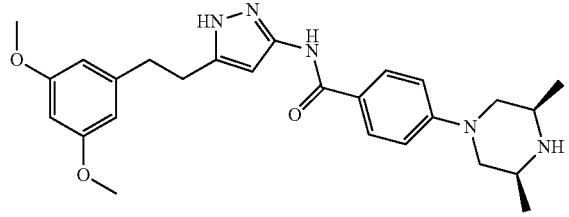 [SMILES: COc1cc(CCc2cc(NC(=O)c3ccc(N4C[C@@H](C)N[C@@H](C)C4)cc3)n[nH]2)cc(OC)c1]

Gavine P R Cancer Res. 2012 Apr. 15; 72(8):2045-56. doi: 10.1158/0008-5472.CAN-11-3034. Epub 2012 Feb. 27. AZD4547: an orally bioavailable, potent, and selective inhibitor of the fibroblast growth factor receptor tyrosine kinase family.

7. TSU68(SU6668) Taiho Pharmaceutical chemical name: (E)-3-[2,4-Dimethyl-5-[(2-oxoindolin-3-ylidene)methyl]-1H-pyrrol-3-yl]propanoic acid

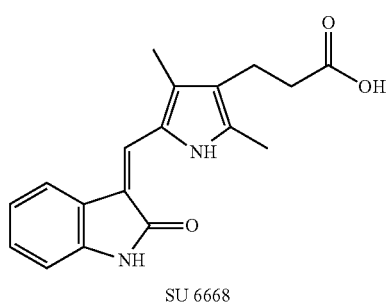 [SMILES: Cc1[nH]c(/C=C2\C(=O)Nc3ccccc32)c(C)c1CCC(=O)O]

SU 6668

Yorozuya K, et al Oncol Rep. 2005 September; 14(3):677-82. TSU-68 (SU6668) inhibits local tumor growth and liver metastasis of human colon cancer xenografts via anti-angiogenesis.

8. BGJ398 Novartis chemical name: 3-(2,6-Dichloro-3,5-dimethoxy-phenyl)-1-{6-[4-(4-ethyl-piperazin-1-yl)-phenylamino]-pyrimidin-4-yl}-1-methyl-urea

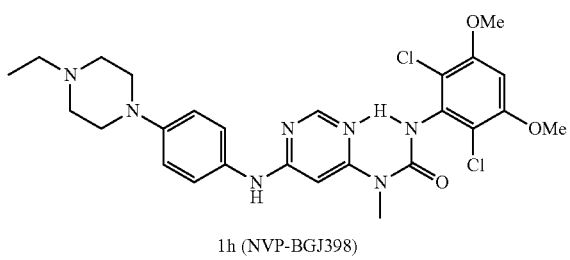

1h (NVP-BGJ398)

Guagnano V, et al J Med. Chem. 2011 Oct. 27; 54(20): 7066-83. doi: 10.1021/jm2006222. Epub 2011 Sep. 21. Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase.

9. ENMD2076 Miikana Therapeutics chemical name: 6-(4-Methylpiperazin-1-yl)-N-(5-methyl-1H-pyrazol-3-yl)-2-[(E)-2-phenylvinyl]pyrimidin-4-amine L-tartrate

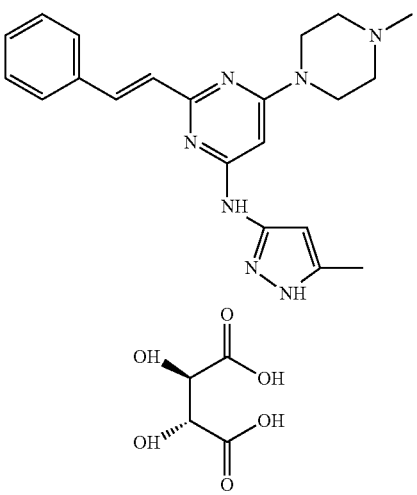

Matulonis U A, et al Eur J. Cancer. 2013 January; 49(1):121-31. doi: 10.1016/j.ejca.2012.07.020. Epub 2012 Aug. 21. ENMD-2076, an oral inhibitor of angiogenic and proliferation kinases, has activity in recurrent, platinum resistant ovarian cancer.

10. AP24534 (Ponatinib) Ariad Pharmaceuticals chemical name: Benzamide, 3-(2-imidazo[1,2-b]pyridazin-3-ylethynyl)-4-methyl-N-[4-[(4-methyl-1-piperazinyl)methyl]-3-(trifluoromethyl)phenyl]

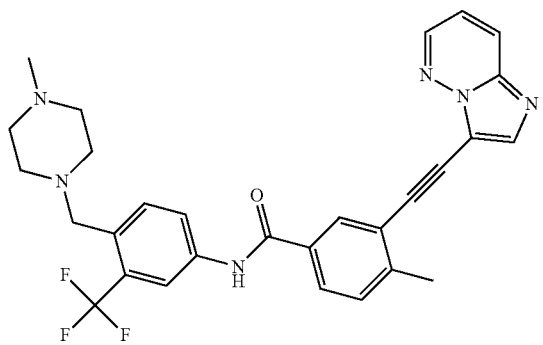 [SMILES: Cc1ccc(C(=O)Nc2ccc(CN3CCN(C)CC3)c(C(F)(F)F)c2)cc1C#Cc1cnc2cccnn12]

Chase A, et al. Haematologica. 2013 January; 98(1):103-6. doi: 10.3324/haematol.2012.066407. Epub 2012 Aug. 8. Ponatinib as targeted therapy for FGFR1 fusions associated with the 8p11 myeloproliferative syndrome.

11. AXL1717 Axelar chemical name: Furo(3',':6,7)naphtho(2,3-d)-1,3-dioxol-6(5aH)-one, 5,8,8a,9-tetrahydro-9-hydroxy-5-(3,4,5-trimethoxyphenyl)-, (5R-(5-alpha,5a-alpha,8a-alpha,9-alpha))-

Ekman S, Acta Oncol. 2011 April; 50(3):441-7. doi: 10.3109/0284186X.2010.499370. Epub 2010 Aug. 11. Clinical Phase I study with an Insulin-like Growth Factor-1 receptor inhibitor: experiences in patients with squamous non-small cell lung carcinoma.

12. FP1039 (fusion protein) Five Prime, Human Genome Sciences, Glaxo Smith Kline. FP 1039 comprises the extracellular domain of human fibroblast growth factor receptor 1c (FGFR1) linked to the Fc portion of human IgG1. The molecule is designed to trap FGFR1 ligands and prevent binding to FGF receptors. Harding et al., Preclinical efficacy of FP-1039 (FGFR1:Fc) in endometrial carcinoma models with activating mutations in FGFR2. 101st *Annual Meeting of the American Association for Cancer Research*.: abstr. 2597, 17 Apr. 2010

13. MFGR 1877S FGFR3Mab Genentech. Qing J et al J Clin Invest. 2009 May; 119(5):1216-29. doi: 10.1172/ JCI38017. Epub 2009 Apr. 20. Antibody-based targeting of FGFR3 in bladder carcinoma and t(4;14)-positive multiple myeloma in mice.

14. Aveo GP369 FGFR2 mAb. Bai A Cancer Res. 2010 Oct. 1; 70(19):7630-9. doi: 10.1158/0008-5472.CAN-10-1489. Epub 2010 Aug. 13. GP369, an FGFR2-IIIb-specific antibody, exhibits potent antitumor activity against human cancers driven by activated FGFR2 signaling.

15. FGFR1 and FGFR3 mAbs Imclone Systems. Sun H D et alAm J Physiol Endocrinol Metab. 2007 March; 292(3): E964-76. Epub 2006 Nov. 28. Monoclonal antibody antagonists of hypothalamic FGFR1 cause potent but reversible hypophagia and weight loss in rodents and monkeys; Deevi D S, Direnzo R, Li H, Malabunga M, Prewett M C Inhibiting FGFR3 for enhancing the cytotoxic effects of cisplatin on bladder cancer cells and possible mechanisms. 2007 AACR-NCI-EORTC International Conference on Molecular Targets and Cancer Therapeutics.: 176-177 (plus poster) abstr. B48, 22 Oct. 2007.

16. FGF2 and FGFR2 mAbs Galaxy Biotech. Wang L, et al. Mol Cancer Ther. 2012 April; 11(4):864-72. doi: 10.1158/1535-7163.MCT-11-0813. Epub 2012 Feb. 16. A novel monoclonal antibody to fibroblast growth factor 2 effectively inhibits growth of hepatocellular carcinoma xenografts; Zhao W M, Clin Cancer Res. 2010 Dec. 1; 16(23):5750-8. doi: 10.1158/1078-0432.CCR-10-0531. Epub 2010 Jul. 29. Monoclonal antibodies to fibroblast growth factor receptor 2 effectively inhibit growth of gastric tumor xenografts.

17. SAR 106881, Sanofi Aventis Research program FGFR agonists

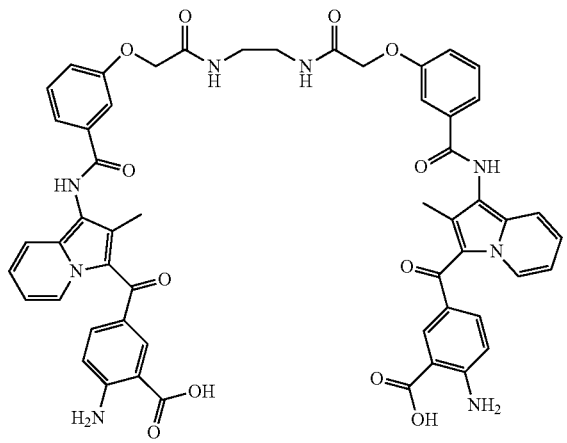

A name could not be generated for this structure

Guillo, Making agonists from antagonists: SAR106881, a breakthrough in FGFRs activation and a potential treatment to improve peripheral revascularization and reduce neuropathic pain. 240th National Meeting of the American Chemical Society.: (plus oral presentation) abstr. MEDI 23, 22 Aug. 2010.

18. JNJ 42756493 FGFR antagonists Astex Therapeutics/Janssen Research. Squires et al., Development of inhibitors of the fibroblast growth factor receptor (FGFR) kinase using a fragment based approach. 101st *Annual Meeting of the American Association for Cancer Research*.: abstr. 3626, 17 Apr. 2010.

The compounds or pharmacologically acceptable sales thereof may, for example, be administered in therapeutically effective amounts to a mammal such as a human in need of increasing endogenous antibody production who is not in need of treatment for a cancer. The mammal may have an immune deficiency such as a humoral immune deficiency or any of the immune deficiencies described herein. The mammal may, for example, be geriatric. The compounds or pharmaceutically acceptable salts thereof, may for example, be administered in an amount effective to increase endogenous antibody production in conjunction with a vaccination with an immunogen (other than FGF2 or an FGF) to improve the humoral immune response to the vaccination. The compounds or pharmaceutically acceptable salts thereof, may for example, be administered in an amount effective to increase endogenous antibody production to a mammal, such as a human, in need of treatment for a microbial infection or viral infection, for example, alone or in addition to (or in conjunction with) administration of an antibiotic or antiviral agent. In any of the methods, the mammal may be one that is not in need of treatment for cancer. The invention also provides corresponding first and second medical uses for each of the methods of treatment described in this disclosure. Accordingly, the invention provides the use of the agents for modulating humoral immunity and for treatment of the conditions described and also provides use of the agents for the manufacture of medicaments for modulating humoral immunity and for the treatment of the conditions described herein.

Non-human mammals with which the invention may be used include, for example, livestock animals, such as Bovidae, for example cows and sheep, and swine, also Equidae such as horses, canines such as companion domesticated dogs and felines such as companion domesticated cats, primates, Lagomorphs such as rabbits and Rodentia such as rats and mice. The invention is also applicable in birds such as foul, for example, chickens, turkeys and quail, ducks and geese. Accordingly, the invention provides corresponding embodiments and variations as described herein for mammals but applied to avians, such as the aforementioned avians. The sequences of *Gallus gallus* FGF2 (NCBI Reference Sequence: NM_205433.1; SEQ ID NO:50 peptide, SEQ ID NO:51 nucleotide), *Gallus gallus* FGFR1 (NCBI Reference Sequence: NM_205510.1; SEQ ID NO:52 peptide, SEQ ID NO:53 nucleotide), *Gallus gallus* FGFR2 (NCBI Reference Sequence: NM_205319.1; SEQ ID NO:54 peptide, SEQ ID NO:55 nucleotide), and *Gallus gallus* FGFR3 (NCBI Reference Sequence: NM_205509.2; SEQ ID NO:56 peptide, SEQ ID NO:57 nucleotide) also form part of this disclosure.

While the above examples relate to FGF2 and its receptors, the invention also provides corresponding embodiments for each embodiment and variation described herein for a fibroblast growth factor and/or FGF receptor generally, and for other specific fibroblast growth factors such as, but not limited to, FGF1 and FGF3.

Each of the patents and other publications cited in this disclosure is incorporated by reference in its entirety.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method for increasing endogenous antibody production in a mammal in need thereof and not in need of treatment for cancer, comprising:
    administering to a mammal in need of increased endogenous antibody production and not in need of treatment for cancer, a therapeutically effective amount of a compound selected from the group consisting of: ponatinib; N-[5-[2-(3,5-Dimethoxyphenyl)ethyl]-2H-pyrazol-3-yl]-4-(3,5-dimethylpiperazin-1-yl)benzamide; and 3-(2,6-Dichloro-3,5-dimethoxy-phenyl)-1-{6-[4-(4-ethyl-piperazin-1-yl)-phenylamino]-pyrimidin-4-yl}-1-methyl-urea,
    or a pharmaceutically-acceptable salt thereof.

2. The method of claim 1, wherein the mammal is a human.

3. The method of claim 1, wherein the mammal is a geriatric human.

4. The method of claim 1, wherein the mammal has an immune deficiency.

5. The method of claim 4, wherein the mammal is a human.

6. A method for increasing humoral immune response to vaccination with an immunogen in a mammal, comprising:
    in conjunction with the vaccination of a mammal to an immunogen, administering to the mammal a compound selected from the group consisting of: ponatinib; N-[5-[2-(3,5-Dimethoxyphenyl)ethyl]-2H-pyrazol-3-yl]-4-(3,5-dimethylpiperazin-1-yl)benzamide; and 3-(2,6-Dichloro-3,5-dimethoxy-phenyl)-1-{6-[4-(4-ethyl-piperazin-1-yl)-phenylamino]-pyrimidin-4-yl}-1-methyl-urea,
    or a pharmaceutically-acceptable salt thereof.

7. The method of claim 6, wherein the mammal is a human.

8. The method of claim 6, wherein the mammal is not in need of treatment for cancer.

9. The method of claim 8, wherein the mammal is a human.

10. The method of claim 1, wherein the compound is N-[5-[2-(3,5-Dimethoxyphenyl)ethyl]-2H-pyrazol-3-yl]-4-(3,5-dimethylpiperazin-1-yl)benzamide.

11. The method of claim 1, wherein the compound is 3-(2,6-Dichloro-3,5-dimethoxy-phenyl)-1-{6-[4-(4-ethyl-piperazin-1-yl)-phenylamino]-pyrimidin-4-yl}-1-methyl-urea.

12. The method of claim 6, wherein the compound is N-[5-[2-(3,5-Dimethoxyphenyl)ethyl]-2H-pyrazol-3-yl]-4-(3,5-dimethylpiperazin-1-yl)benzamide.

13. The method of claim 6, wherein the compound is 3-(2,6-Dichloro-3,5-dimethoxy-phenyl)-1-{6-[4-(4-ethyl-piperazin-1-yl)-phenylamino]-pyrimidin-4-yl}-1-methyl-urea.

* * * * *